United States Patent
Chin et al.

(10) Patent No.: US 11,213,284 B2
(45) Date of Patent: Jan. 4, 2022

(54) SYSTEMS, DEVICES, AND METHODS FOR CLOSING AN ABDOMINAL WALL DEFECT

(71) Applicant: TAS Medical Inc., San Carlos, CA (US)

(72) Inventors: Albert K Chin, Palo Alto, CA (US); Thomas A Kramer, San Carlos, CA (US)

(73) Assignee: TAS Medical, Inc., San Carlos, CA (US)

( * ) Notice: Subject to any disclaimer, the term of this patent is extended or adjusted under 35 U.S.C. 154(b) by 268 days.

(21) Appl. No.: 16/477,874

(22) PCT Filed: Jan. 16, 2018

(86) PCT No.: PCT/US2018/013764
§ 371 (c)(1),
(2) Date: Jul. 12, 2019

(87) PCT Pub. No.: WO2018/132801
PCT Pub. Date: Jul. 19, 2018

(65) Prior Publication Data
US 2019/0365364 A1    Dec. 5, 2019

(51) Int. Cl.
*A61B 17/30*    (2006.01)
*A61B 17/04*    (2006.01)
(Continued)

(52) U.S. Cl.
CPC ...... *A61B 17/0057* (2013.01); *A61B 17/0467* (2013.01); *A61B 17/0469* (2013.01);
(Continued)

(58) Field of Classification Search
CPC . A61B 17/0057; A61B 34/30; A61B 17/0467; A61B 17/0469; A61B 17/0482;
(Continued)

(56) References Cited

U.S. PATENT DOCUMENTS 5,217,003 A * 6/1993 Wilk .................. A61B 1/00147
600/109
5,312,410 A * 5/1994 Miller ..................... B25B 25/00
606/86 R
(Continued)

FOREIGN PATENT DOCUMENTS

EP    0779461 B1    2/2000
EP    3042622 B1    5/2018
(Continued)

OTHER PUBLICATIONS

EPO Office Action for Application No. 18738928.3 dated Jul. 8, 2020.
(Continued)

*Primary Examiner* — Julian W Woo
(74) *Attorney, Agent, or Firm* — Barnes & Thornburg LLP; Jeffrey R. Stone

(57) ABSTRACT

Systems, devices and methods for closing a tissue defect comprise a subcutaneous guide that is placed transcutaneously between two skin access sites and a self-locking strap that may be advanced into the body through a first access site via a first needle and then passed to a second needle. The strap may be withdrawn with the second needle through a second access site to the outside of the body. The strap may be withdrawn from the first needle, leaving the strap placed through both access sites and across the defect. As the subcutaneous guide is withdrawn from the body it pulls the captured strap such that both ends of the strap protrude from the first access site, allowing the strap to be tightened around the defect.

71 Claims, 43 Drawing Sheets

(51) Int. Cl.
*A61B 34/30* (2016.01)
*A61B 17/00* (2006.01)
A61B 90/00 (2016.01)
A61B 17/06 (2006.01)

(52) U.S. Cl.
CPC ...... *A61B 17/0482* (2013.01); *A61B 17/0487* (2013.01); *A61B 34/30* (2016.02); *A61B 2017/00349* (2013.01); *A61B 2017/00663* (2013.01); *A61B 2017/06057* (2013.01); *A61B 2017/06176* (2013.01); *A61B 2090/064* (2016.02)

(58) Field of Classification Search
CPC .......... A61B 17/0487; A61B 2090/064; A61B 2017/00349; A61B 2017/00663; A61B 2017/06057; A61B 2017/06176; A61B 2017/0488; A61B 2017/0496; A61B 17/06109
USPC ......................................................... 606/148
See application file for complete search history.

(56) References Cited

U.S. PATENT DOCUMENTS

| | | | |
|---|---|---|---|
| 5,500,000 A | 3/1996 | Feakin et al. | |
| 5,669,935 A | 9/1997 | Rosenman et al. | |
| 5,741,283 A * | 4/1998 | Fahy | A61B 17/0057 606/157 |
| 6,050,998 A * | 4/2000 | Fletcher | A61B 17/688 606/103 |
| 7,491,212 B2 * | 2/2009 | Sikora | A61B 17/0467 606/148 |
| 8,048,087 B2 | 11/2011 | Rehnke | |
| 8,696,692 B2 * | 4/2014 | Hoglund | A61B 17/12009 606/151 |
| 8,777,965 B2 | 7/2014 | Chen et al. | |
| RE45,426 E | 3/2015 | Buncke et al. | |
| 9,055,940 B2 * | 6/2015 | Chin | A61B 17/0469 |
| 9,078,648 B2 | 7/2015 | Ziniti et al. | |
| 9,237,889 B2 | 1/2016 | Dumanian et al. | |
| 9,398,943 B2 | 7/2016 | Criscuolo et al. | |
| 9,402,986 B2 | 8/2016 | Bell et al. | |
| 9,439,746 B2 | 9/2016 | Bell et al. | |
| 9,585,705 B2 * | 3/2017 | Koch | A61B 17/1604 |
| 9,637,291 B2 * | 5/2017 | Montejo | B65D 63/16 |
| 9,816,884 B2 * | 11/2017 | Gerber | G01L 1/2206 |
| 9,861,379 B2 | 1/2018 | Chin et al. | |
| 10,543,073 B2 | 1/2020 | Chin et al. | |
| 2004/0176785 A1 | 9/2004 | Hermann et al. | |
| 2004/0267309 A1 | 12/2004 | Garvin | |
| 2008/0255591 A1 | 10/2008 | Harada et al. | |
| 2009/0234379 A1 | 9/2009 | Rehnke | |
| 2014/0330292 A1 | 11/2014 | Levin et al. | |
| 2015/0157327 A1 | 6/2015 | Hoglund | |
| 2015/0245833 A1 | 9/2015 | Chin | |
| 2015/0282806 A1 | 10/2015 | Jorgensen et al. | |
| 2016/0310146 A1 | 10/2016 | Levy et al. | |
| 2018/0116778 A1 | 5/2018 | Chin et al. | |
| 2019/0192142 A1 | 6/2019 | Dumanian | |

FOREIGN PATENT DOCUMENTS

| | | |
|---|---|---|
| SE | 1250787 C2 | 6/2015 |
| WO | 2005002452 A1 | 1/2005 |
| WO | 2012006375 A1 | 1/2012 |
| WO | 2013095898 A1 | 6/2013 |
| WO | 2017051409 A1 | 3/2017 |
| WO | 2019132801 A1 | 7/2018 |

OTHER PUBLICATIONS

International Search Report and Written Opinion for PCT/US2018/013764 dated Jul. 25, 2019 and included with this filing.

* cited by examiner

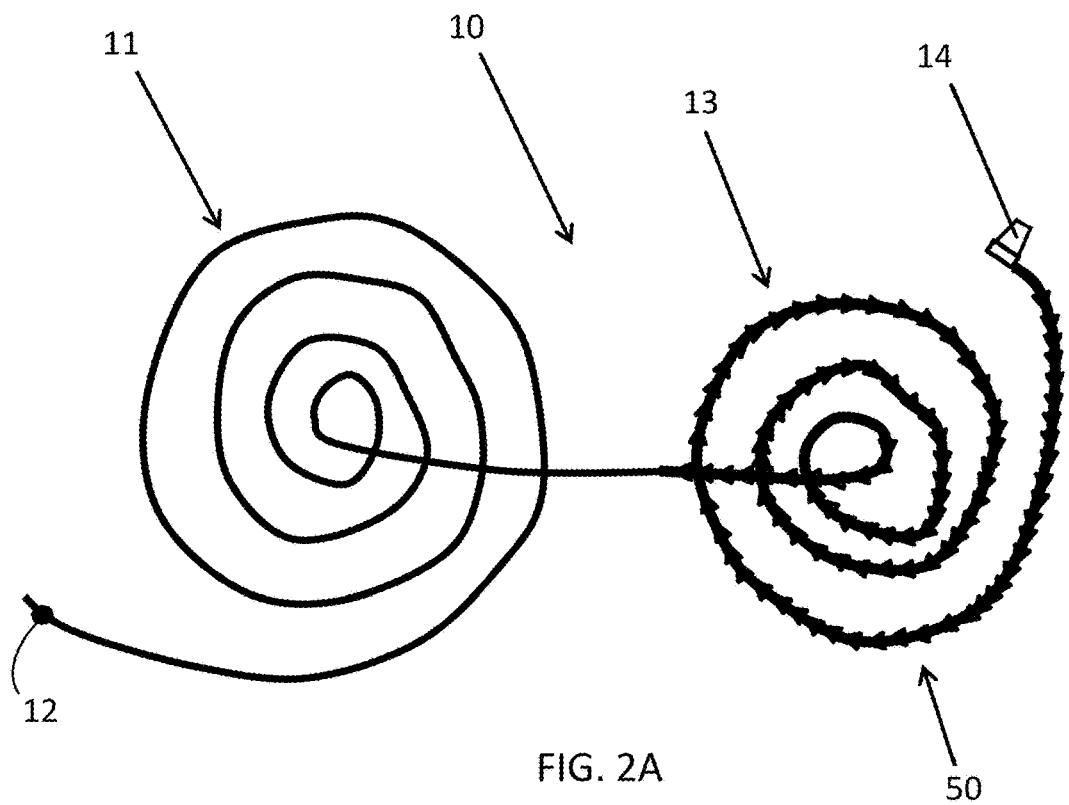
FIG. 2A
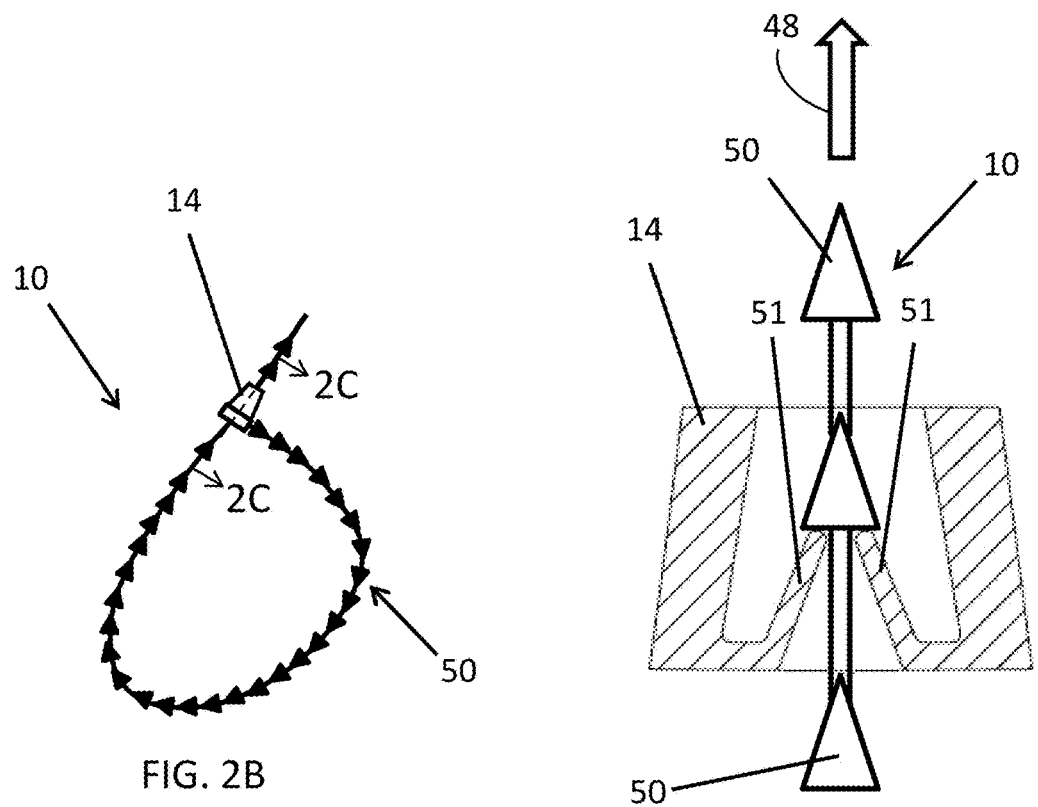
FIG. 2B
FIG. 2C

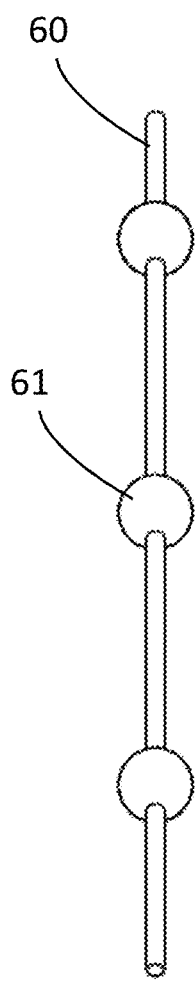
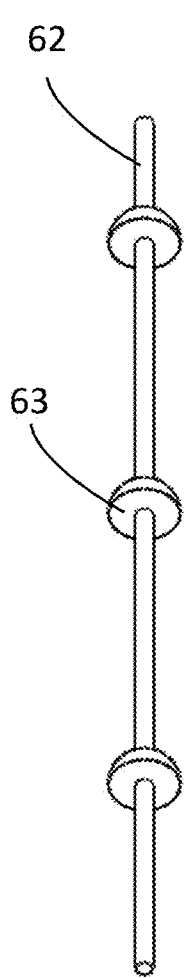
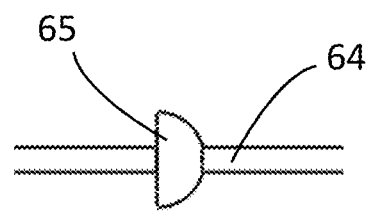
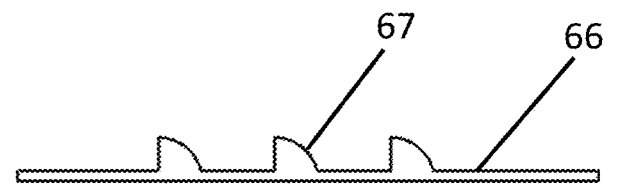
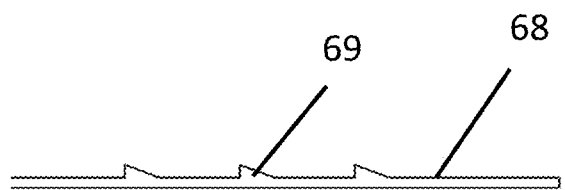
FIG. 2D   FIG. 2E   FIG. 2F   FIG. 2G   FIG. 2H
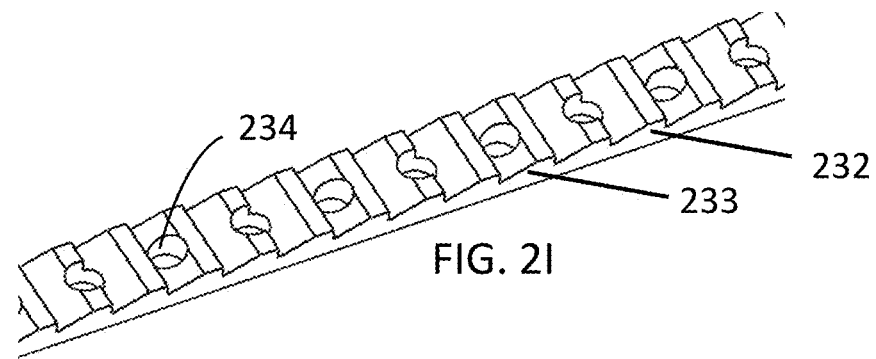
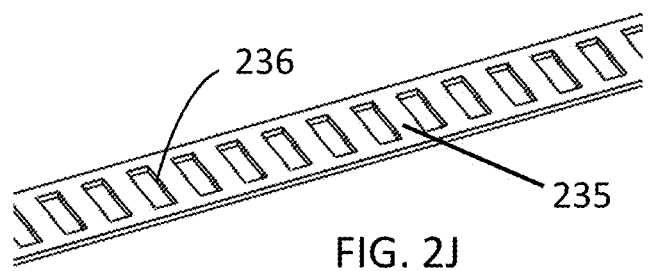
FIG. 2I
FIG. 2J

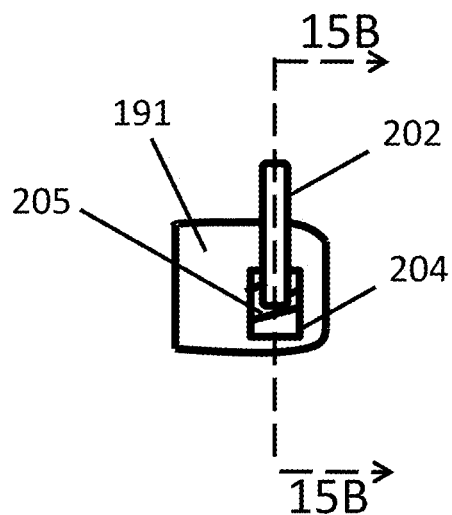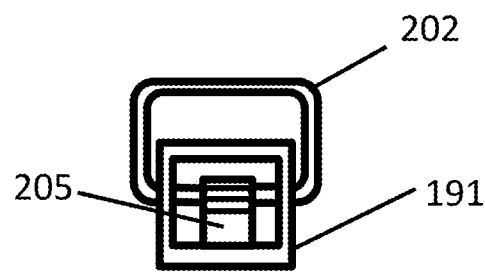
FIG. 15A   FIG. 15B
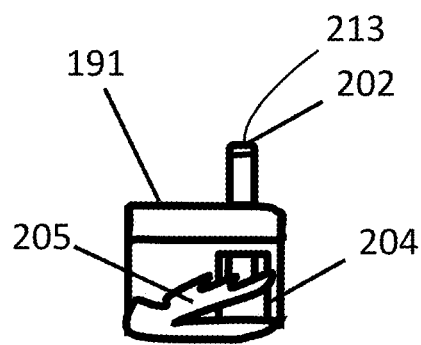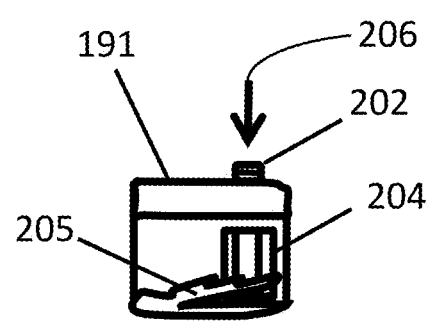
FIG. 15C   FIG. 15D
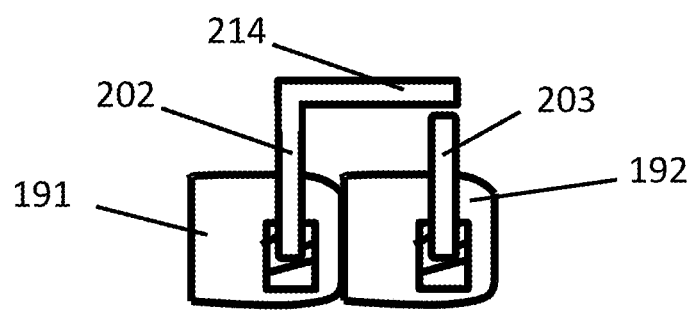
FIG. 15E

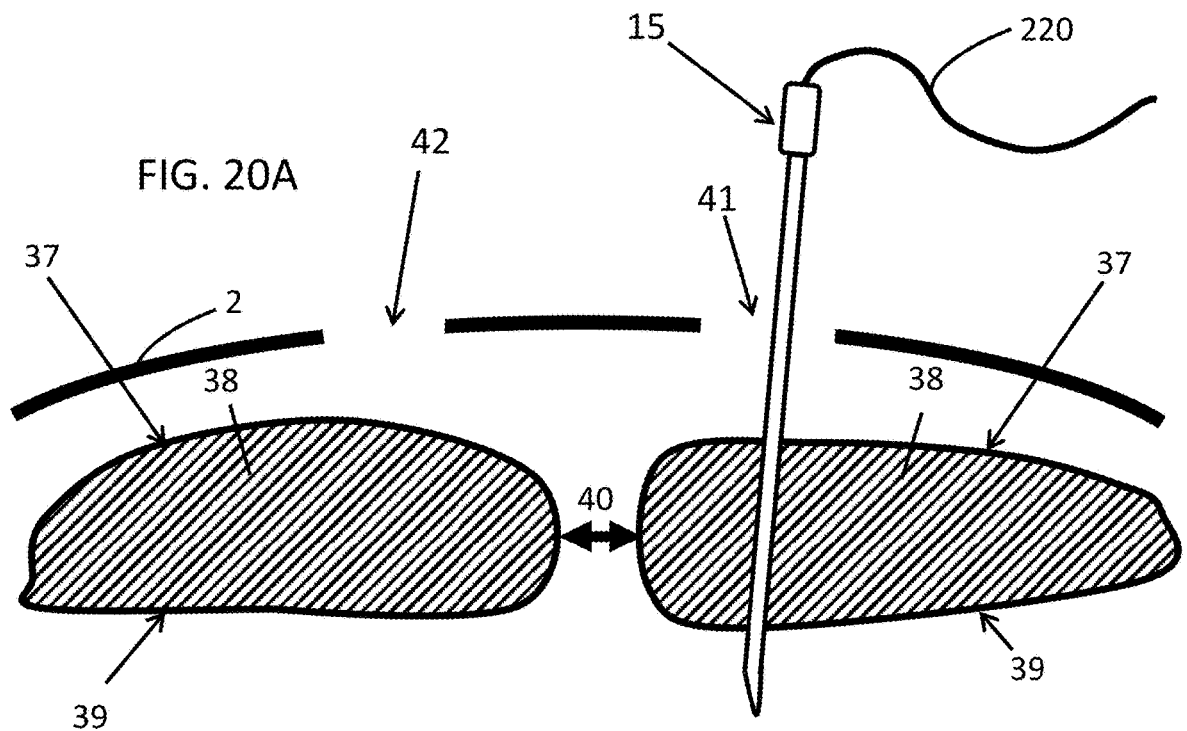
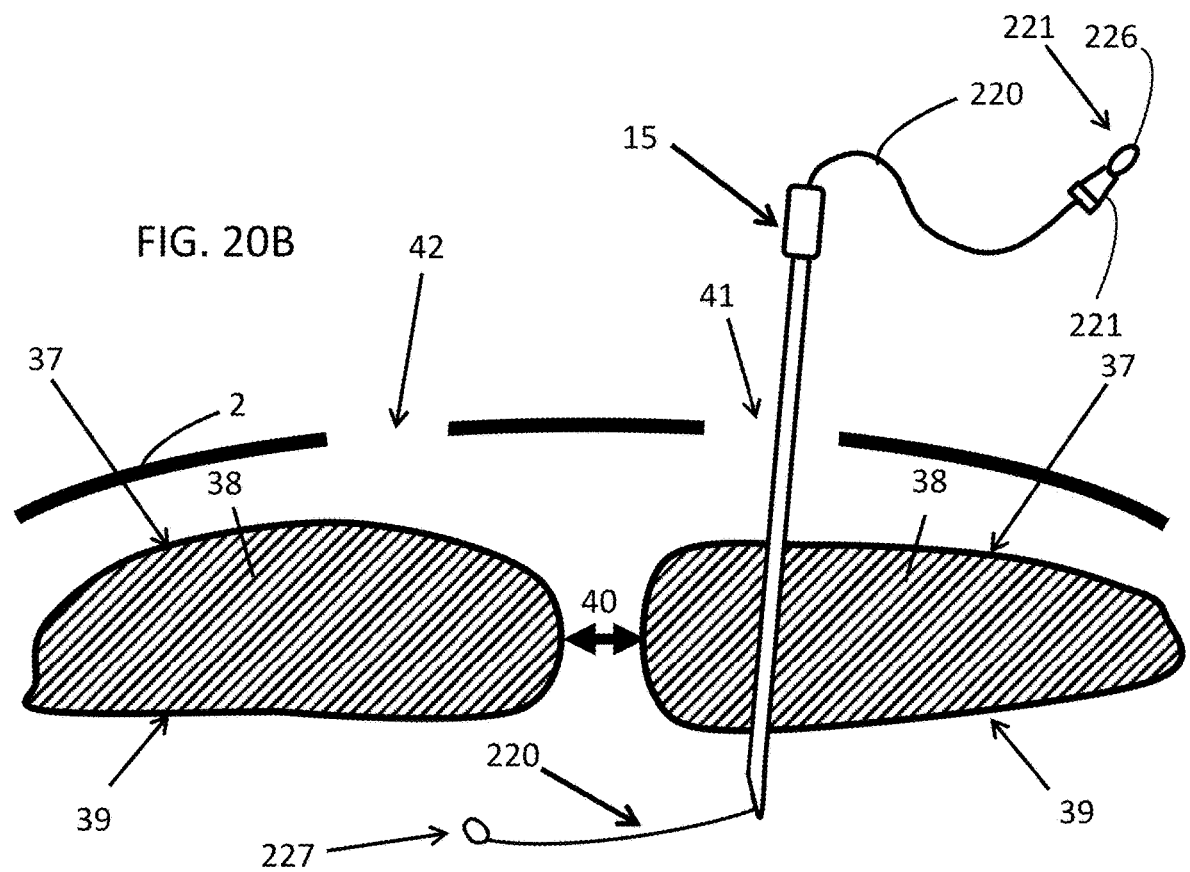

SYSTEMS, DEVICES, AND METHODS FOR CLOSING AN ABDOMINAL WALL DEFECT

CROSS-REFERENCE TO RELATED APPLICATIONS

This application is a national stage filing of International Application No. PCT/US2018/013764, filed Jan. 16, 2018, the entirety of which is hereby incorporated herein by reference. This application claims the benefit and priority of U.S. Provisional Application Ser. No. 62/446,029, filed on Jan. 13, 2017, the entirety of which is hereby incorporated herein by reference.

TECHNICAL FIELD

This disclosure relates generally to devices and methods for closure of a defect in tissue. More specifically, it relates to methods and devices for performing ventral hernia repair.

BACKGROUND

A hernia may occur in a muscle wall where the muscles have weakened or where a previous surgery took place. While weakened abdominal muscles can result in a ventral hernia, more often ventral hernias are abdominal wall defects that generally occur following a breakdown in the closure of a previous abdominal open surgical midline incision and often resulting in abdominal tissue pushing through the tear in the abdominal wall to form a bulge or hernia sac. 350,000-500,000 ventral hernias are repaired annually in the United States. In large ventral hernias, the defect may be greater than 10 cm wide and 40 cm or more in length and extend below the xiphoid process of the sternum inferiorly to the pubic symphysis. The defect may lie under substantial layers of tissue, the skin being the outermost layer. Beneath the skin, there may be 5-10 cm of subcutaneous fat, an external fascial layer, the rectus abdominus muscle, and another layer of fascial tissue. In ventral hernia repair it may be desirable to suture through all of these layers of tissue in order to reappose (close) the defect. They may be repaired via conventional "open" methods requiring a large incision, or laparoscopic procedures requiring small abdominal incisions.

Ventral hernias may arise after a patient undergoes abdominal surgery. For example, upon completion of an open abdominal surgical procedure, closure of the full thickness abdominal wall is performed. Interrupted sutures are placed through the anterior rectus sheath, the rectus muscle, and the posterior rectus sheath. These conventional repair techniques have a long-term failure rate of 41%-52%, leading to ventral hernia formation. Poor tissue strength coupled with significant tension in the suture lines leads to failure of the abdominal closure requiring hernia repair.

In conventional laparoscopic repair, multiple trocar ports are inserted to place a large patch of prosthetic mesh to cover the defect. This approach causes far less postoperative pain as compared to open methods because a large abdominal incision is avoided. However, the abdominal defect is generally not fully closed. Instead, the large prosthetic patch is tacked onto the inner surface of the abdominal wall to cover the defect. Placement of a large piece of artificial material results in a high rate of postoperative complications including seroma formation. The fluid loculation of the seroma then increases the potential for infection of the laparoscopically placed mesh, necessitating its removal plus antibiotic therapy. Bowel adhesions are also a potential complication due to the implantation of a large foreign body patch.

It is desirable to close the abdominal defect using a laparoscopic technique, either partially or completely, to significantly decrease the size of the prosthetic mesh patch needed to repair a ventral hernia or eliminate the use of a mesh patch entirely at the discretion of the surgeon. Current methods use sutures which must be advanced into the body cavity through multiple layers of tissue including full-thickness abdominal walls, and as such, the sutures are difficult to find and manipulate when inserted into the body cavity. After looping around the muscle and both ends of the suture may exit from a single site, and a slip knot composed of two half-hitches is tied in the suture, and the suture is tensioned by holding onto one suture limb while advancing a laparoscopic knot pusher down the opposite suture limb. Tension must be maintained on the slip knot as multiple sutures used in the repair of the hernia are serially tensioned to close the large abdominal defect gradually. Tension may be maintained by applying a surgical clamp to the base of the knot. However, if the patient is obese, it may be difficult or impossible to advance the jaws of a surgical clamp a distance of 5-10 cm down a tiny skin puncture to the location of the knot. In the non-obese patient, the presence of numerous surgical clamps on the abdominal wall of the patient makes it cumbersome for the surgeon to manipulate and function during the procedure. After the array of sutures have been serially tensioned to close the abdominal wall defect, a series of at least five square knots must be tied on top of each slip knot in each individual suture, and eighty or more knots may need to be tied to complete the repair. Each square knot requires tension to be maintained on one limb of the suture, while a laparoscopic knot pusher is advanced along the other suture limb to push the knot subcutaneously down to the anterior rectus sheath. This process is tedious, as fifty or more knots need to be tied to complete the repair.

Other methods employ an anchor delivery tool wherein a tissue anchor lies within the bore of the needle. As a relatively large diameter needle is required to deliver an anchor because the outer diameter of the needle is larger than the diameter of the anchor, there exists the potential for an anchor under continuous tension to dilate the tract in the muscle formed by needle insertion, leading to pullout of the anchor through the dilated tract. This scenario may be observed particularly in the weakened or attenuated tissue encountered in ventral hernia patients A simple laparoscopic technique and instrumentation is desired to quickly and easily place multiple interrupted fastening loops through the full abdominal wall and around a hernia defect such that the loops may be tensioned without incising, pulling out, or tearing through the muscle tissue.

SUMMARY

The present disclosure is directed to devices and methods for minimally invasive closure of a surgical defect such as a ventral hernia using self-locking straps. These embodiments may provide for fewer surgical steps, reduced complexity, smaller incision sites, reduced pressure on tissue, and easier and faster serial tensioning along the length of a defect. An embodiment of a system according to the present disclosure may include a self-locking strap having a lock-head, a first needle having a lumen for delivering the self-locking strap through a first incision site, a second needle having a hook on its distal end for engaging the self-locking strap and pulling the strap from the body through a second incision site, and a guide having an aperture near its distal end for passing the second needle therethrough and retaining the strap after the second needle is removed from the aperture.

In other embodiments, the guide may be used for tunneling through subcutaneous tissue from the first incision site to a second incision site, and it may have a hook near its distal end for engaging with the self-locking strap and pulling the strap back through the subcutaneous tissue to the first incision site. Furthermore, the second needle may have a hook at its distal end, and it may be capable of passing through the lock-head and engaging with the distal end of the self-locking strap and pulling the distal end of the strap through the lock-head and out of the body.

Embodiments of the system may also include a support tube for pushing on the self-locking strap while the strap is being tensioned, a rotational cutter with at least one distal blade for severing the self-locking strap adjacent to the lock-head, a linear cutter having an inner tube, an outer tube, and a radially flexing blade that depresses into the lumen of the inner tube when engaged by the outer tube. The system further may include a tensioner having at least one movable lock-head to incrementally tension the self-locking strap; the tensioner may have a tension gauge to measure the tension in the strap and an indicator to display the tension in the strap. The tension gauge may be a mechanical spring gauge or a force transducer, and it may be capable of converting the tension force into an electrical signal and transmitting the electrical signal to a display or receiving computer. The system may include a laparoscopic grasper for placing the self-locking strap into engagement with the second needle; the laparoscopic grasper may have a robotic arm interface that is robotically controlled. The self-locking strap may include an attached lock-head capable of receiving a single end of the strap or detached lock-head capable of receiving both ends of the strap. The self-locking strap may have an aperture at its proximal and distal end or a protuberance at its distal end for engaging with the second needle. The strap may also have a plurality of apertures through the strap to facilitate ingrowth of tissue. The first needle may have a slot along its length for removing the self-locking strap, and the guide may have a robotic interface fixed to its distal end.

Embodiments of a method for closing a defect may include positioning a guide beneath the skin between a first incision and a second incision in the body of a patient so that the distal end of the guide resides near the second incision. Inserting a first needle through the first incision, inserting a second needle through the second incision and an aperture in the guide, placing a distal end of a self-locking strap through the first needle and into the body cavity. Next, the surgeon or a robotic arm may engage the second needle with the distal end of the strap and pull the second needle through the guide and out of the body leaving the strap captured by the aperture in the guide. The strap may be released from the first needle, and the guide pulled out of the body through the first incision so that the distal end of the self-locking strap exits the first incision with the guide. To lock the strap, the surgeon may place a lock-head over the distal end of the self-locking strap and advancing the lock head down the self-locking strap to tighten the self-locking strap around a defect.

In other embodiments, the method may include inserting a first needle through a first incision and into a body cavity on a first side of a defect, placing the distal end of a self-locking strap through the first needle and into the body cavity, retracting the first needle from the body, and removing the first needle from the strap while leaving the strap inside of the body. Next, the surgeon or a robotic arm may place a guide through a second incision site on the opposite side of the defect and advance the guide subcutaneously to the first incision site, engaging the proximal end of the strap with the guide and pulling the proximal end of the strap subcutaneously across the defect to the second incision site. The second needle may be placed through a lock-head attached to the proximal end of the strap and advanced into the body cavity to engage the distal end of the strap. The second needle may be used to pull the distal end of the strap out through muscle tissue and through the lock-head. Finally, the strap may be tightened to close the defect.

In other embodiments, initially, pilot needles may be placed through the skin and muscle tissue to determine the correct distance lateral to the defect for inserting surgical instruments. Furthermore, a laparoscopic grasper, which may be robotically controlled, may be used to engage the second needle with the distal end of the strap. The first needle may include a hook at its distal end for engaging with the self-locking strap, and the first needle may have a slot through which to withdraw the self-locking strap laterally from the needle. A support tube may be placed over the self-locking strap such that the surgeon may pull the self-locking strap while pushing the support tube to tighten the self-locking strap. Next, the surgeon may tighten the self-locking strap with a tensioner that has at least one lock-head to incrementally tighten the self-locking strap. The tensioner may have a tension gauge that may be a mechanical spring gauge or a force transducer to measure the tension in the strap and to display the tension force, and the force signal may be converted into an electrical signal that may be transmitted to a display or receiving computer. The excess amount of self-locking strap may be cut inside of the body adjacent to the lock-head. In some embodiments, the strap may include a plurality of apertures through the strap to facilitate ingrowth of tissue.

In another embodiment, a tensioner for tightening a self-locking strap may include a shaft, a plunger slidably disposed on the shaft, a stationary lock-head distal to the plunger and affixed to the shaft, and a movable lock-head affixed to the plunger and aligned with the first stationary shaft so that a strap may pass through both lock-heads. The tensioner may also include a frame slidably attached to the shaft and located distal to the stationary lock-head and a compression spring compressed between the frame and the stationary lock-head. An elongate tube may extend distally from the frame such that the tube abuts against the lock-head of a self-locking strap inside of a human body.

The strap tensioner may also include a force transducer configured to read the amount of force on a strap that is held by the stationary lock as the elongate tube abuts against the lock-head of the strap. The tensioner may also include a set of force markings located on the distal portion of the shaft configured to read the amount of force on a strap that is held by the stationary lock.

In an embodiment, a self-locking strap having teeth on both sides may be provided. The strap may include an elongate body having a distal end, a proximal end, a top side and a bottom side, a first set of ramped teeth on the top side, and second set of ramped teeth on the top side having a ramp direction in the opposite direction to the first set of teeth. The bottom side may have a third set of ramped teeth having a ramp direction in the same direction as the first set of teeth and a fourth set of ramped teeth on the bottom side having a ramp direction in the same direction as the second set of teeth. The strap may have a detached lock-head having an aperture capable of passing the distal end and proximal end simultaneously and opposing pawls protruding into the aperture for engaging with the distal end and the proximal end. The third set of ramped teeth may be offset longitudinally from the first set of ramped teeth, and the fourth set of ramped teeth are offset longitudinally from the second set of ramped teeth to provide a wider minimum cross-sectional thickness for the strap. In embodiments, the strap may have a plurality of apertures through the strap to facilitate tissue ingrowth and proximal ends that are tapered with an aperture therethrough to engage with a surgical instrument.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 2A-2J illustrate various views of embodiments of self-locking straps.

FIGS. 15A-15E show various embodiments of a releasable strap lock-head.

FIGS. 20A-20I illustrate another embodiment of a system used to close a defect.

DETAILED DESCRIPTION

A description of example embodiments of the invention follows.

Systems and methods for closing a tissue defect are described herein. While the present disclosure describes the system and method in the context of hernia repair, and in particular ventral hernia repair, the devices and methods presently disclosed may be used in any surgical procedure for joining tissue, closing a tissue opening, or fastening a device to or between two or more sections of tissue.

In the patient's midline, the left and right anterior and posterior rectus sheaths come together to form a single layer called the linea alba. A ventral hernia defect may arise as an opening in this layer. It may also be an opening that extends through the posterior rectus sheath, rectus muscle, and anterior rectus sheath; or it may be an opening in the fascia lateral to the rectus muscle. While the current disclosure describes systems and methods in the context of laparoscopic surgery, the systems and methods may be applied to any other class of procedure such as laparotomy, or robotic surgery.

Figure 1:
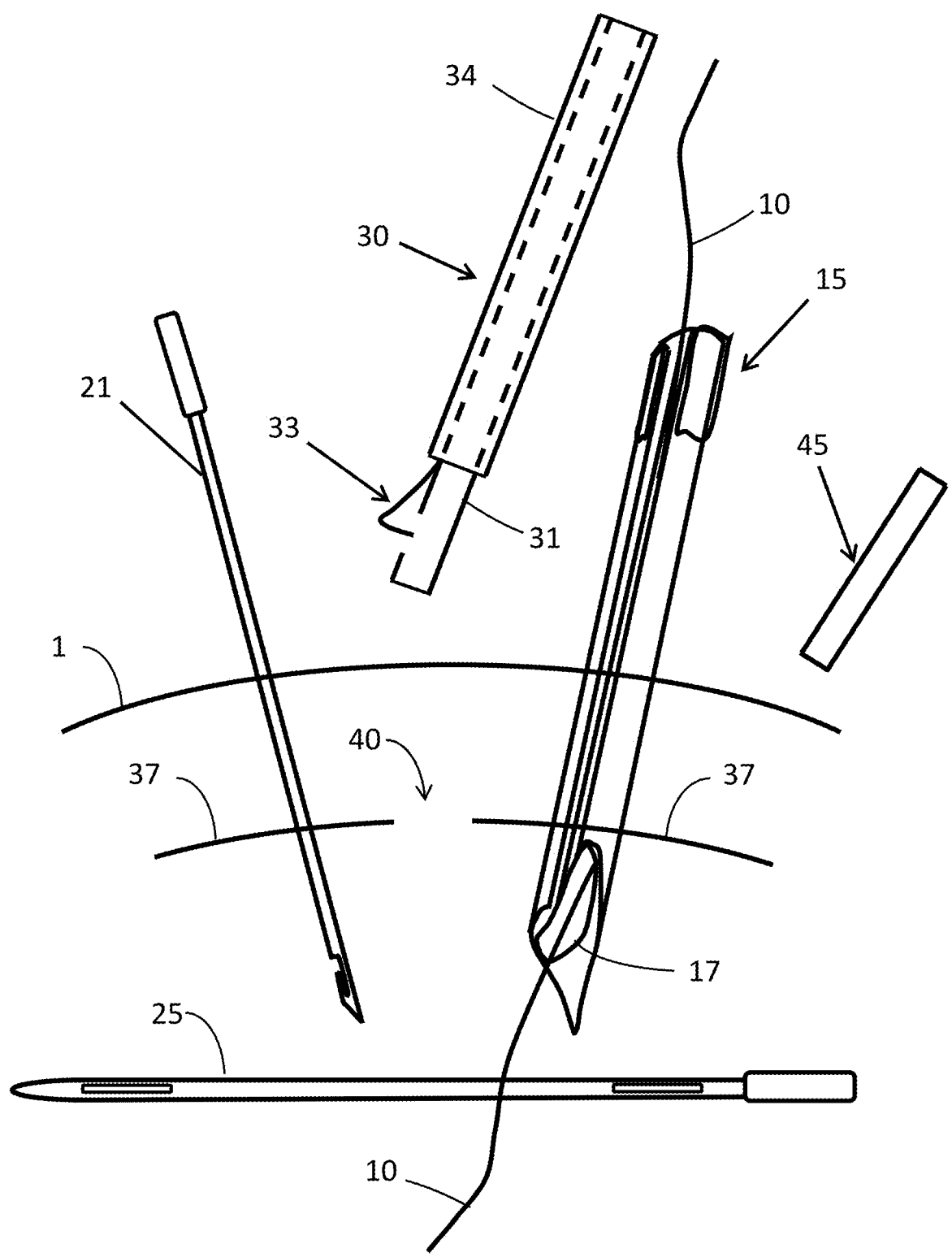
FIG. 1 depicts a system for closing a defect in tissue.

With reference to FIG. 1, one embodiment of a system 1 for closing a fascial opening 40 (e.g., ventral hernia) is shown in relation to a layer of skin 1 and a defect 40 shown in reference to the anterior rectus sheath 37. The system may be used to deliver an implant to constrain tissue, such as a suture or strap through minimally invasive or laparoscopic surgery. The system 1 may comprise by way of non-limiting example, a self-locking strap 10, a slotted needle 15, a hook needle 21, a subcutaneous guide 25, a tubular cutter 30, and a support tube 45. An inner tube 17 may reside inside of the slotted needle 15. The tubular cutter 30 may be comprised of an outer tube 34 and an inner tube 31 having a cutting blade 33 attached therein. The aforementioned components are described in further detail in this disclosure. Other components and devices, including those disclosed throughout this application, may be included in the systems and used in the methods disclosed herein, i.e., the system 1 shown is not necessarily a complete surgical kit and other devices and methods may be substituted or added to the system 1 to form other systems or embodiments that are within the scope of the invention(s) disclosed herein. For example, various laparoscopic instruments, such as a laparoscope with a camera may also be-be used during the surgery.

This application discloses methods, systems, and devices that involve placing a strap around a defect to close a tissue defect. In general, a strap may be wider than a suture and have a flatter shape so as to place less pressure on the tissue and reduce the risk of cutting into the tissue as the tension forces required to approximate muscle tissue may be high. In this application, the straps are referred to as "self-locking straps" which means that when the strap is pulled through its "lock-head" and released, it tends to stay at the same position without retracting back through the lock-head. Self-locking straps use a mechanism such that when the strap is pulled through the lock-head, it will not slide back through the lock-head. That is, the strap may be drawn through the lock-head in one direction, but a reversal of movement of the strap within the lock-head is mechanically restricted so as to effect a locking position in one-way fashion. There are many types mechanisms that perform this function such as cable tie mechanisms (also known as zip ties), ratchets, cam locks, and ratchet and pawl mechanisms. Some designs have features on the strap, such as teeth, that interact with features in the lock-head, such as a pawl which flexes or is otherwise spring biased to engage with the features on the strap. The strap may have holes or slots into which a spring-loaded pawl feature engages. Other designs may have a smooth strap that is gripped by cam-like features, tines, or barbs which grasp the strap predominantly in one direction to prevent it from regressing through the lock-head. Some self-locking straps may have an integrated lock-head positioned, for example, near an end of the strap while others may have a detached head that may be placed on the strap for locking. Such self-locking straps and variations thereof are within the scope of this disclosure.

The use of self-locking straps in ventral hernia procedures simplifies the procedure and saves time because the surgeon does not need to tie numerous suture knots or clamp and re-clamp partially tightened sutures or worry about the self-locking straps loosening. The self-locking functionality of the straps disclosed herein permits the surgeon to quickly and easily tension individual straps serially to close a defect incrementally without tying permanent knots or releasable knots. This is because the surgeon may pull one or both ends of the strap through the lock-head and at any time let go of the strap and it will hold the tension due to the ratchet effect of the strap features engaging with the lock-head. Thus, the surgeon can move on to other aspects of the surgical procedure, for example, incrementally tightening other straps along a defect without having to clamp or knot them to prevent slipping.

For brevity, several self-locking strap embodiments are disclosed in this application. However, other types of self-locking straps are within the scope of the invention(s) described herein.

The self-locking strap should be sized such that it has the strength to approximate and hold the muscle tissue while being flexible enough for manipulation through the body and the instruments. The self-locking straps referred to in this application may be made of any biocompatible material that may be implanted into the body. Candidate materials include, by way of nonlimiting example, polymers such as PEEK, polypropylene, or Nylon, or metals such as Nitinol or stainless steel.

FIG. 2A depicts an embodiment of a self-locking strap 10 which may be made of a biocompatible material suitable for implanting into a human or mammalian body. The self-locking strap 10 may comprise a distal end 11 and a proximal end 13 and, as mentioned above, it may be made of a polymeric material such as polypropylene, PEEK, or Nylon, or for example, a metallic material such as Nitinol or stainless steel. The diameter of the self-locking strap 10 may be of any size that provides enough tensile strength to approximate and hold tissue together, for example in ventral hernia repair. In one embodiment, the self-locking strap 10 may be made of polypropylene, and it may be between 0.25 mm and 2 mm in diameter or, for example, approximately 0.35 mm in diameter, and it may be approximately 100 cm in length or any length that is appropriate for the size of the patient. In another embodiment, the self-locking strap 10 may be made of stainless steel, and it may be approximately 0.10 mm to 0.25 mm in diameter and approximately 100 cm in length. A protuberance 12 or other grasping feature may be permanently formed or attached near the distal end of the self-locking strap 10, and it may be made of the same material as the self-locking strap 10, or it may be composed of a different polymeric or metallic material. The protuberance 12 may be larger than the strap diameter, or approximately 0.5 mm to 0.75 mm in diameter and shaped, for example, spherically or in any other shape that allows it to be retained by a hook needle 21 or other grasper described elsewhere in this disclosure. In other embodiments, the protuberance 12 may be a loop or aperture formed in the distal end 11 of the self-locking strap 10 to facilitate grasping of the self-locking strap 10.

The self-locking strap 10 comprises a distal end 11 at one end and a proximal end 13 at the opposite end. The self-locking strap 10 may have teeth 50 arranged along the strap to facilitate locking into a lock-head that may be attached to one end of the self-locking strap 10. The teeth 50 may be located on the entirety of the self-locking strap, or on a portion thereof, or in some embodiments the entire strap may be smooth. By way of non-limiting example, in FIG. 2A, an embodiment of the self-locking strap 10 is shown with teeth 50 on the portion of the strap towards the proximal end 13. The self-locking strap 10 may be composed of a single polymeric or metallic material such that the smooth end (distal end 11) and the toothed end (proximal end 13) are made as one component, for example via extrusion or injection molding for polymeric materials. Each tooth 50 may have a major outer diameter of from 1 mm to 3 mm or approximately 2 mm. The teeth 50 may be of any shape that allows them to engage with the lock-head 14 to restrict motion in one-way through the lock-head 14. For example, in some embodiments, the teeth 50 may be shaped like an ellipse, square, sphere, cone, wedge, step, tooth, or hemisphere. The term "diameter" used herein refers to the major, or largest dimension, across the tooth 50. The length of the self-locking strap 10 may be approximately 100 cm or any length that allows it to extend beyond multiple layers of abdominal tissue taking into account the large variation in anatomy due to, for example, variations in adipose tissue.

The self-locking strap 10 is shown in an example of operation in FIG. 2B. A sectional view is shown in FIG. 2C to illustrate how the teeth 50 may interact with the lock-head 14. The lock-head 14 may be attached to the proximal end 13 of the self-locking strap 10 and comprises locking features such as one or more pawls 51 that engage with the teeth 50. The pawls 51 may be two dimensional, that is like a beam, or they may comprise a conical shape (axisymmetrical), and they may be segmented to allow the pawls 51 to deform to pass teeth 50 while flexing back down behind a tooth 50 to lock it from passing back through the lock-head 14. As shown in FIG. 2C, due to the angled orientation of the pawls 51, the tooth 50, which is of a triangular or conical shape in this embodiment is constrained to only pass in the direction of the arrow 48 as the pawls 51 flex around the tooth 50 and close behind it as the proximal end 13 is pulled through the lock-head 14. This operation is one example of a one-way lock and one skilled in the art will recognize the examples and embodiments described herein are for illustrative purposes only and that various modifications or changes in light thereof will be suggested to persons skilled in the art and are to be included within the spirit and purview of this application and scope of the appended claims. The pawls 51 of the lock-head 14 may be constructed of a polymeric material such as polypropylene, PEEK, or Nylon, or it may be metal, such as stainless steel. The lock-head 14 may be integrally formed with the proximal end 13 via, for example, injection molding, or it may be a detached element. In further embodiments, the lock-head 14 may be a single ratchet pawl such as that used in zip ties or cable ties designed allow passage of a strap in one direction while locking it from motion in the opposite direction as described elsewhere in this disclosure.

Alternatively, the flexible members (i.e., beams or pawls) may be located on the strap, while the lock-head may have a substantially fixed interface, still resulting in one-way locking action. Example embodiments of alternative locking features are shown in FIGS. 2D-2H. A toothed strap 60 with a spherical tooth 61 is shown in FIG. 2D, a toothed strap 62 with a hemispherical tooth 63 is shown in FIG. 2E, and a toothed strap 64 with a conical tooth 65 is shown in FIG. 2F. The strap need not be axisymmetric, as FIGS. 2G and 2H illustrate flat strap embodiments shown in a side view. In FIG. 2G, the toothed strap 66 is flat and has half-arced teeth 67, and a toothed strap 68 that is flat and has ramped teeth 69 is shown in FIG. 2H. It may be desirable to have apertures through the self-locking strap to facilitate ingrowth of tissue into and through the strap so that the strap is more adherent to tissue along its entire length and it will be less likely to cut through the abdominal wall and cause dehiscence, and a ventral hernia. The apertures may be small holes through the thickness of the strap that are distributed along the length. For example, FIG. 2I shows a section of a self-locking strap 232 having ramped teeth 233 and a series of holes 234 perforating through the strap. In other embodiments, the apertures may be the actual locking features as shown in FIG. 2J. The section of self-locking strap 235 has slots 236 through the strap which may facilitate ingrowth, and they may also be used for locking if the lock-head has, for example, mating tabs that protrude into the slots 236 as the tabs are biased by beam-like flexing or are otherwise spring loaded.

Figure 3A:
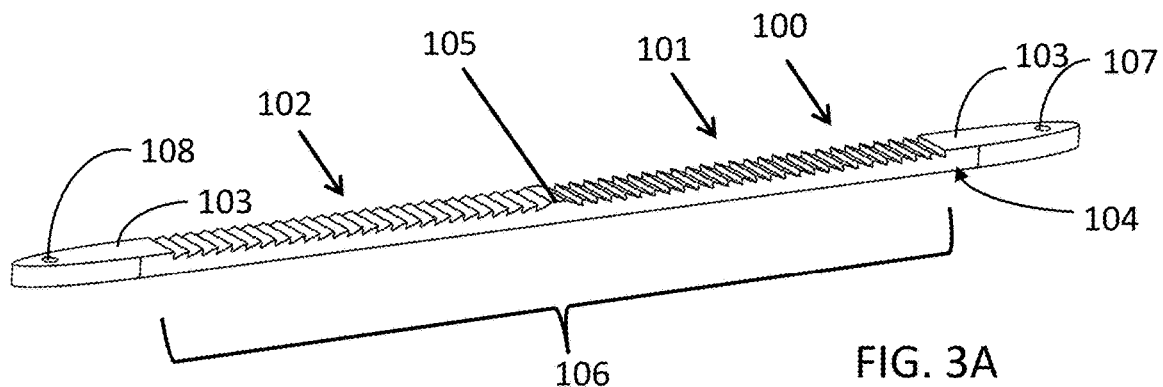
FIGS. 3A-3G illustrate various views of other embodiments of self-locking straps.

Now with reference to FIGS. 3A-3D, which illustrate another embodiment of a self-locking strap 100 that may have a reduced maximal width because the lock-head is separate. For example, FIG. 3A shows the self-locking strap 100 having an elongate body 106 and a substantially flat cross-sectional profile with proximal teeth 101 and distal teeth 102 located on a top side 103 of the self-locking strap 100. The two sets of teeth, the proximal teeth 101 and distal teeth 102, are oriented opposite to each other, that is, they are angled to lock in the opposite direction when the strap is positioned straight as shown. However, when the strap is configured in a loop, the teeth 101 and 102 will be oriented in the same direction. Both sets of teeth 101 and 102 of the strap may emanate from a central point 105 of the strap 100 which may be at the center of the strap 100 or may be offset from the center and the teeth 101 and 102 may be offset from the central point 105, although in the figures the sets of teeth emanate from adjacent to the central point 105, that is, the teeth are arranged symmetrically about the center of the strap. This self-locking strap embodiment has a detached lock-head as further described below. Since the lock-head may typically be larger in diameter than the underlying strap, the self-locking strap 100 may fit into a needle with a smaller lumen while the lock-head is detached.

Figure 3B:
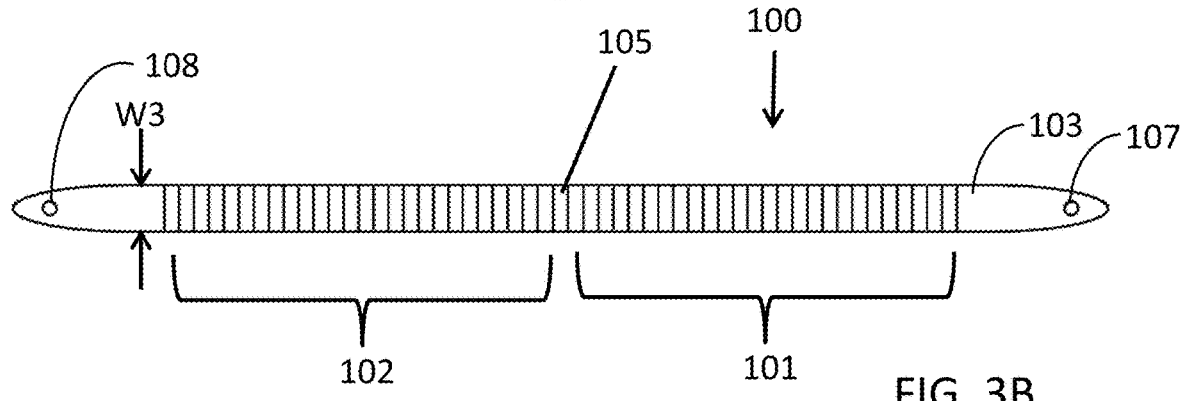

FIG. 3B shows a top view of the self-locking strap 100 with proximal teeth 101 and distal teeth 102 spaced about the central point 105. Apertures 107 and 108 may be located at one or both ends of the self-locking strap and may be of any shape or size that can be engaged with a surgical grasper or a hook needle (not shown) within the body as described below. The width w3 of the strap 100 may be small enough so that the strap 100 can fit into a small gage needle to facilitate a minimally invasive surgical procedure. For example, a strap insertion needle 7 (see FIG. 18C) may have an 11 gauge (3 mm) outer diameter and a lumen diameter of approximately 2.4 mm. Therefore a strap of about 1.7 mm to 2.0 mm in width or smaller may be passed through the lumen.

Figure 3C:
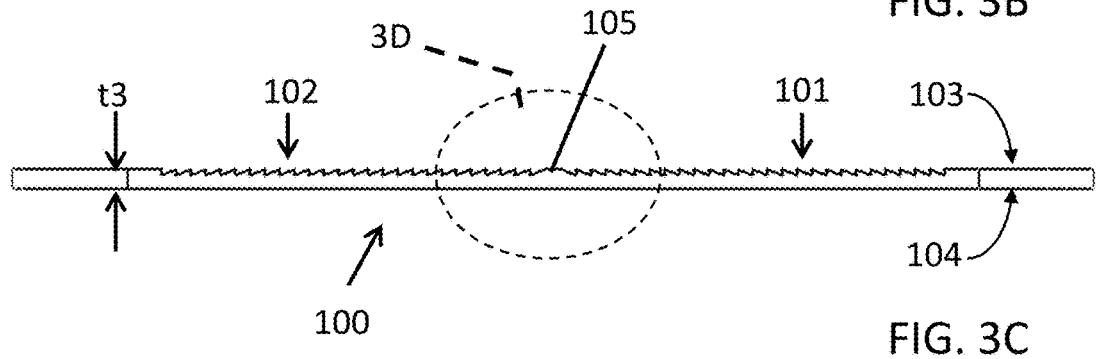

FIG. 3C shows a side view of the self-locking strap 100. As with the other strap embodiments disclosed herein, the overall thickness t3 of the strap should be large enough that the strap will withstand the tensile force required to approximate the tissue in a given type of procedure while remaining flexible enough to form a loop to tighten around the anatomy. For reference, in open abdominal closure procedures, a suture with a tensile strength of 10 lbs is typically used. The self-locking strap 100 may also have swaged or flattened ends to facilitate handling within the body and to provide a flexible section for maneuvering the self-locking strap 100 within the body and into the lumen of a needle. The minimum thickness of the strap t$3m$ is illustrated in the detail view shown in FIG. 3D which shows the central point 105 and the proximal teeth 101 and distal teeth 102 on either side. This minimum thickness t$3m$ affects the overall stiffness and strength of the strap and hence the tooth depth should be shallow enough so that the minimum thickness t$3m$ is thick enough to provide enough tensile strength required for a given procedure, yet deep enough to engage with a pawl type feature in the locking head without slipping under tensile loading. The self-locking strap 100 may be made of a biocompatible material such as such as a polymer (e.g., polypropylene, PEEK, or Nylon), or a metallic material such as Nitinol or stainless steel.

Figure 3D:
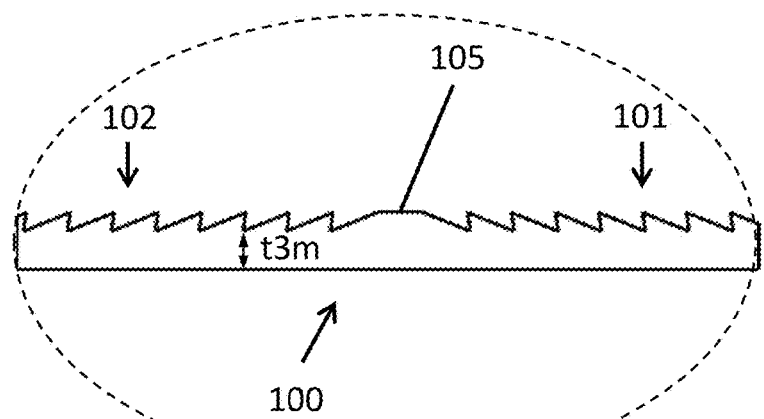

As shown in FIG. 3D, the proximal teeth 101 ramp down toward the proximal section of the strap, while the distal teeth 102 ramp in the opposite direction, down toward the distal end of the strap. An example of the operation is illustrated in FIGS. 3E-3G.

Figure 3E:
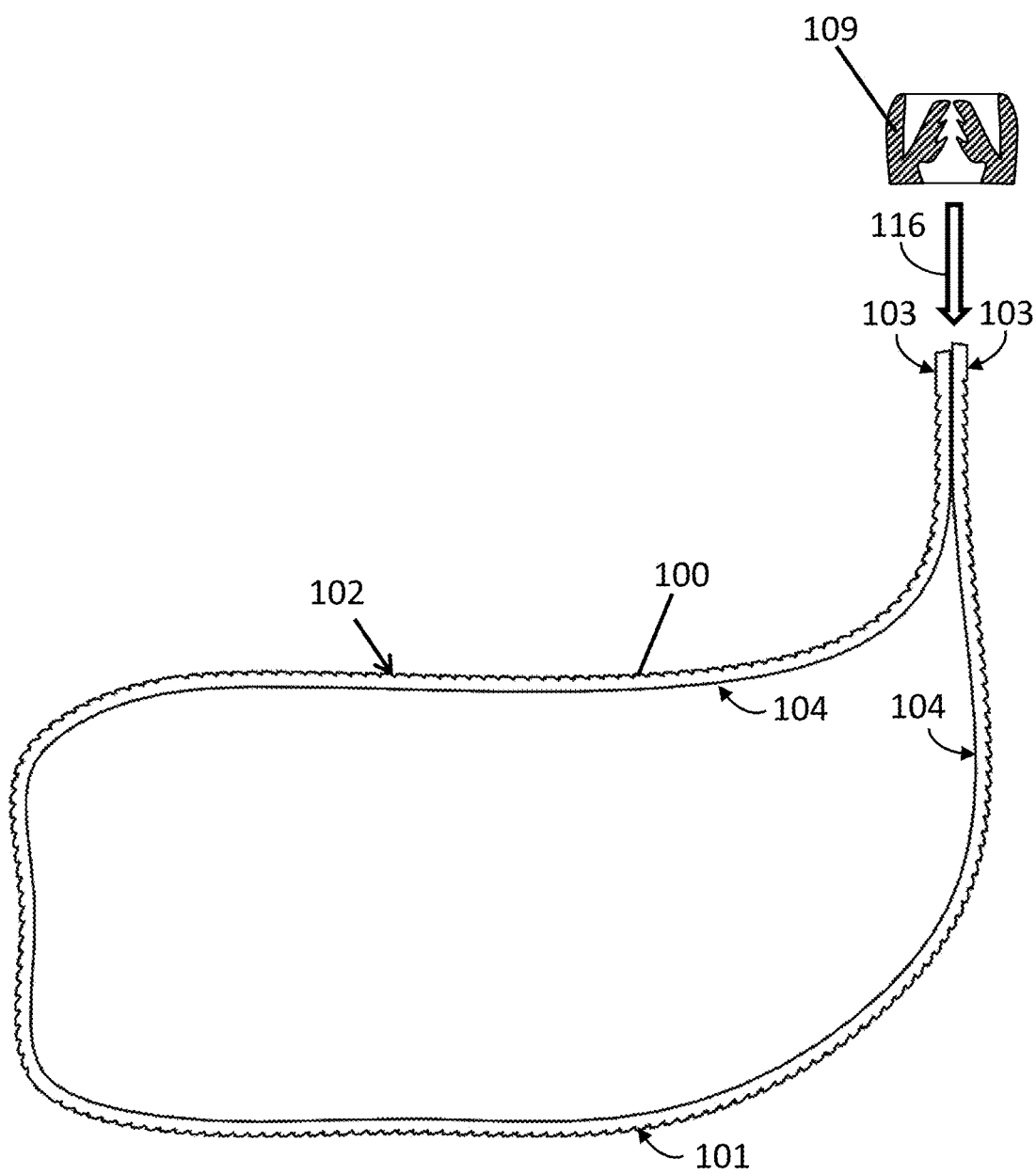
Figure 3F:
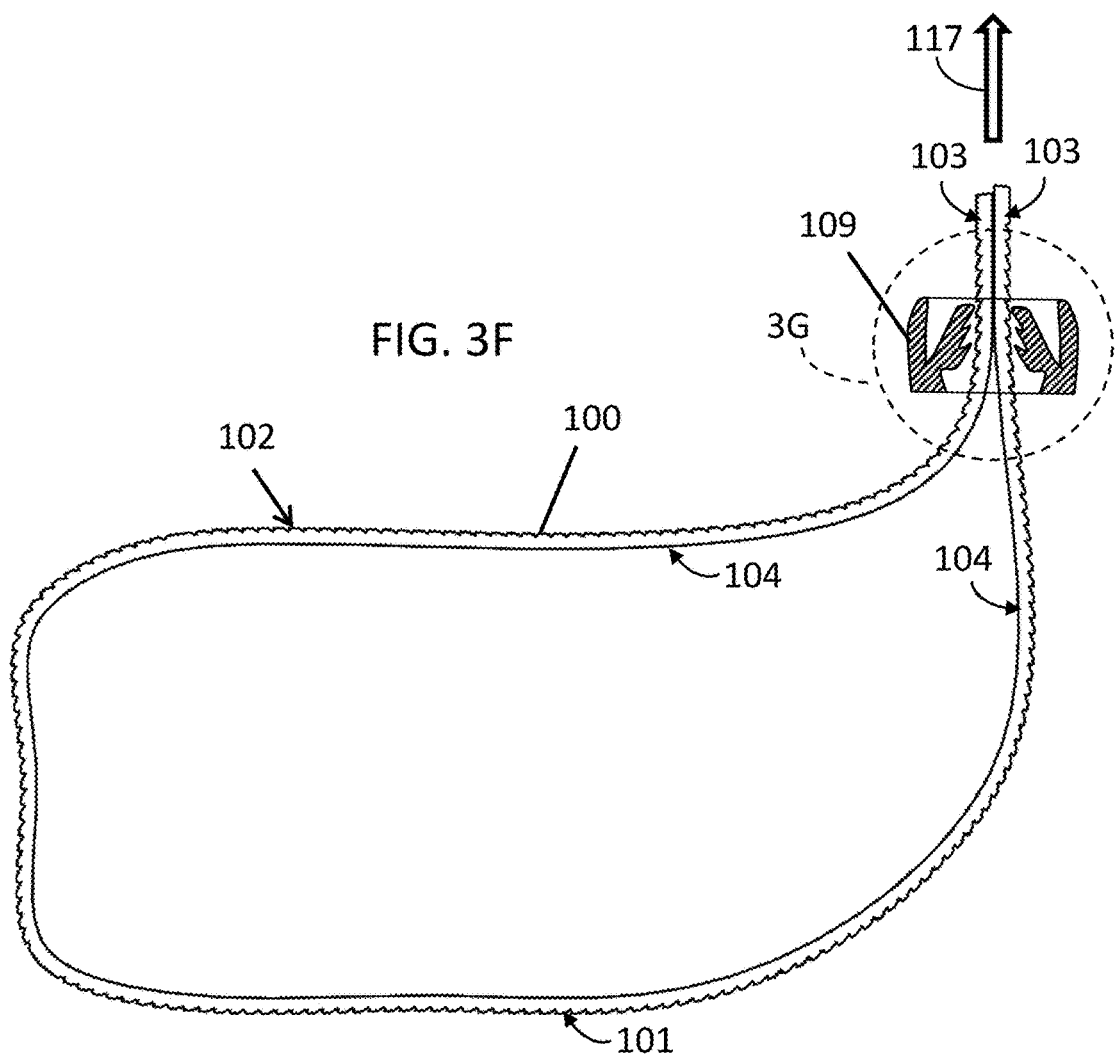
Figure 3G:
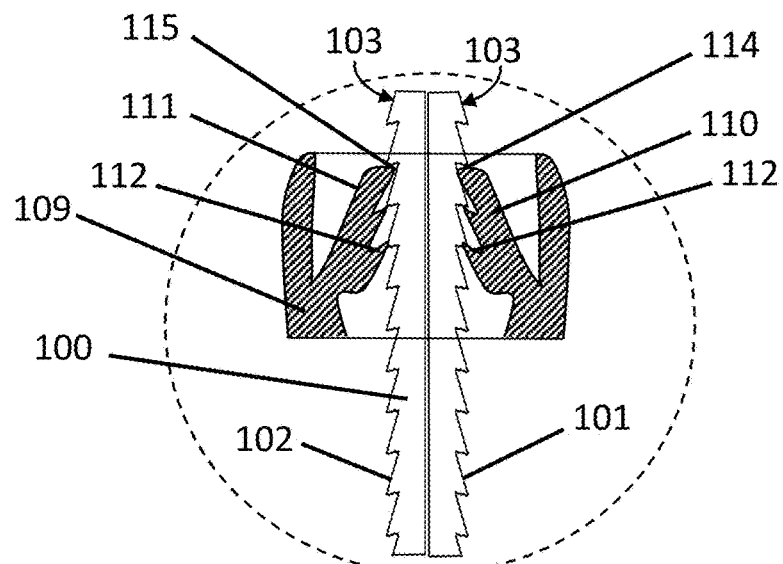

With reference to FIG. 3E, the self-locking strap 100 is shown in a looped configuration as it may be wrapped around tissue (not shown) inside the body. The self-locking strap 100 is folded such that the bottom side 104 is inside of the loop as it would be in contact with the body; at the ends, the bottom side 104 contacts itself while the top side 103 faces outward leaving the proximal and distal ends of the strap adjacent. A lock-head 109, which is shown in a sectional view to illustrate the function, engages with both ends of the self-locking strap 100 as it is advanced in the direction of the arrow 116. As shown in FIG. 3F, both ends of the self-locking strap 100 may be pulled through the lock-head 109 in the direction of the arrow 117 simultaneously. This self-locking mechanism is shown in the detail view of FIG. 3G. The lock-head may have a plurality of pawls 110 and 111 that flex open to allow passage of the self-locking strap 100, and then close to engage with the proximal teeth 101 and the distal teeth 102 respectively to prevent the self-locking strap 100 from moving back through the lock-head 109, that is, opposite to the direction of the arrow 117 in FIG. 3F. The pawls 110 and 111 may have one or more teeth 112 to facilitate gripping the self-locking strap 100, or the pawls 110 and 111 may have any other surface features that may facilitate gripping with the self-locking strap 100 such as serrations or surface roughness. Alternatively, the pawls 110 and 111 may be smooth, relying on the leading edges 114 and 115 of the pawls 110 and 111 respectively to lock onto proximal and distal teeth 101 and 102 on the self-locking strap 100 such as in a typical cable tie.

Yet another embodiment is shown in FIGS. 4A-4E. A self-locking strap 120 is shown having an elongate body 126 and a substantially flat cross-sectional profile with proximal teeth 121 and distal teeth 122 located on a top side 123 of the self-locking strap 120. Similar to the previously disclosed self-locking strap 100, the top side 123 of the self-locking strap 120 has two sets of teeth, the proximal teeth 121 at the proximal end 118 and distal teeth 122 at the distal end 119, which are oriented opposite to each other about a central point 125, that is, they are angled to lock in the opposite direction when the strap is straight as shown. However, the present self-locking strap 120 has teeth on both sides of the strap—the top side 123 and the bottom side 124. That is, the bottom side has bottom side proximal teeth 131 and bottom side distal teeth 132 arranged in opposing fashion like the teeth on the top side 123. This two-sided tooth arrangement allows the self-locking strap 120 to lock into a lock-head even if the strap is twisted as it winds through the body.

Figure 4A:
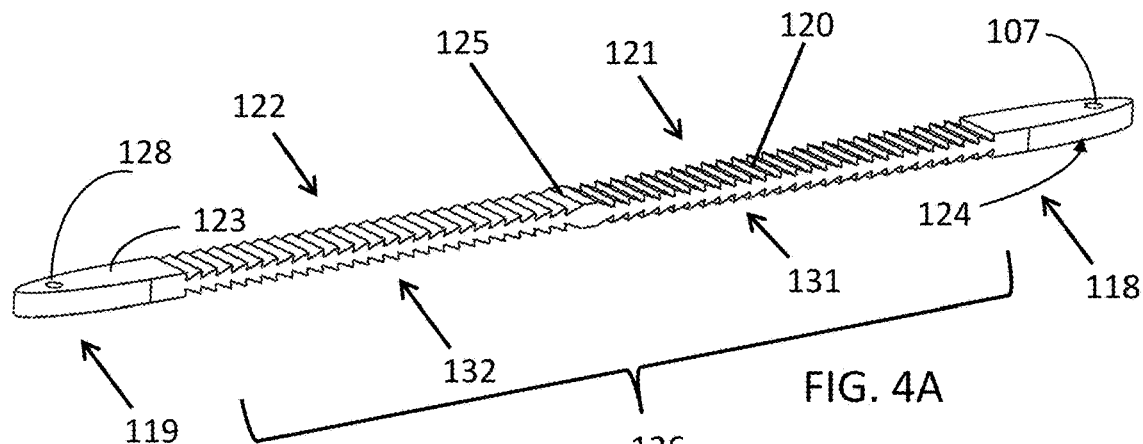
FIGS. 4A-4E illustrate various views of other embodiments of self-locking straps.
Figure 4B:
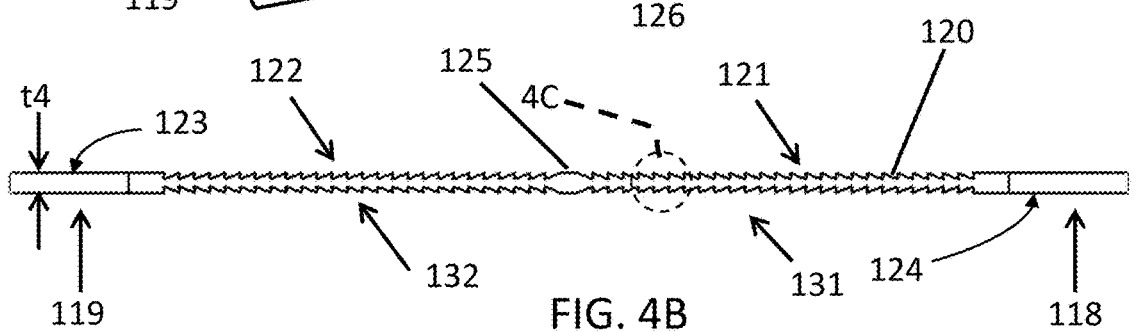
Figure 4C:
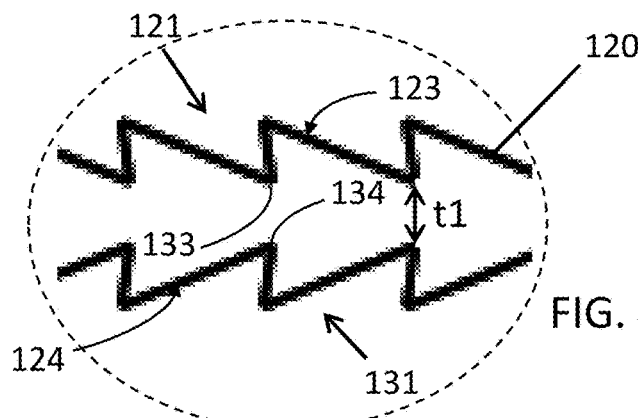

FIG. 4B is a side view of the self-locking strap 120. The overall thickness t4 of the strap should be large enough that the strap will withstand the tensile force required to approximate tissue during and after a procedure yet be flexible enough to form a loop and be capable of being tightened around the anatomy. The self-locking strap 120 may have tapered ends as shown and the thickness t4 may also be swaged or flattened (not shown) at the ends to facilitate handling within the body and to provide a flexible section for maneuvering the self-locking strap 120 within the body and into the lumen of a needle. The minimum thickness t1 is illustrated in the detail view shown in FIG. 4C, which is a side view illustrating the proximal teeth 121 on the top side 123 and the bottom side proximal teeth 131 on the bottom side 124. In the configuration shown, both sides of teeth are aligned, in that the root and tip of each tooth on the top side 123 mirrors that on the bottom side 124. As such, the minimum thickness t1, which affects the overall stiffness and strength of the strap, is dictated by the distance t1 between the upper tooth inner edge 133 and lower tooth inner edge 134 as shown by t1.

Figure 4D:
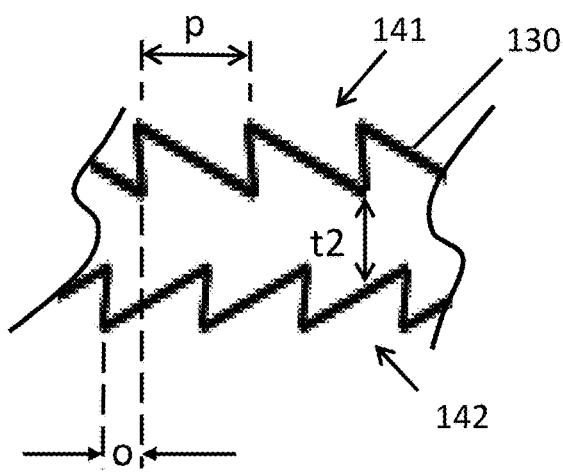

In another embodiment, the teeth may be staggered to increase the distance t1, thus providing more cross-sectional area which may increase the strength of the strap. This arrangement is illustrated in FIG. 4D which is a view of a section of another self-locking strap 130 in a detail view analogous to that shown in FIG. 4C, however in this embodiment the proximal teeth 141 are offset by a distance o from the bottom side proximal teeth 142, where o is less than p, the pitch distance between teeth. Staggering the teeth in this manner increases the minimum distance between teeth to t2, providing an effectively thicker strap where t2 is greater than t1 for a given strap thickness and tooth profile.

Figure 4E:
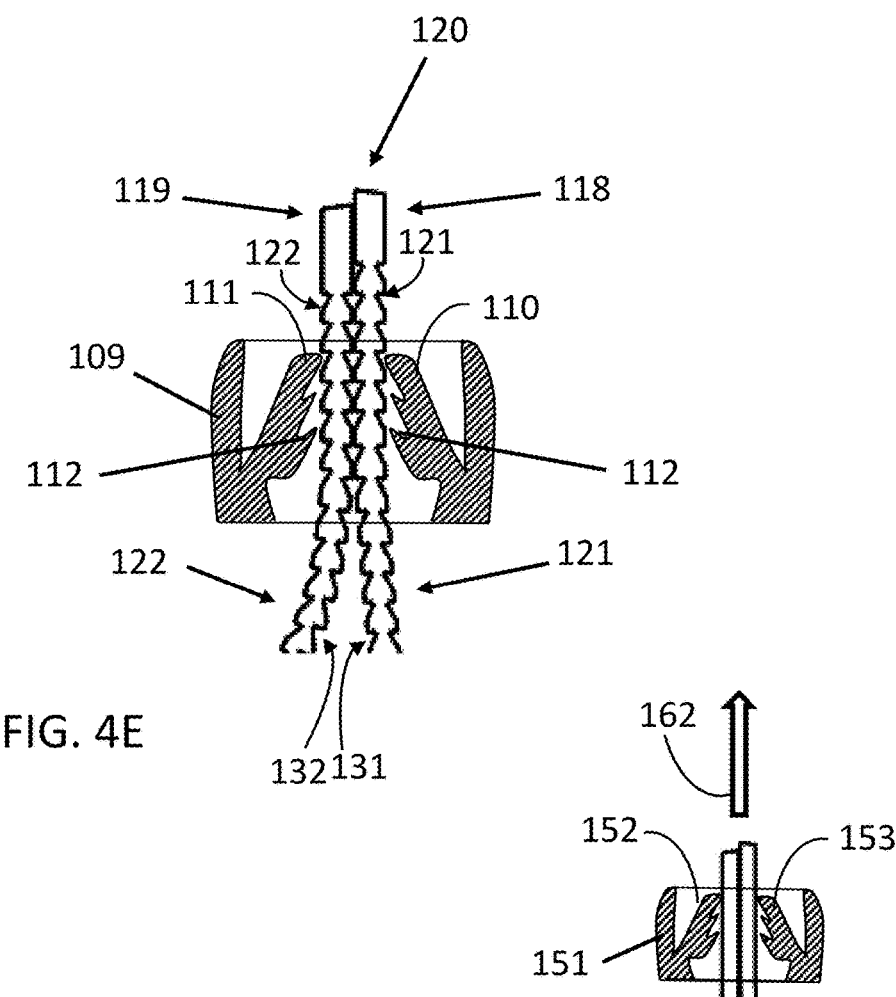

FIG. 4E illustrates the self-locking strap 120 in operation with the lock-head 109 in a sectional view to illustrate the one-way lock engagement. Analogous to the previously described embodiment, the self-locking strap 120 is shown passing through the lock-head 109. The lock-head may have a plurality of pawls 110 and 111 that flex open to allow strap passage, and close to engage with the proximal teeth 121 and the distal teeth 122 respectively to prevent the strap 120 from moving back through the lock-head 109. If the distal end 119 of the strap 120 happened to be rotated (not shown) as the strap transits through the body, the bottom side distal teeth 132 would engage with the pawl 111 of the lock-head 109. The pawls 110 and 111 may have one or more teeth 112 or grip features to facilitate gripping the self-locking strap 120 or any other surface features to facilitate holding the self-locking strap 120. Alternatively, the pawls 110 and 111 may be smooth, relying on their leading edges to lock onto proximal and distal teeth 101 and 102 on the strap like a standard cable tie.

Figure 5A:
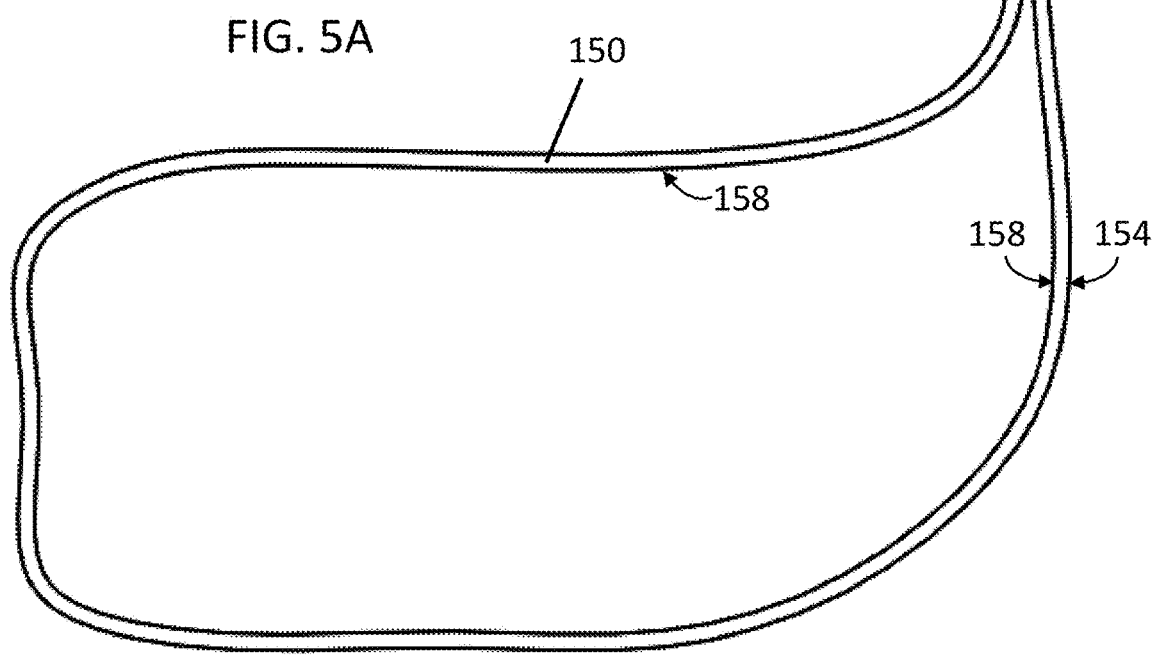
FIGS. 5A-5B show various views of other embodiments of self-locking straps.
Figure 5B:
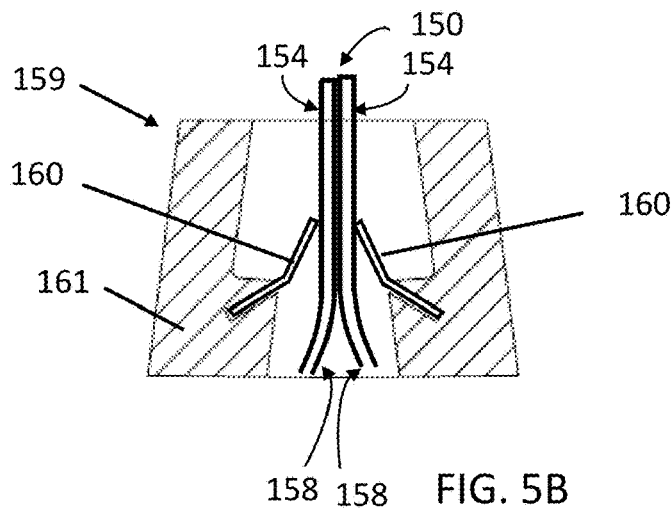

In some embodiments, the self-locking strap may have a smooth surface; FIG. 5A shows an embodiment of a self-locking strap 150 without teeth inserted through a lock-head 151 which is shown in a side section view. The self-locking strap 150 may have a top surface 154 that is relatively smooth and a bottom surface 158 that is relatively smooth, that is the self-locking strap 150 may be flat or round in cross-section, and it may lock in the lock-head 151 even if the strap 150 is twisted since both the bottom surface 158 and the top surface 154 are configured to engage with the lock-head 151. That is, if the self-locking strap 150 is twisted as it transits through the body, it will still lock as shown in FIG. 5A because both sides of the strap engage with the lock-head 151 in the same way. The surface of the self-locking strap 150 may not be entirely smooth, as it may have a level of surface texture or roughness to facilitate gripping in the lock-head 151. The texture may be small gratings, random bumps, texture, or a general grit or surface roughness that can be imparted to the strap, for example, through injection molding. The lock-head 151 may have a set of pawls 152 and 153 that elastically flex to open to accept the strap 150, and then tend to close, putting pressure onto the strap 150 and digging into the top surface 154 and bottom surface 158 so as to prevent the strap 150 from travelling back through the lock-head 151, that is, in the direction opposite the arrow 162. The pawls 152 and 153 may also be referred to as tines, beams, or barbs by one skilled in the art. In FIG. 5B, the self-locking strap 150 is shown protruding through another embodiment of a lock-head 159 having barbs 160 that impinge on the strap 150 to dig into the top surface 154 of the strap 150 such that the strap 150 may only travel in one direction. In embodiments, the barbs 160 may be made of a metal such as stainless steel while the body 161 of the lock-head may be made of a plastic, rubber, or elastomeric material; the barbs 160 may be insert molded into the body 161 or bonded therein or molded as part of the lock-head in one piece.

Another type of detached lock-head embodiment is a crimp (not shown). That is, a malleable lock-head may be slid down the two ends of the strap, similar to the approach shown in FIG. 5A, and then crimped in place by a tool such as pliers. The crimp design does not inherently create a one-way lock, but the crimp could, for example, be partially closed until final tightening, then crimped fully.

The self-locking strap 150 may be made of a biocompatible material such as such as a polymer (e.g., polypropylene, PEEK, or Nylon) or a metallic material such as stainless steel. Additionally, since the self-locking strap may remain within the body after surgery, they may be made of a bioabsorbable material that is absorbed or disintegrates over time.

Figure 6A:
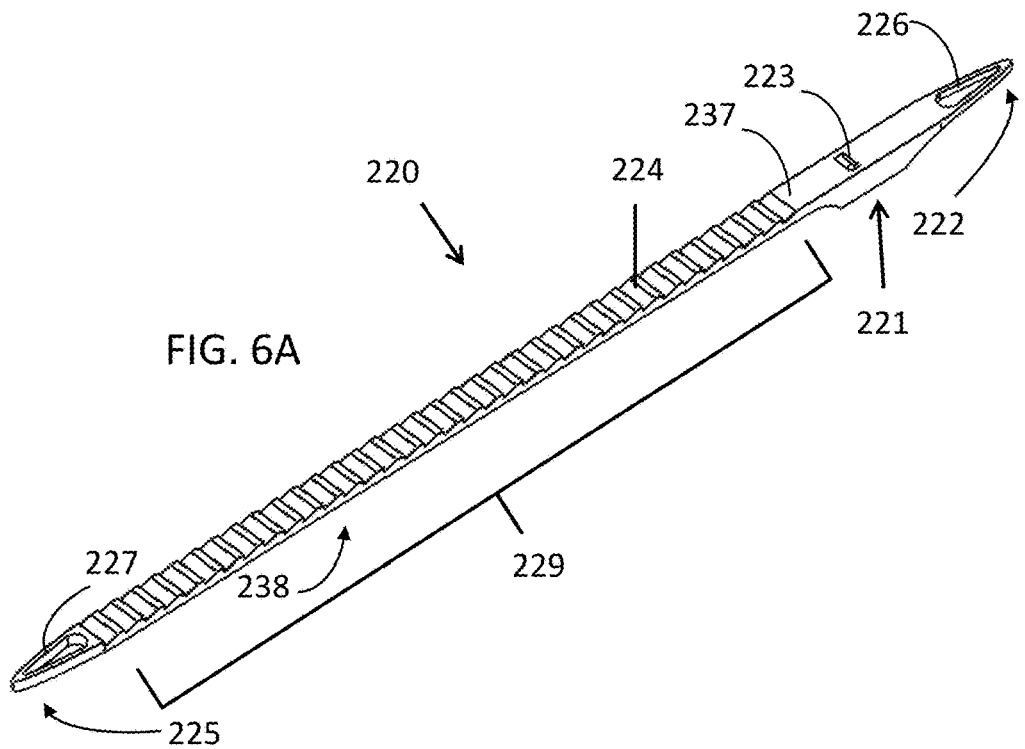
FIGS. 6A-6B show various views of another embodiment of a self-locking strap.
Figure 6B:
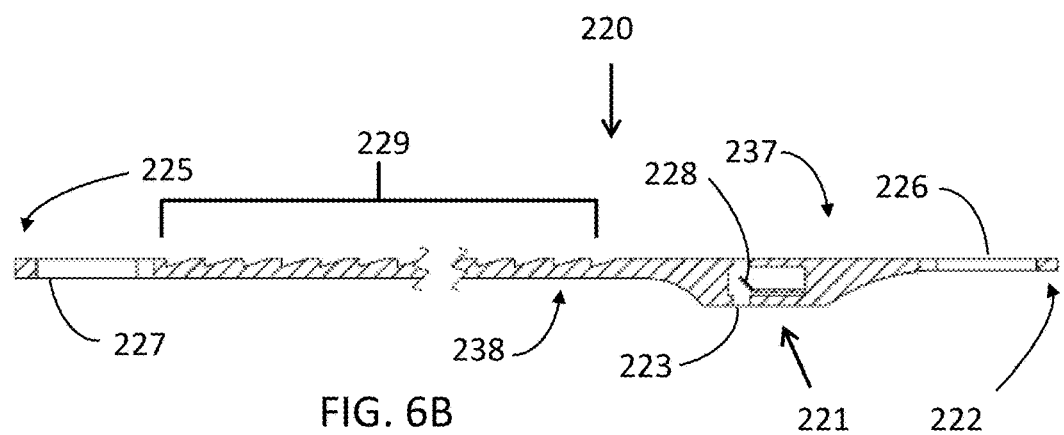

Patient's may feel geometric features such as bulges or protrusions of an implant that reside below the surface of the skin, that is, the features be palpable or cause a sensation when pressing against the tissue below the skin. A self-locking strap 220 having a flat top side 237 is shown in FIG. 6A. The strap 220 may have a lock-head 221 with a slot 223 therethrough for receiving the distal tip 225, an elongate body 229, a proximal tip 222 with a proximal aperture 226, a distal aperture 227 and a plurality of teeth 224 arranged along the length of the body. The lock-head 221 protrudes on the bottom side 238 and tends to embed into the fascia and muscle so that the self-locking strap remains relatively flat on the top side 237, which may be adjacent to the skin. That is, the distal tip 225 of the strap may transit through the lock-head 221 from the bottom side 238 to the top side 237. As illustrated in a broken view in FIG. 6B, the lock-head 221 may have a pawl 228 to engage with the teeth 224 or any other type of ratcheting mechanism that affords one-way movement after the distal tip 225 is pulled through the lock-head 221. A needle may be placed through the slot 223 such that the needle can engage with the distal tip 225 to pull the distal tip 225 back through the slot 223 to lock the strap as is further described in FIGS. 18A-18I.

Figure 7A:
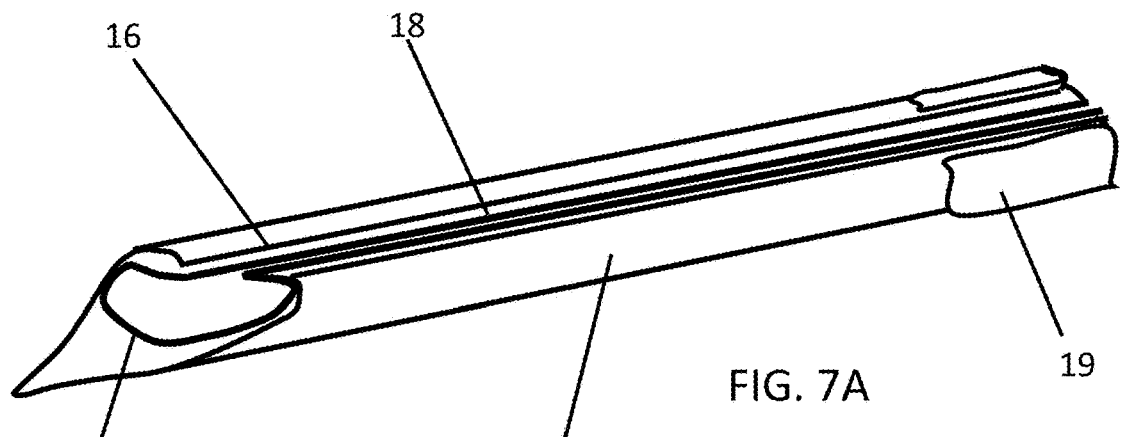
FIGS. 7A-7K show various embodiments of a slotted needle that holds a strap that may be removed laterally from the lumen of the slotted needle.

Now with reference to FIG. 7A, which shows an embodiment of a slotted needle 15 comprising a slot 16 that may extend from the heel of the needle to the proximal end of the needle where a handle 19 may reside. The slotted needle 15 may have an outer diameter of approximately 1.65 mm (16 gauge), the slot 16 may be 0.25 mm to 0.75 mm wide or approximately 0.5 mm wide, and the slotted needle 15 may be approximately 20 cm in length. Embodiments of the slotted needle 15 allow the needle to be inserted through the full-thickness abdominal wall, for example the skin, anterior rectus sheath, the abdominal wall, and posterior rectus sheath, without deforming, while providing a conduit for the advancement of a self-locking strap into the body. To aid in retaining the strap, the inner lumen of the slotted needle 15 may contain an inner tube 17 that may have a slot 18 to allow a strap to be released. For clarity, this device and other devices disclosed herein may be shown out of proportion in the drawings to emphasize details or functionality.

Figure 7B:
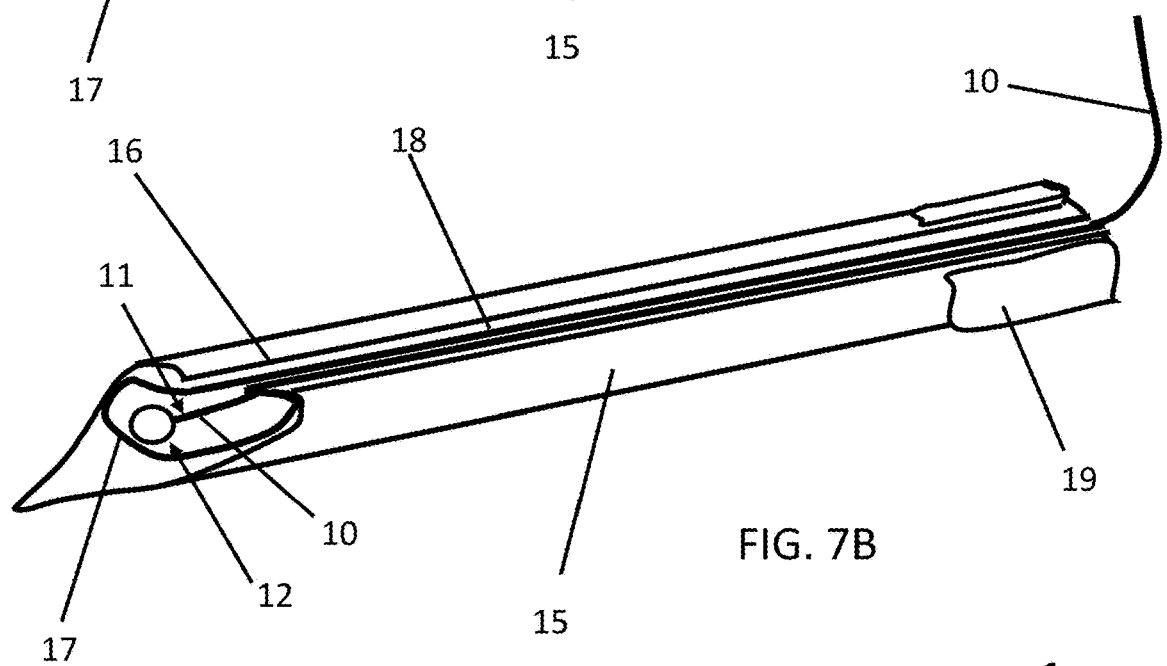
Figure 7C:
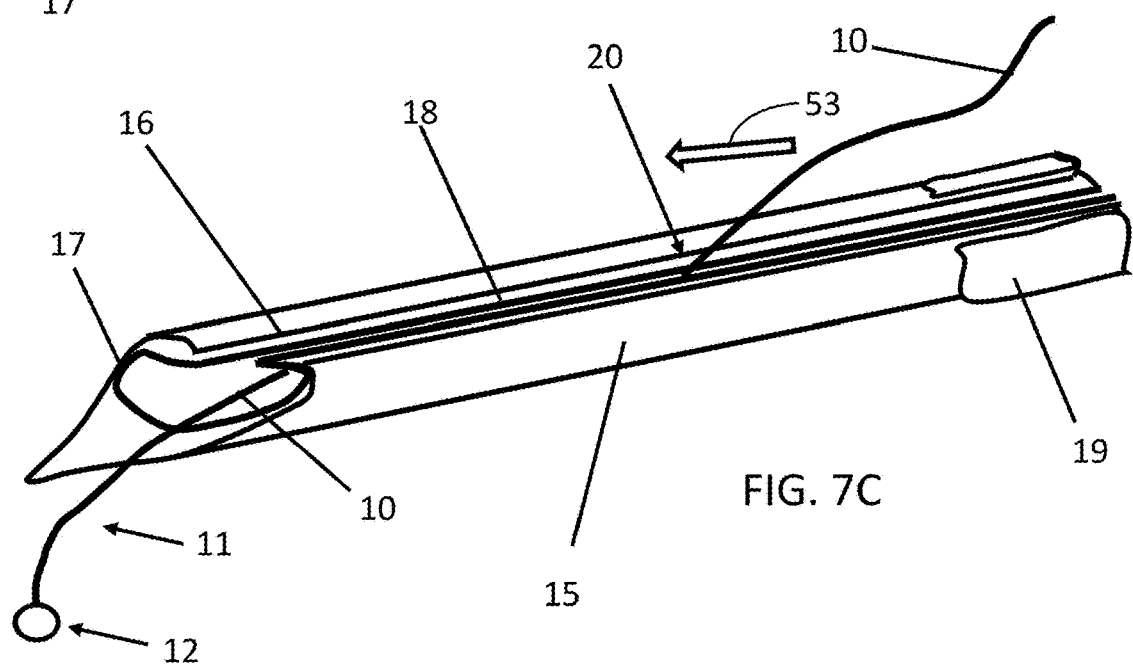

The slotted needle 15 may be used to deliver a suture or strap into the body minimally invasively while allowing the surgeon to withdraw the suture or strap from the slotted needle 15 through the side of the needle rather than pulling it out through the lumen; this may lead to a smaller size of the slotted needle 15, and hence the wound size. A strap with oversized features such as a lock-head may be passed through the slotted needle 15 and into the body, but if the lock-head doesn't fit through the lumen, the strap may be released through the side (slot 16) of the slotted needle 15. This maneuver is illustrated in FIGS. 7B and 7C in the context of the self-locking strap 10, but other embodiments of a suture or strap may be constrained within and removed from the slotted needle 15 in this manner. As shown in FIG. 7B, the protuberance 12, which resides near the distal end 11 of self-locking strap 10, lies in the lumen near the tip of slotted needle 15. Once the slotted needle 15 is introduced inside the body cavity and through the desired tissue sections, the distal end 11 may be advanced through the lumen; a tamp or other driver (not shown) may be used to push the self-locking strap 10 through the lumen. In FIG. 7C, the distal end 11 has been advanced out of the slotted needle 15, so that the protuberance 12 lies distal to the needle tip. The slotted needle 15 may then be peeled away from distal end 11, as shown by peel-away site 20 at the intersection with the slotted needle 15. The peel-away site 20 may move distally as the self-locking strap 10 is pulled away from the slotted needle 15 generally in the direction indicated by the arrow 53. Once the distal end 11 has been introduced into the abdominal cavity and removed from the slotted needle 15, the slotted needle 15 may be retracted from the body leaving at least the distal end 11 in the abdominal cavity.

Figure 7D:
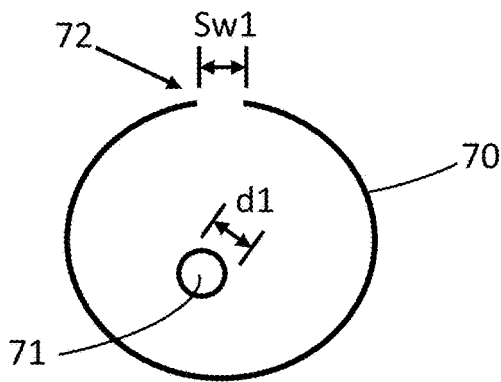
Figure 7E:
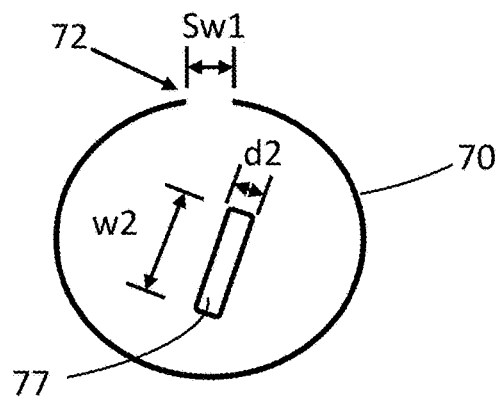

A strap may be retained the lumen of a slotted needle by a variety of methods. By way of nonlimiting example, several slotted needle designs are shown in FIGS. 7D-7H, which all show an end-view of a slotted needle schematically. FIG. 7D illustrates a slotted needle 70 having a slot 72 with a strap 71 disposed inside the lumen. The diameter d1 of the strap 71 may be smaller than, equivalent to, or slightly larger than the width of the slot Sw1 so that the strap has a clearance or slight interference fit when passing through the slot 72. If the strap diameter d1 is smaller than the slot width Sw1, it still may be retained because the strap should align with the slot 72 along much of the full length of the slot 72 to be removed, and hence it tends to stay retained until pulled on transversely to extract the strap 71 incrementally from the slotted needle 70. As shown in FIG. 7E, a strap 77 with an elongate cross-section is illustrated, having a minimum width d2 and a maximum width w2; the strap 77 is shown residing inside of a slotted needle 70. The strap 77 will tend to remain captive in the needle 70 even if the minimum width d2 is smaller than the slot width sw1 because the strap 77 will not generally be aligned with the slot 72 unless the surgeon twists the strap 77 and needle 70 into alignment in order to release the strap.

Figure 7F:
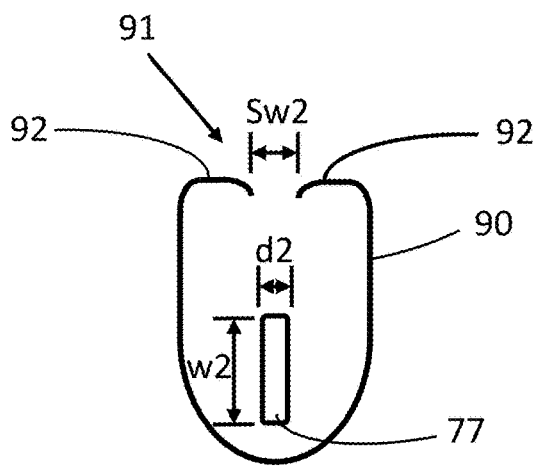
Figure 7G:
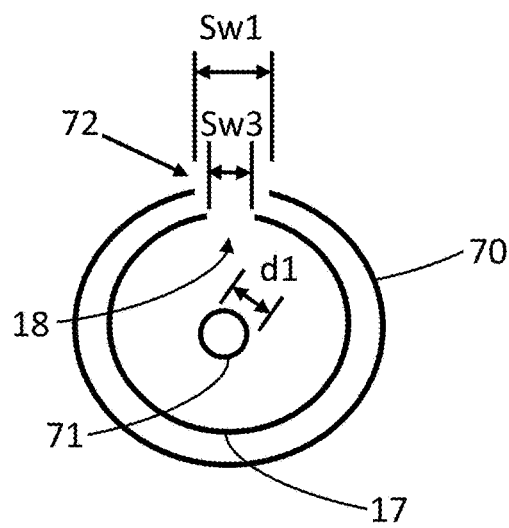
Figure 7H:
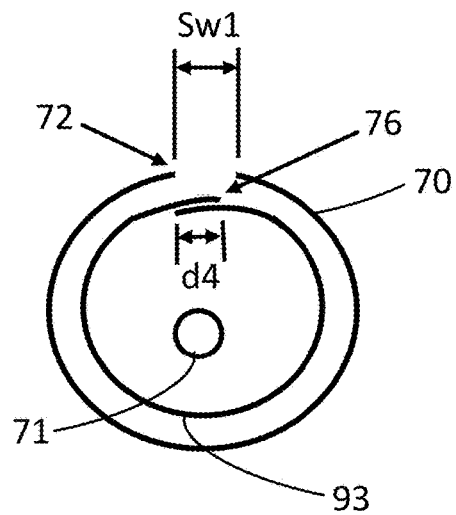

One skilled in the art will realize that there are many ways to retain a strap inside of a slotted needle while rendering it easily removable when desired. In some embodiments, the slotted needle may not be round as shown in FIG. 7F. In this embodiment, the slotted needle 90 has an oblong shape with a flattened section 92 having a slot 91 therethrough. The strap 77 may also have an elongated cross-sectional shape that tends to stay inside the lumen until its minimum strap width d2 is aligned with the slot 91 by the surgeon when the strap 77 is pulled from the slotted needle 90. In yet another embodiment, FIG. 7G shows a slotted needle 70 having an inner tube 17 within its lumen. The inner tube 17 may be made of any flexible material such as a polymer, for example, polyethylene or Nylon, or an elastomeric material such as a rubber, silicone, or a thermoplastic elastomer. The inner tube 17 may have a slot 18 with a width Sw3 that may be larger than, equivalent to, or smaller than the diameter d1 of the strap 71 such that it offers some resistance to hold the strap 71 inside of the lumen. The inner tube 17 may be made of a thin walled membrane that deforms when the strap 71 is peeled from the lumen. The slot 18 may be an actual slot through the inner tube 17 that remains open or slightly closed until peeled open, or it may be a serrated line that opens with a small amount of force. The inner tube 17 may be bonded or otherwise fit into the inner lumen of the slotted needle 70, maximally extending from the heel of the needle point to the proximal end of the needle, near the tip, or anywhere therebetween with enough overlap with the slot 72 to retain the strap 71. In yet another embodiment, the inner tube 93 may have a circumferential length such that it has an overlap 76 that may have a length d4 that may be approximately 0.5 to 2 mm, as shown in FIG. 7H. The inner tube 93 should have a wall thickness that is thin enough so that it deforms and opens under the peeling pressure when the surgeon peels the strap 71 from the slotted needle 70.

Figure 7I:
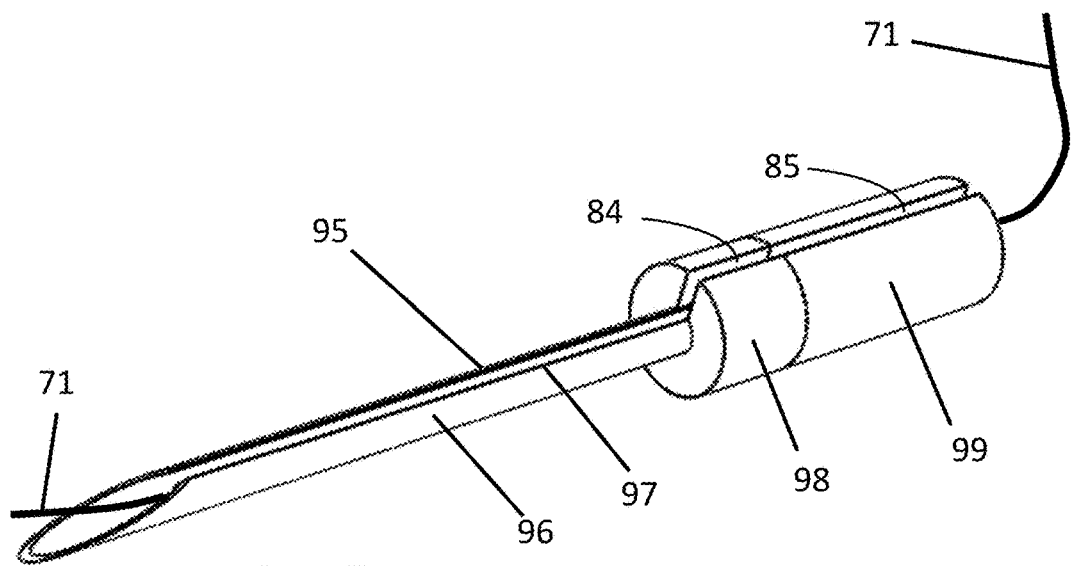
Figure 7J:
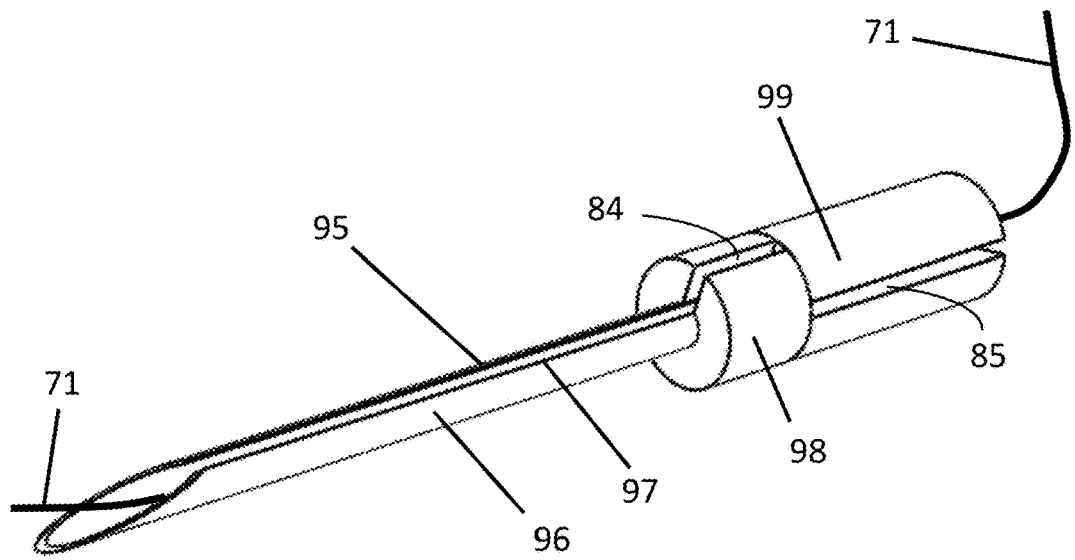
Figure 7K:
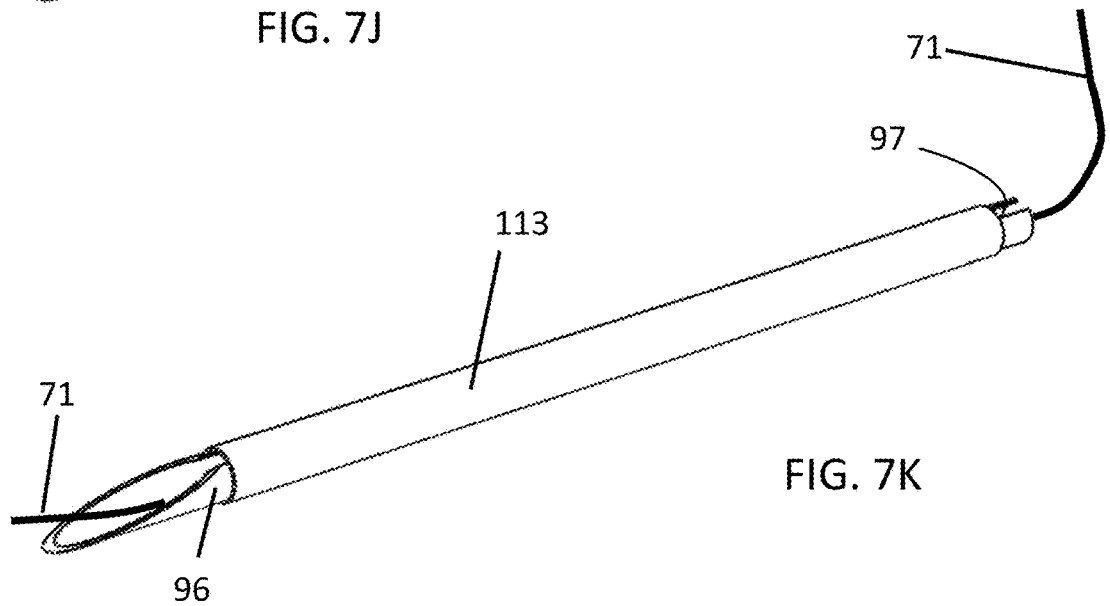

FIGS. 7I-7K illustrate other embodiments of a slotted needle. In FIG. 7I a slotted needle 95 is shown having a stationary handle 98 and a rotating handle 99, each having a slot—a stationary slot 84 and a rotating slot 85 respectively. When the slots are aligned, the strap 71 may pass through the slot 97 in the shaft 96 and through the stationary handle 98 and the rotating handle 99 to be removed from or inserted into the slotted needle 95. However, when the stationary handle 98 and the rotating handle 99 are not aligned, as shown in FIG. 7J, the strap 71 remains captured in the slotted needle 95. One skilled in the art would recognize that this operation could also be achieved with a single slotted handle (not shown) that rotates around the shaft 96 of the slotted needle 95 to align/misalign the handle slot and the slot 97 on the shaft 96 as desired to retain or release the strap 71. In yet another embodiment, a sleeve 113 may be placed over the slotted needle 96 to cover the slot 97 as shown in FIG. 7K. The sleeve may be as long as the slotted needle 96 or smaller in length, and it may have a serration or gap (not shown) to facilitate removal or it may be cut and released from the slotted needle 96 by the surgeon in order to release the strap 71.

Figure 8A:
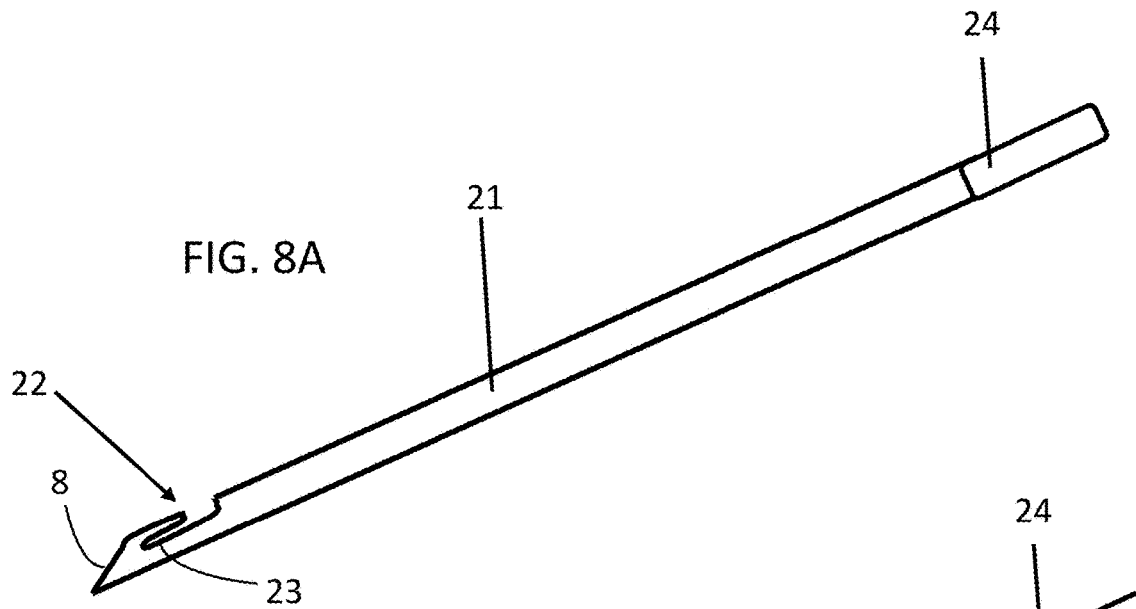
FIGS. 8A-8C show a hook needle that is used to pull a strap from the body.

In some embodiments, the system may include a hook needle 21 to grasp a strap from within the body cavity. For example, a hook needle 21 can be used as a needle or a trocar to directly pierce tissue without the need for an external trocar. As illustrated in FIG. 8A, the hook needle 21 may have an open slot 22 leading to a channel 23 near its distal portion and a beveled tip 8, so that it is capable of piercing through multiple layers of tissue. The width of the channel 23 may be 0.25 mm to 1 mm, or approximately 0.5 mm, but generally of a size that is slightly larger than the width of the strap. The outer diameter of the hook needle 21 may be approximately 1 mm to 3 mm or about 1.65 mm (16 gauge). The dimensions of the slot 22 and channel 23 should be selected based on the size of the strap and/or the size of any grasping feature on the strap. The hook needle 21 may be approximately 20 cm long, or any length appropriate to enter the body cavity for a given patient's anatomy, and it may include a handle 24 attached to its proximal end. The hook needle 21 shall be sufficiently strong and stiff that it can be inserted through multiple layers of tissue in the abdomen, that is, the full thickness abdominal wall which includes the anterior rectus sheath, the rectus abdominus muscle, and the posterior rectus sheath to grasp the distal end of a strap to pull it back through the layers of tissue and out of the body. As such, the hook needle 21 may have any cross-sectional shape that provides the proper stiffness and strength including a round or oval cross-section which may be solid or hollow or a flat or rectangular cross-sectional shape.

Figure 8B:
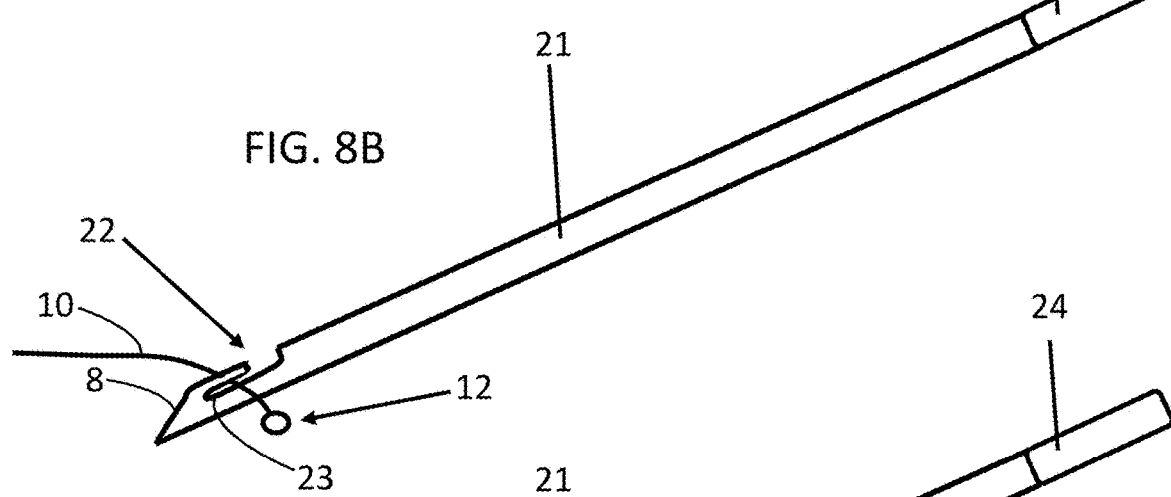
Figure 8C:
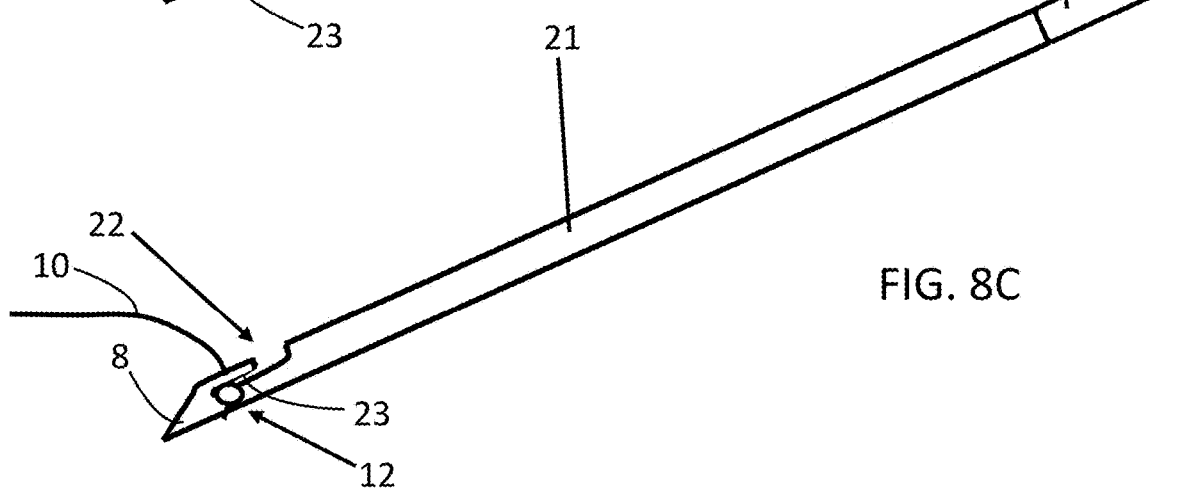

FIG. 8B shows the hook needle 21 engaging the self-locking strap 10 proximal to the protuberance 12 via the open slot 22. The surgeon hooks the self-locking strap 10 with the open slot 22 and then pulls the tip of the hook needle 21 so that the protuberance 12 seats against the side of the hook needle 21. As shown in FIG. 8C, the protuberance 12 is hooked in the channel 23 of hook needle 21, thereby enabling the surgeon to grasp and manipulate the self-locking strap 10 via the hook needle 21. The self-locking strap 10 with the protuberance 12 on the end is shown here as an example, however, the hook needle 21 may be used to grasp any suture or strap or features thereon from within the body, such as a strap with a loop or a strap having an aperture for engaging with the hook needle 21 such as the distal aperture 128 of the aforementioned self-locking strap 120.

Figure 9A:
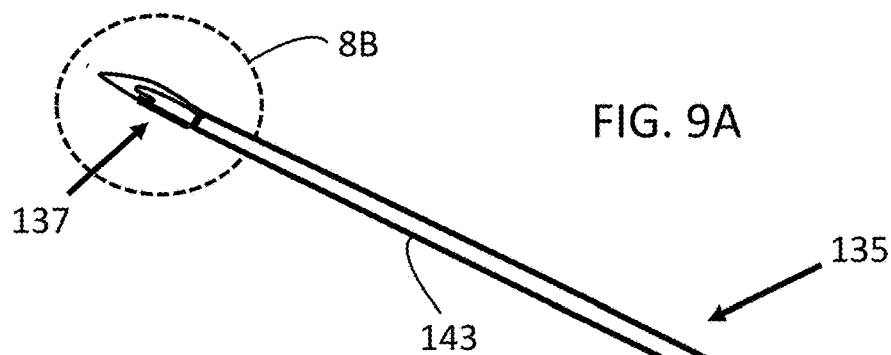
FIGS. 9A-9C show a grasper for grasping a strap within the body.
Figure 9B:
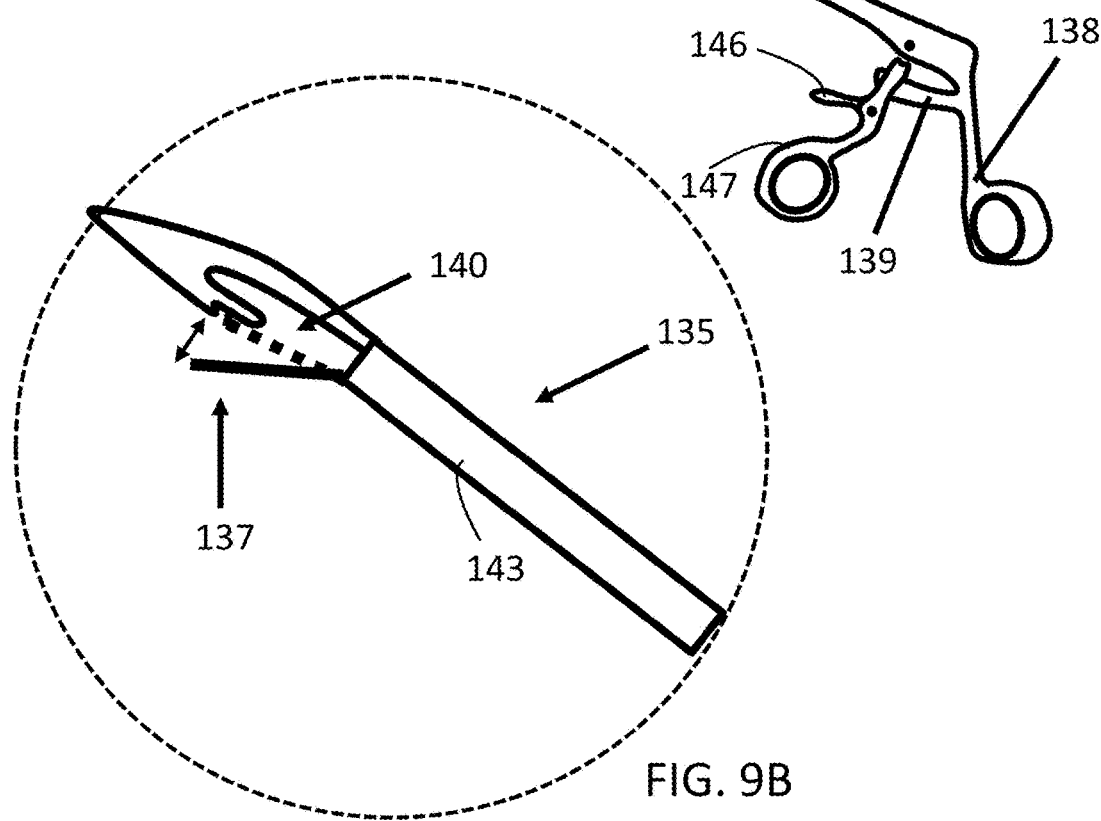
Figure 9C:
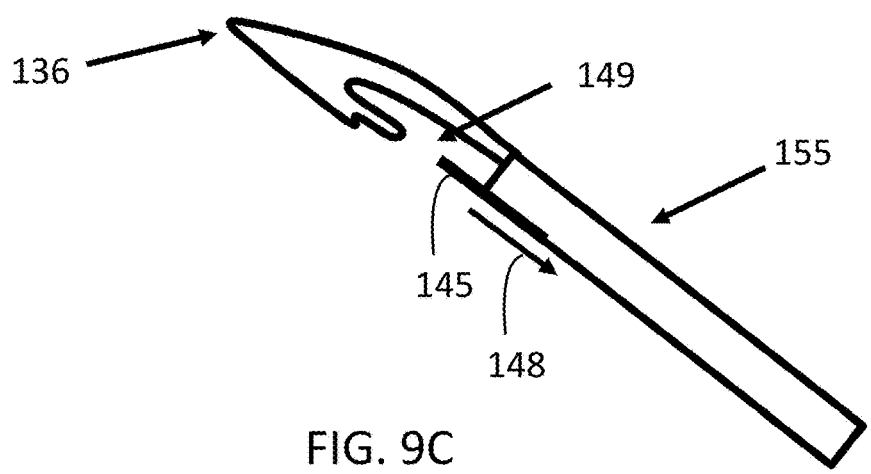

The open slot 22 on the hook needle 21 may be any passive feature such as a slot, hook, or carabiner type latch, or an active grasping mechanism such as a claw, jaw, or clasp. Each of which allow the hook needle 21 to grasp a suture or strap that resides within the body. For example, a surgical grasper 135 may be used as shown in FIG. 9A. The grasper 135 may have a handle 138 with a lever 147 that actuates a movable jaw 137 near the distal end of a shaft 143. The movable jaw 137 may articulate about a pivot such that it opens to allow access to the open slot 140 as shown in FIG. 9B. FIG. 9C shows an analogous partial view of the distal tip of another embodiment of a grasper 155 having a sliding jaw 145 that slides in the direction of the arrow 148 to expose an open slot 149. The grasper 155 may have a needle tip 136 that is sharp enough to allow the grasper 155 to penetrate through the multiple layers of tissue of the full-thickness abdominal wall to reach the strap within the body for retrieval. One skilled in the art will recognize that there are standard graspers having a handle that actuates a jaw or clamp at a distal end and may have a ratchet lock 139 (FIG. 9A) to lock the distal mechanism in place and a ratchet release 146 to release it. Such devices may be used for this procedure and are within the scope of this disclosure.

Once a self-locking strap has been accessed inside of the body cavity by the hook needle 21 or similar instrument and pulled the self-locking strap through the muscle, the surgeon needs to manipulate the self-locking strap to tension it and to lock it. The surgeon may tension it outside of the body where it is easier to directly see the self-locking strap and to manipulate it. Hence, the surgeon may pull the end of the self-locking strap out of the body through the skin incision site on the opposite side of the defect from the hook needle 21 to join it with the opposite end of the strap. Without a subcutaneous guide, finding the strap or a needle below the surface of the skin is cumbersome because the strap is below the surface of the skin and out of sight, as there is generally no camera at the subcutaneous level, so the surgeon may have to feel around inside the body to find the strap by trial and error which takes a considerable amount of time and effort. It is easier to pull the strap out of the body if the strap is already captured while it is in the body. Since the strap is already inside of the hook needle 21, if the hook needle 21 is contained by a subcutaneous guide, which may be in place in the body beforehand, the subcutaneous guide makes capturing the strap automatic because when the hook needle 21 is withdrawn through the subcutaneous guide, the strap is already captured by the subcutaneous guide 25. The subcutaneous guide should be rigid enough and able to withstand axial, buckling, and bending loads as well as torsion because the subcutaneous tissue that it must tunnel through has fibrous interconnections interspersed in the fatty tissue and a significant amount of force may be required to perform the blunt dissection across the defect between the incision sites. Advancement of the subcutaneous guide using a concomitant back and forth rotational motion may be employed.

Figure 10A:
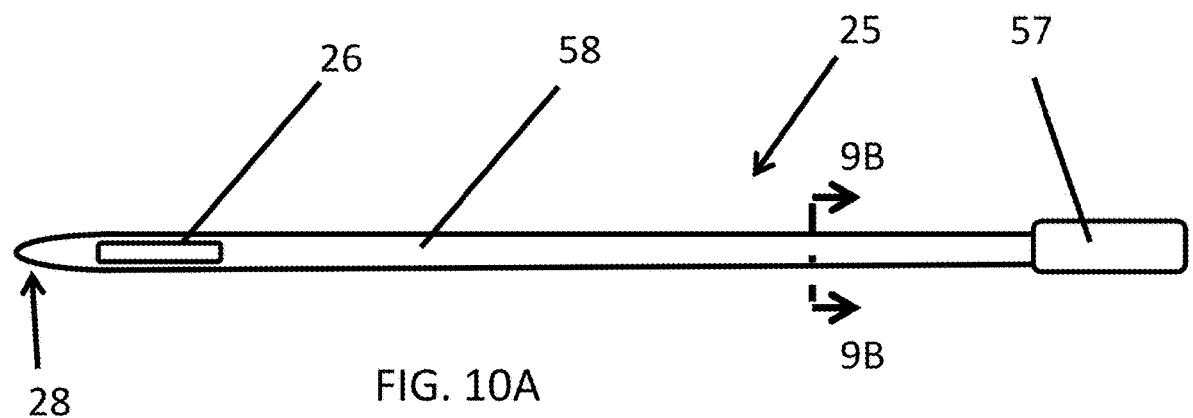
FIGS. 10A-10H show various embodiments of a subcutaneous guide for tunneling subcutaneously between two incision sites.
Figure 10B:
Figure 10C:
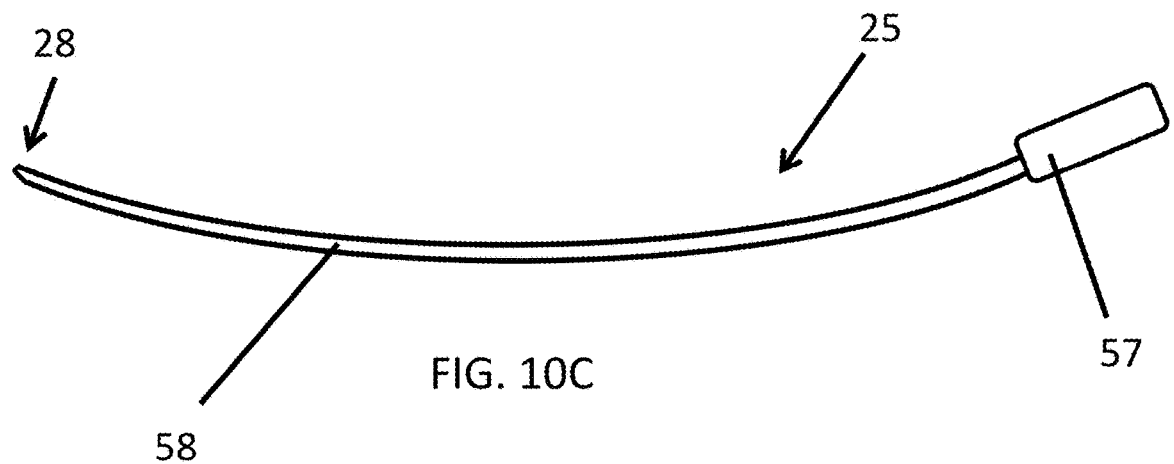
Figure 10D:
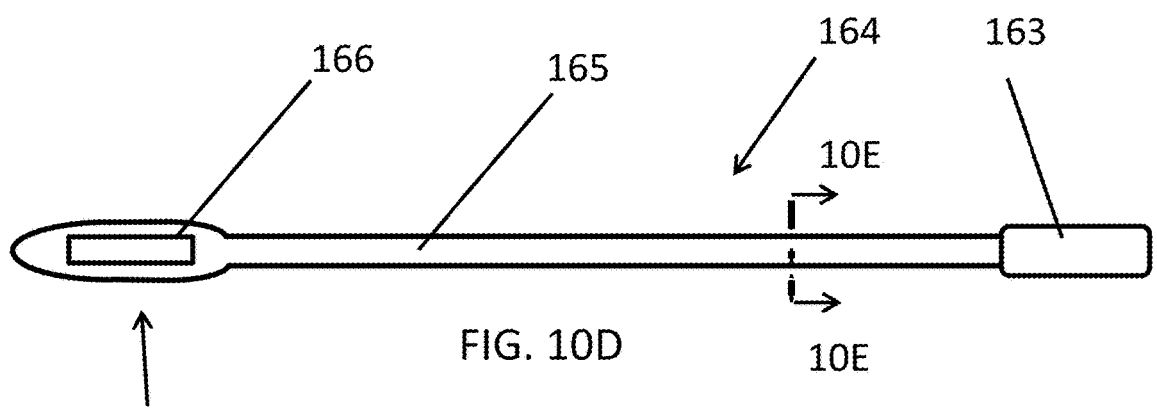
Figure 10E:
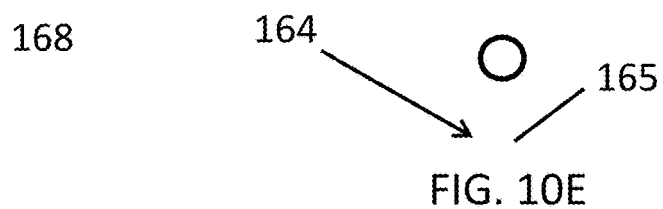
Figure 10F:
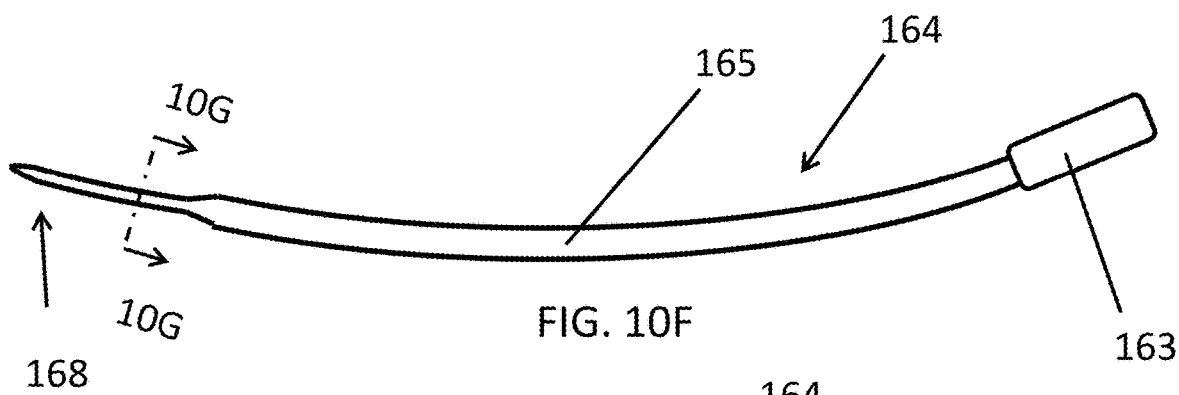

FIGS. 10A-10C depict a subcutaneous guide 25 that may have an elongate body 58, a handle 57, a distal tip 28 and one or more slots, such as the distal slot 26. Since the distance between the incision sites is not generally the same between patients, the subcutaneous guide 25 may have a series of slots (not shown) along its elongate body 58. The subcutaneous guide 25 is used to tunnel between two incisions in the abdomen below the surface of the skin but above the muscle and fascia. Therefore, it must be strong enough to dissect layers of tissue that may include tough, fibrous fatty tissue without bending or buckling. As such, in embodiments, to facilitate dissection, the distal tip 28 may be pointed in shape and may be beveled or tapered. In other embodiments, the distal tip 28 may be sharp to facilitate sharp dissection, or it may be relatively blunt for blunt dissection. The elongate body 58 may have a tubular or solid cross-section that may be shaped as an oval, as shown in FIG. 10B, or any other cross-sectional shape that provides the requisite strength to tunnel through the tissue subcutaneously. The major diameter may be small such as about 3 mm or approximately 1 mm to 4 mm to facilitate tunneling. The slot 26 may be 0.5 mm to 3 cm long, for example, or approximately 2 cm long and a width dimension that can accommodate the hook needle 21 or similar instrument that may be introduced through the subcutaneous guide 25. For example, if the hook needle 21 has a diameter of 1.65 mm (16 gauge), then the distal slot 26 should be wider than 1.65 mm so that the hook needle 21 can be passed through the distal slot 26. The subcutaneous guide 25 may be made of any biocompatible material suitable for surgical use, such as a metal or plastic material that is stiff enough to tunnel through the body, such as stainless steel. The subcutaneous guide 25 may be straight or may be shaped in a gradual curve as shown in FIG. 10C. The curve of the subcutaneous guide 25 may allow it to enter the skin incision on one side of the hernia defect, cross the region of the defect, and locate the skin incision on the opposite side more easily on some body types. In other anatomical body shapes, for example if the abdomen has significant curvature, a straight subcutaneous guide may be used.

Figure 10G:
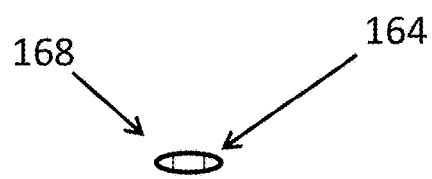

FIGS. 10D-10G illustrate another embodiment of a subcutaneous guide 164 that may include an elongate body 165, a handle 163, and a distal tip 168 having a slot 166. This embodiment may have a round cross-sectional shape through most of the elongate body 165, as illustrated in the section view FIG. 10E, but may be flared at the distal tip 168 into a wider and flatter shape to provide a larger target area for the hook needle 21. The body 165 may be tubular or solid and shall be thick enough to tunnel through the subcutaneous tissue as described above for the other embodiment of a subcutaneous guide 25. The cross-sectional shape of the tip, as shown in FIG. 10G, is an oval or flattened shape that may be formed by swaging, crimping, or otherwise compressing the elongate body 165 to deform it into such a shape. The shape of the distal tip 168 may facilitate blunt dissection through tissue, and the flat and relatively wide platform of the distal tip 168 provides a large target area when passing the hook needle 21 through the slot 166. This embodiment may otherwise have the same material, sharpness, and geometric attributes described above for the embodiment described in FIGS. 10A-10D.

Figure 10H:
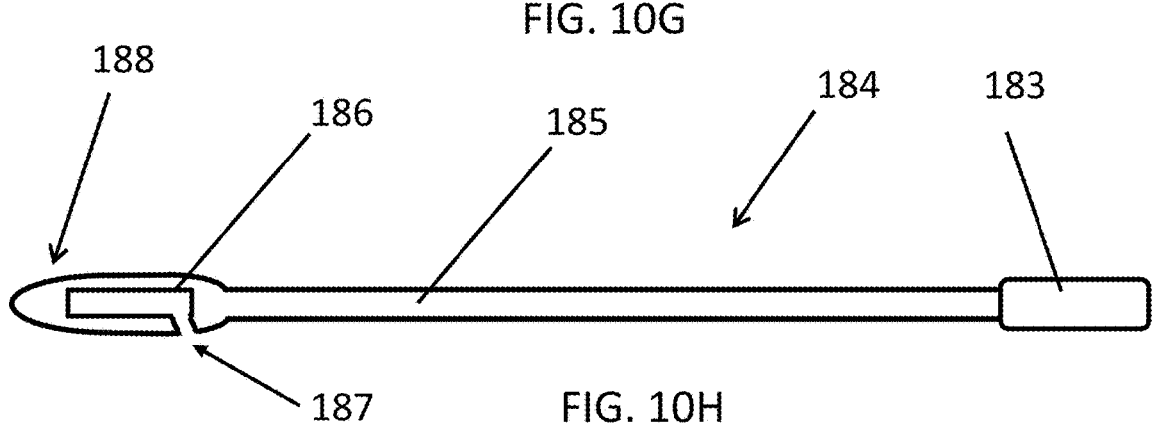

FIG. 10H illustrates yet another of a subcutaneous guide 184 that may include an elongate body 185, a handle 183, and a distal tip 188 having a slot 186. This embodiment may have the same geometric and structural attributes of the previously described subcutaneous guides, but in addition, it may have a gap 187 for access to the slot 186. A strap or needle can enter the slot 186 through the gap 187 if the needle or strap is already in the body when the subcutaneous guide 184 is tunneled across the subcutaneous tissue.

Figure 11A:
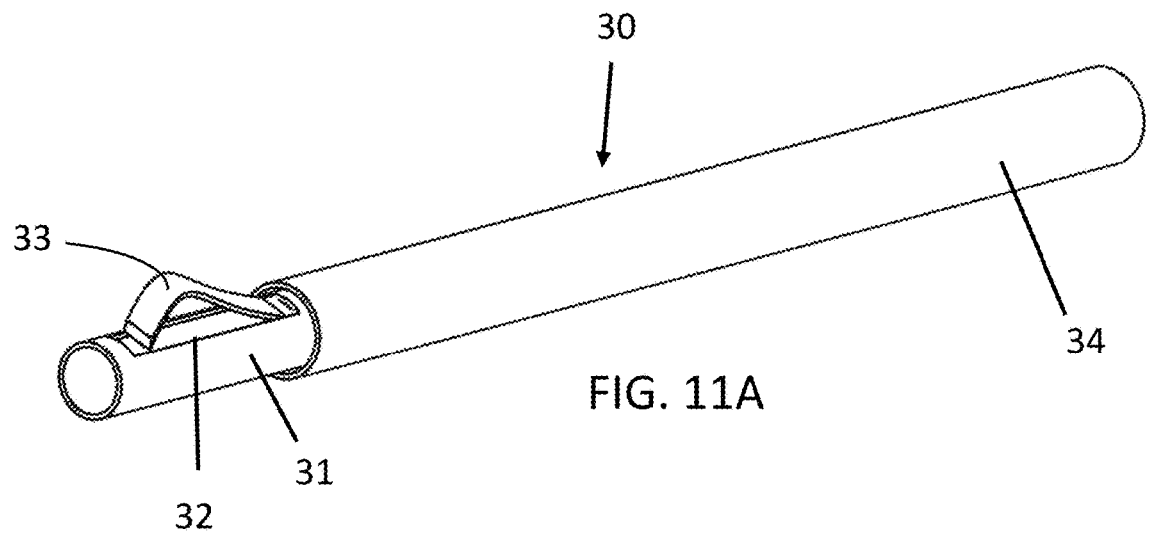
FIGS. 11A-11C show a tubular cutter used to sever the excess length of the self-locking strap.
Figure 11B:
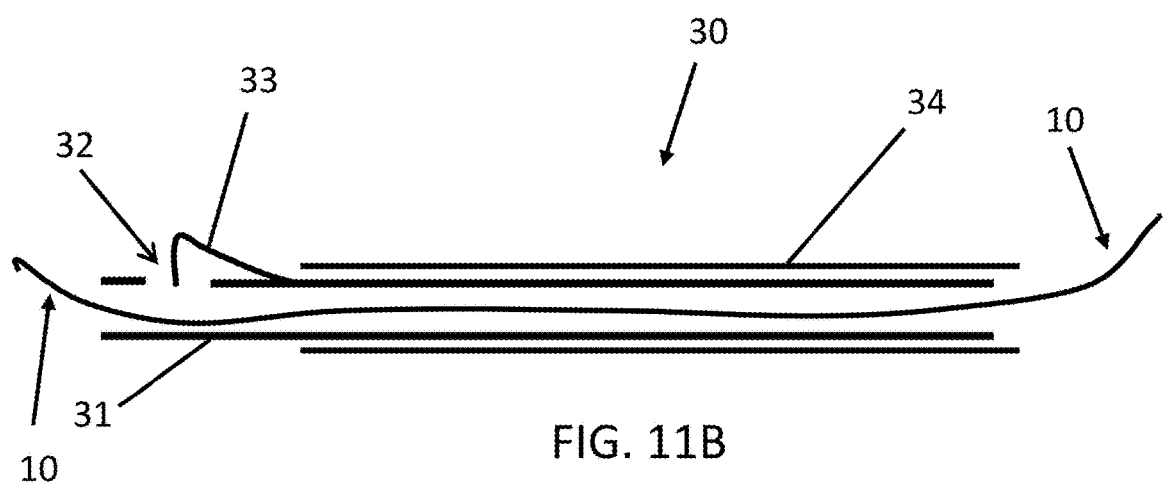
Figure 11C:
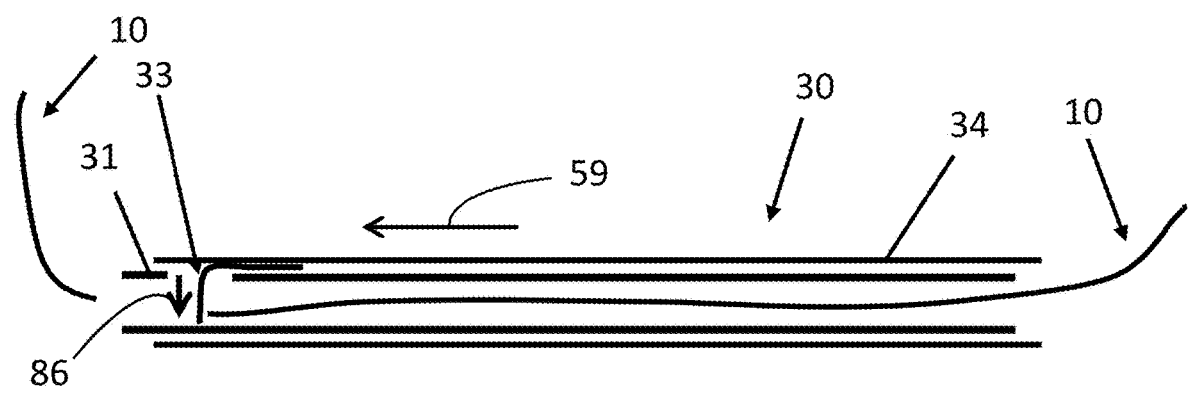

Once the self-locking strap 10 has been tightened and locked around tissue in the body, excess strap material may be removed. In order to limit the amount of excess strap that may contact tissue within the body cavity, it is desired to cut the excess strap near to lock-head which may be deep inside of the body cavity and difficult to reach. One way to find the lock-head is to follow the excess strap that protrudes outside of the body cavity down into the body to the lock-head; this excess strap may be used as a guide to pilot a cutting device down to the strap to the desired location for cutting. FIGS. 11A-11C depict an embodiment of a tubular cutter 30 used to cut the excess remaining length of a self-locking strap after the hernia defect has been closed. FIG. 11A shows a perspective view of the tubular cutter 30 that is comprised of an inner tube 31 having an opening 32 near its distal end and an outwardly sprung cutting blade 33 that is attached to or integral to the inner tube 31 proximal to the opening 32 in the inner tube 31. An outer tube 34 lies coaxial to the inner tube 31 and proximal to a cutting blade 33. FIGS. 11B and 11C schematically illustrate the operation of the tubular cutter 30 via a side section view. With reference to FIG. 11B, the surgeon uses the self-locking strap 10 as a guide to advance the tubular cutter 30 down over the self-locking strap 10, that is inside of the lumen of the inner tube 31, to the desired distance where the cutting blade 33 meets the section of self-locking strap 10. As shown in FIG. 11C, the surgeon may sever the self-locking strap 10 by advancing the outer tube 34 distally over the inner tube 31, as indicated by the arrow 59, such that the outer tube 34 contacts the cutting blade 33 forcing it to move radially into the lumen of the inner tube 31 as indicated by the arrow 86. As the cutting blade 33 moves into the lumen, it intersects with the self-locking strap 10, thus cutting it. One skilled in the art would recognize that there are other ways of advancing the outer tube 34 to get more force or leverage, such as having handles attached. In other embodiments the tubular cutter 30 may have a threaded interface between the outer tube 34 and inner tube 31 so that the outer tube 34 may be advanced by twisting it along the threads so that it can be advanced over the cutting blade as it is screwed down the outer tube 34 until it depresses the cutting blade 33. Such designs may provide a larger mechanical advantage to actuate the cutting blade 33 than pushing the outer tube 34 directly.

Figure 12A:
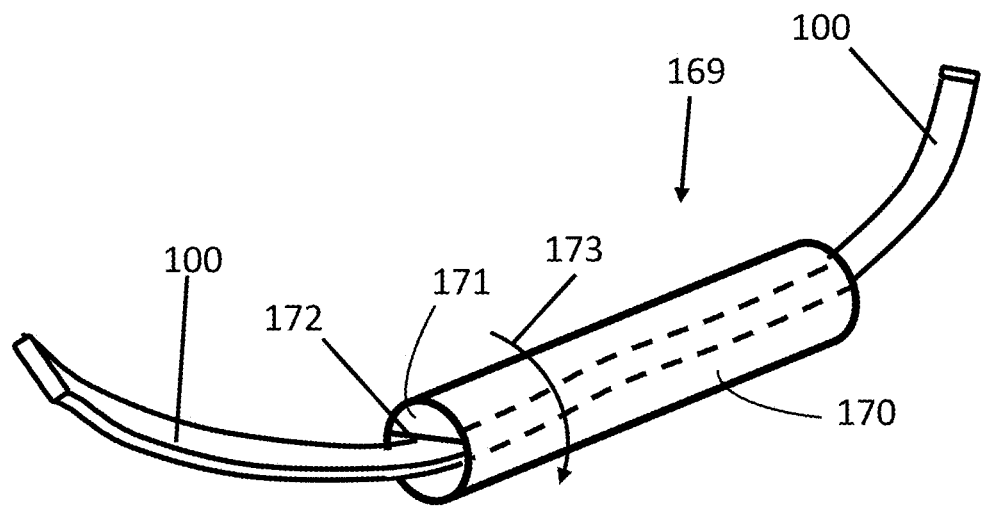
FIGS. 12A-12B show a rotational cutter used to sever the excess length of the self-locking strap.
Figure 12B:
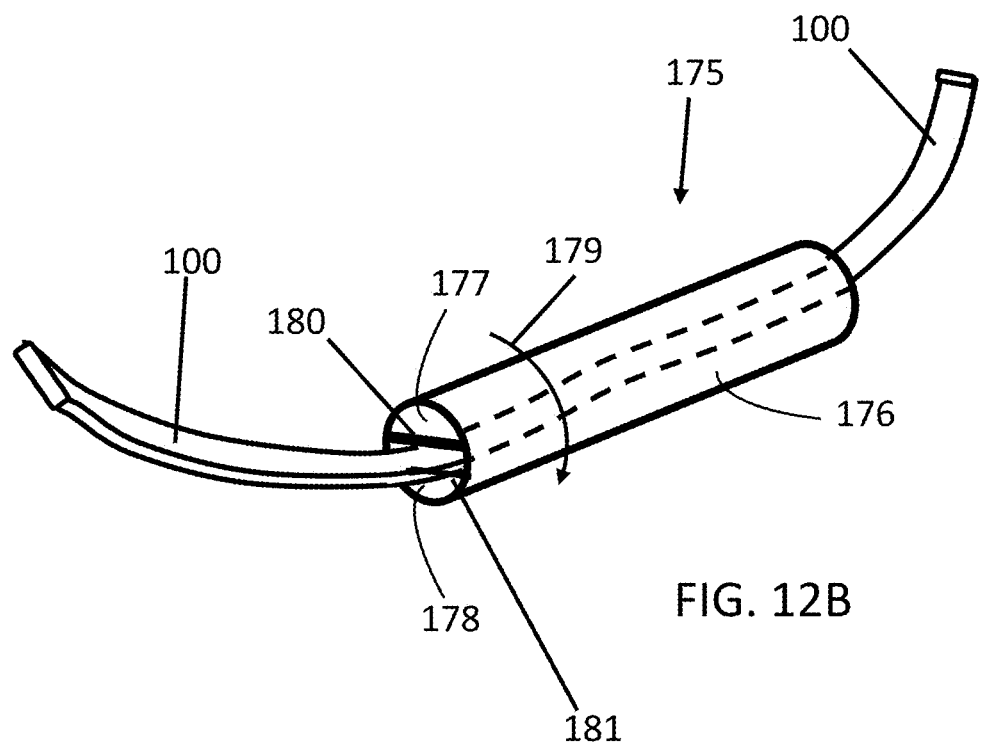

In other embodiments, the surgeon may use traditional cutting tools, scissors, or laparoscopic cutting tools to cut the strap and remove the excess material. In some embodiments a rotational cutter may be used. With reference to FIG. 12A, a rotational cutter 169 is shown having an elongate body 170 with a length capable of extending through an incision and into the body to the desired depth to cut the self-locking strap 100 and an inner diameter size that will accommodate passing the strap 100 therethrough. The rotational cutter 169 may be placed over the self-locking strap 100 and advanced down along the self-locking strap 100 to the desired depth where the rotational cutter 169 may be used to sever any excess strap. In practice, the surgeon may advance the rotational cutter 169 along the self-locking strap 100 until the surgeon feels it abut against the lock-head (not shown) of the strap 100 and then the surgeon may rotate the rotational cutter 169 knowing that it has reached the desired depth for cutting. The elongate body 170 may have an arrangement of blades in its inner lumen. For example, the rotational cutter 169 has a cutting blade 171 mounted to the inner diameter and extending into the lumen such that the cutting edge 172 will intersect with the self-locking strap 10 when the body 170 is rotated, for example in the direction of the arrow 173. In another embodiment illustrated in FIG. 12B, the rotational cutter 175 has a similar elongate body 176 but has an arrangement of two cutting blades 177 and 178 extending into its lumen. The rotational cutter 175 may be passed down over the self-locking strap 100 such that the strap 10 is between the cutting edge 180 and the opposing cutting edge 181. When the elongate body 176 is rotated, for example in the direction of the arrow 179, the cutting edges 180 and 181 will intersect with the self-locking strap 100, thus severing it. One skilled in the art will recognize that there are many blade arrangements that can be provided to cut a strap within the lumen of a tube upon rotation, all of which are within the scope of this disclosure. For these embodiments, the blades may be similar to razor blades and may be made of steel while the tube may be made of steel or a polymeric material. The blades may be joined to the tube by any appropriate metal joining process such as a welding process, such as laser welding, or they may be bonded (potted), or crimped in place by features on the tube. Alternatively, the blades may be bonded, heat staked, or insert molded into a polymeric tube.

In procedures for tissue approximation wherein a self-locking strap is used, a strap tensioning device may be employed to tighten the strap against the lock-head that will be positioned in contact with the anterior rectus sheath of the patient. The tightening device may have a small diameter (5 mm or less) distal tubular extension that allows it to be inserted through the small skin incision and it may extend through a layer of subcutaneous fatty connective tissue to rest against the lock-head. For example, a simple version of a tensioning device is the support tube 45 (FIGS. 18I-18J) which may be advanced down to the lock-head to allow the surgeon to push on the lock-head while pulling the strap in the opposite direction. The tensioning device may impart a degree of mechanical advantage to the strap tightening maneuver, to facilitate the process of placing multiple straps. Additionally, the tensioning device may provide a measurement of the tension applied by the strap to abdominal wall tissue during the hernia repair procedure. Excessive tension placed on tissue during abdominal closure, whether it be performed by conventional suture or self-locking straps, may result in tissue tearing and recurrence of a ventral hernia.

Figure 13A:
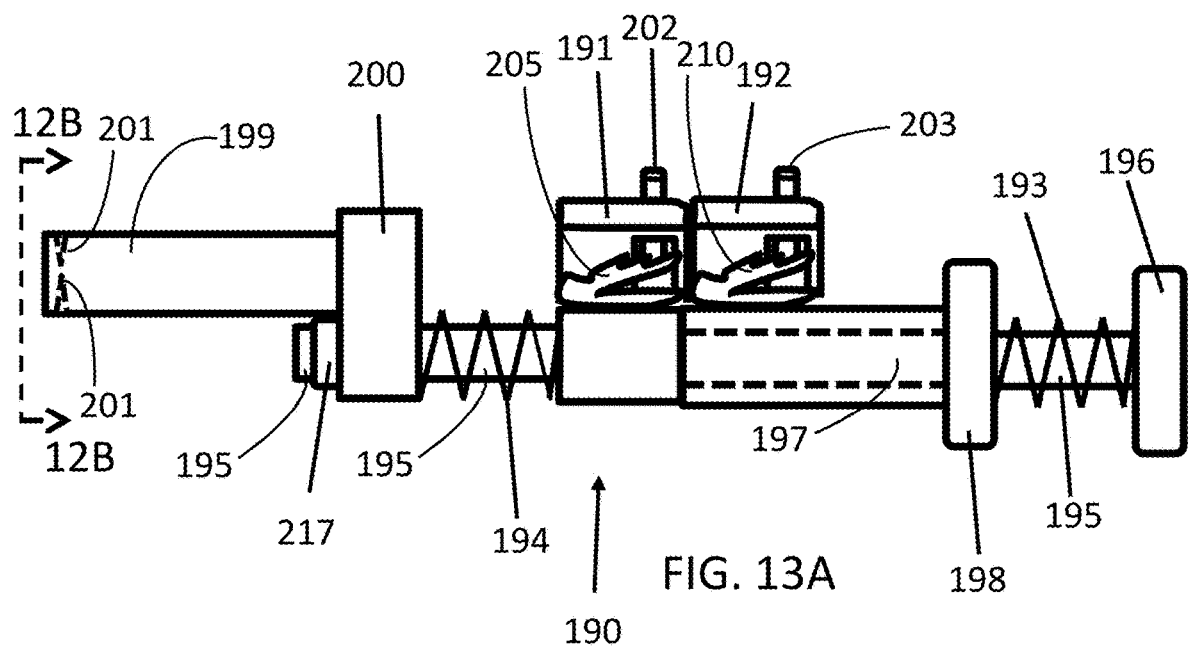
FIGS. 13A-13B show an embodiment of a strap tensioning device.

An embodiment of a tensioning device 190 is shown in FIG. 13A. The device 190 may have a series of two locking ratchet heads (lock-heads) that are translatable from each other in an axial manner. The stationary lock-head 191 is distal and is stationary, as it is fixedly attached to the inner core 195 of the device 190. The movable lock-head 192 is proximal to the stationary lock-head 191 and is movable along the inner core 195. The two lock-heads 191 and 192 are maintained in alignment with each other via their attachment to a plunger system with coaxial components that may contain a non-round cross-section or keyway feature to prevent relative rotation of the components during actuation. The lock-heads 191 and 192 are shown in a sectional view in the figures; that is, the inside of the lock-heads is visible showing a pawl mechanism in order to clearly convey their orientation and operation. In some embodiments, the lock-heads 191 and 192 may have at least one pawl 205 and 210 respectively. The pawl mechanism may have teeth, or it may be a single flexible beam that interacts with the teeth or other features on the self-locking strap (not shown) such that the pawl flexes or is otherwise biased or spring loaded to deflect towards the self-locking strap that passes through the lock-head. This type of ratchet mechanism is only one example of a one-way locking mechanism, and as noted elsewhere in this disclosure, the locking mechanism may be any device that permits one-way motion while locking in the opposite direction via teeth or other features on the self-locking strap engaging with pawls or other features in the lock-head, or for example, the locking mechanism may be a smooth strap that is gripped by a spring-loaded beam, tine, wedge, or cam inside of the lock-head. The lock-heads 191 and 192 may have the same mechanism as the lock-head of the self-locking strap.

Figure 13B:
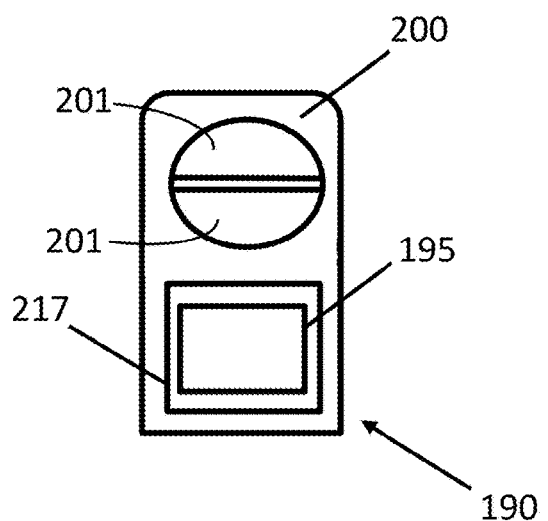

The plunger 197 is free to translate along the inner core 195, and it may be biased with a return spring 193 such that, in its resting position, the two lock-heads 191 and 192 are adjacent to each another as shown in FIG. 13A. An elongate tube 199 lies distal to the stationary lock-head 191, in line with the inner channels of both lock-heads 191 and 192; the elongate tube 199 may be connected to a frame 200 that slides along the inner core 195 of the device 190. A gauge spring 194 is situated between the frame 200 and the stationary lock-head 191 in order to provide a gauge to measure the tension exerted being pulled on the self-locking strap. The distal end of the inner core 195 may have an enlarged section, tabs, or boss that retains the frame from sliding off the inner core as it is generally loaded by the gauge spring 194 in the distal direction. Or, for example, the inner core 195 may have an inner core stopper 217 attached at its distal end on its outer surface to retain the frame 200 and the elongate tube 199 on the inner core 195. One or more transverse cutting blades 201 may be located near the distal tip and inside of the lumen of the elongate tube 199. When the device is rotated against a stationary indwelling self-locking strap (not shown) the excess strap may be cleanly severed adjacent to the lock-head. An end view of the tensioning device 190 is shown in FIG. 13B wherein the transverse cutting blades 201 can be seen inside of the lumen of the elongate tube 199 which is offset from the inner core 195 by the frame 200. In this embodiment, the sliding members have a square cross-section to prevent relative rotation between them.

Figure 14A:
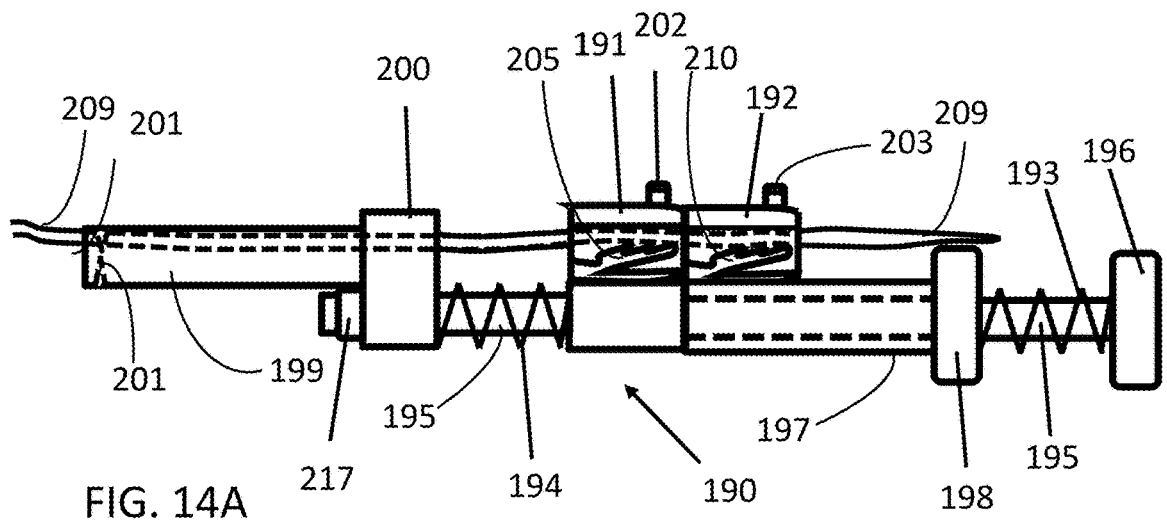
FIGS. 14A-14E illustrate the operation of a strap tensioning device.
Figure 14B:
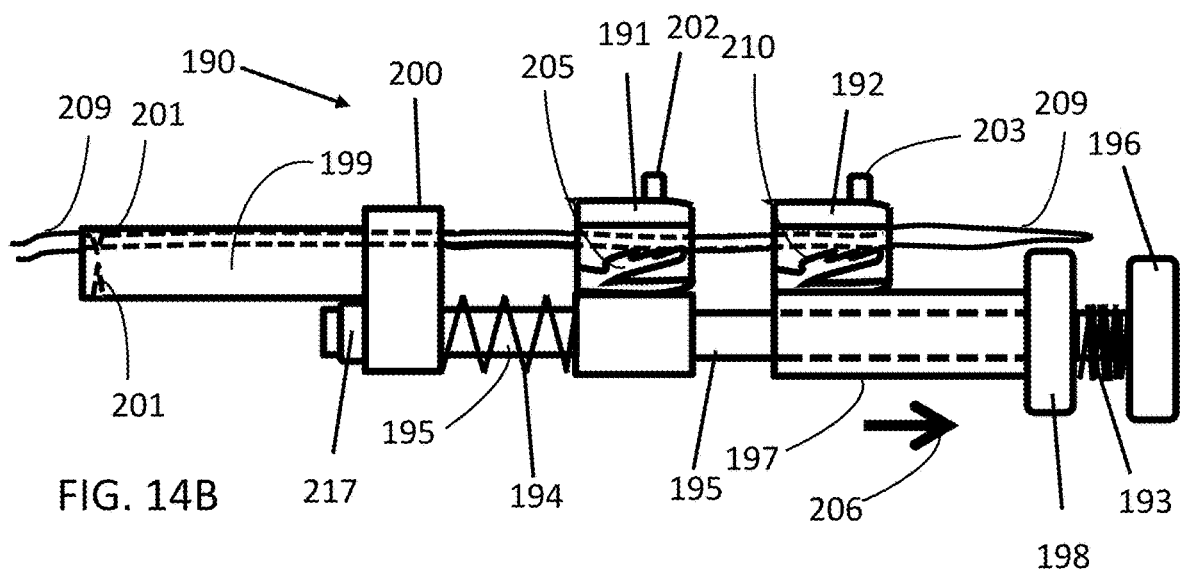
Figure 14C:
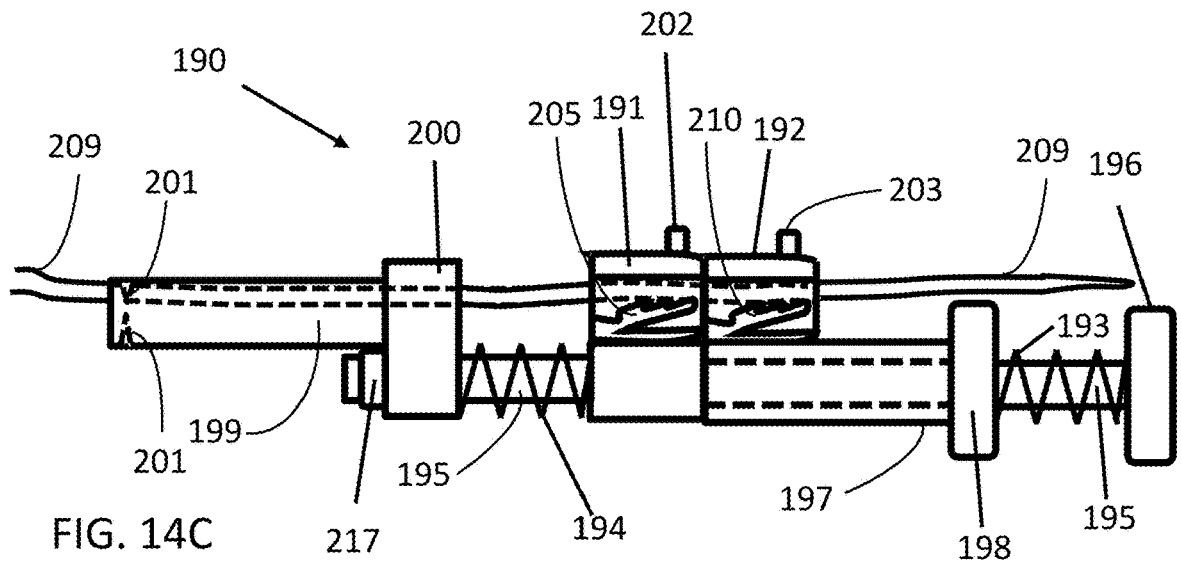

An example of the operation of the tensioning device 190 is illustrated in FIGS. 14A-14E. One end of the self-locking strap 209 is inserted into the distal end of the elongate tube 199 and advanced through both lock-heads 191 and 192, until teeth or other features on the strap 209 engage the pawls 205 and 210 on the lock-heads 191 and 192 (FIG. 14A). As shown in FIG. 14B as the plunger 197 is pulled in the direction of the arrow 206, toward the inner core handle 196, the attached movable lock head 192 pawl 210 move with it, and since the pawl 210 is engaged with the strap 209, the strap is pulled in the direction of the arrow 206 as well. The strap 209 slides through the stationary lock-head 191 freely because the lock-heads 191 and 192 are configured to restrict motion in the direction opposite to the arrow 206. As illustrated in FIG. 14C, when the plunger 197 is released, the movable lock-head 192 slides freely back along the strap 209 to meet the stationary lock-head 191. The stationary lock-head 191 holds the strap 209 in place so that it does not move back out of the elongate tube 199. Repeated depression of the plunger 197 pulls the self-locking strap 209 in lengths equal to the length of excursion of the plunger 197 to advance the strap 209 incrementally. While the self-locking strap 209 is loose on the anatomy, the tensioning device 190 can be held in place while the strap advances through automatically due to the action of the two lock-heads 192 and 191. Once the strap begins to have tension as it tightens around the anatomy, the tensioning device 190 will be pulled down into the body as the surgeon actuates it until the elongate tube 199 contacts the lock-head of the self-locking strap 209.

Figure 14D:
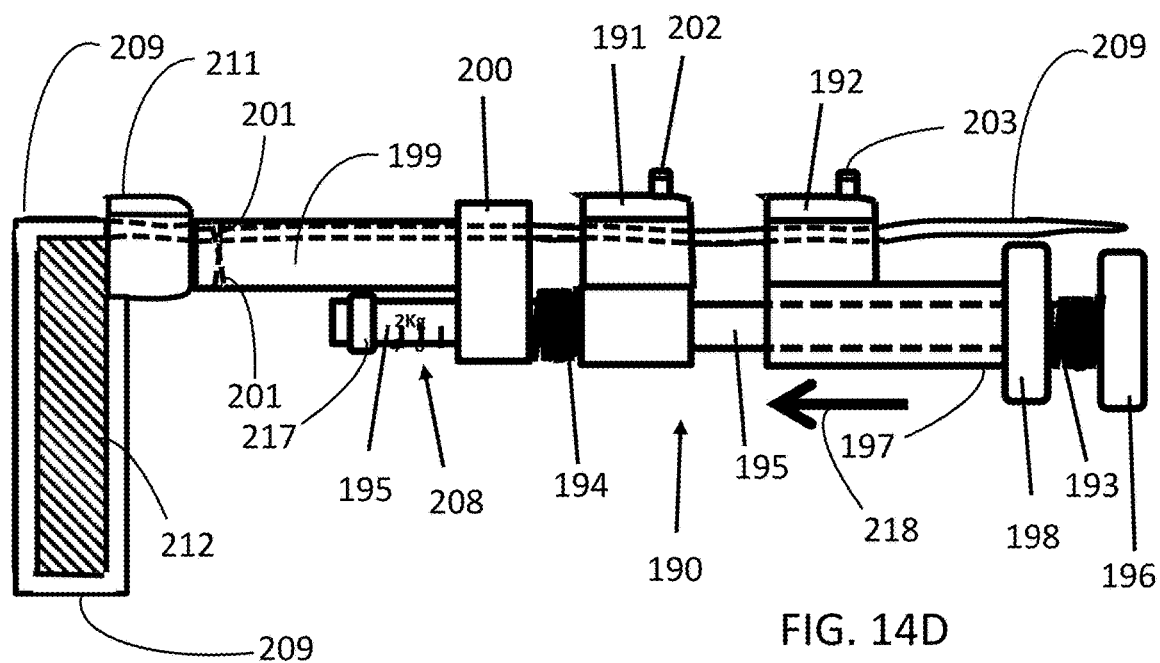
Figure 14E:
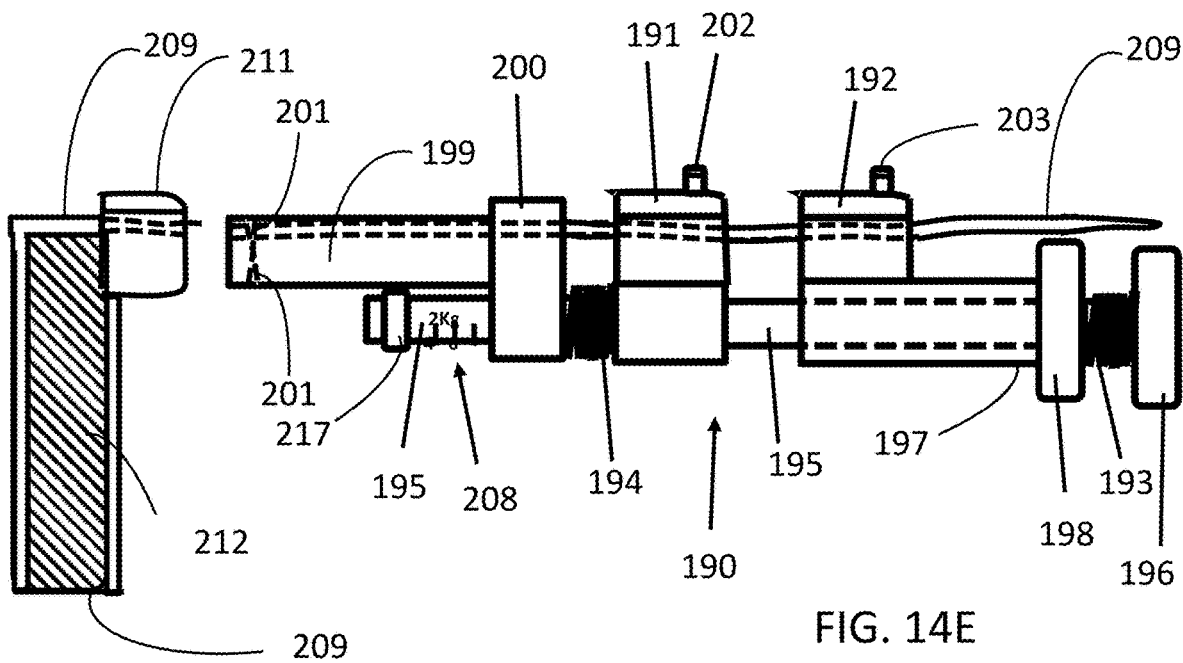

FIG. 14D schematically shows the self-locking strap 209 encircling tissue 212 as it is tensioned. For clarity, the tissue 212 is schematically indicated as a rectangular cross-section which may denote any tissue that is being engaged by the strap such as the rectus abdominus muscle. The tensioning device 190 abuts against the lock-head 211 of the strap 209 during tensioning because the tensioning device 190 is eventually pulled down the strap 209 as it is incrementally tightened. The surgeon depresses the plunger handle 198 in the direction opposite to the arrow 218 to tighten the strap via engagement with the movable lock-head 192 as previously described. When the plunger handle 198 is released, the plunger 197 is free to move in the direction of the arrow 218, that is the movable lock-head 192 will release from the strap 209. However, the stationary lock-head 191 will engage with the strap 209 thus preventing it from slipping back out of the elongate tube 199 and into the body. The strap 209, pulls on the stationary lock-head 191 distally and, since the stationary lock-head 191 is rigidly attached to the inner core 195, the stationary lock-head 191 is pulled with the strap 209 such that it compresses the gauge spring 194. As the gauge spring 194 is compressed, the inner core 195 protrudes from the frame 200 by an amount that is proportional to the force on the gauge spring 194 and hence proportional to the tensile force on the strap 209 because it is the strap 209 that is pulling on the stationary lock-head 191. This force may be displayed via a force readout 208 on the inner core 195. The force readout may be examined by the surgeon during this process to avoid application of excessive tension on abdominal wall tissue during defect closure. Upon completion of strap tensioning, the tensioning device may be rotated to sever the strap 209 at its interface with the lock-head 211 as shown in FIG. 14E.

The lock-heads 191 and 192 on the tensioning device 190 may need to be removed from the self-locking strap 209 after partial tightening of the self-locking straps. This may be necessary during surgeries requiring multiple straps such as in ventral hernia repair so the surgeon can gradually reapose the tissue along the defect. Upon placement of multiple self-locking straps along an abdominal wall defect, the surgeon may tighten an individual strap to a desired degree of tension, as measured by the force readout 208 on the tensioning device 190. The tensioning device 190 may then be removed from the strap 209 and applied to adjacent straps, to close the ventral hernia defect in stages, without exceeding an amount of tension that may cause the strap to cut through abdominal wall tissue during the closure process. The stationary lock-head 191 and the movable lock-head 192 on the tensioning device 190 may contain a release mechanism as shown in FIGS. 15A-15D. The stationary lock-head 191 is shown as an example, however, the same principal may be incorporated into the movable lock-head 192 via its release frame 203 and pawl 210. A release frame 202 may pass through the window 204 and be attached to or abut against the pawl 205 of the stationary lock-head 191. Upon depression of the release frame 202 in the direction of the arrow 213, as shown in FIG. 15C, the pawl 205 moves inferiorly in the direction of the arrow 206 (FIG. 15D) to release the strap positioned inside the lock-head 191.

In order to remove the tensioning device 190 from a strap, the release frames 202 and 203 on both the stationary lock-head 191 and the movable lock-head 192 and 192 may be depressed simultaneously. As shown in FIG. 15E, to facilitate depressing both release frames 202 and 203 simultaneously, a release frame extension 214 may protrude rigidly from one release frame 202 and extend just above the other release frame 203 such that when the release frame extension 214 is depressed in the direction of the arrow 215, both release frames 202 and 203 are depressed, thus releasing the strap (not shown) from both lock-heads 191 and 192. Alternatively, the release frame extension (not shown) may be rigidly mounted to the release frame 202 on the stationary lock-head 191 and extend over the release frame 203 on the movable lock-head 192.

Figure 16A:
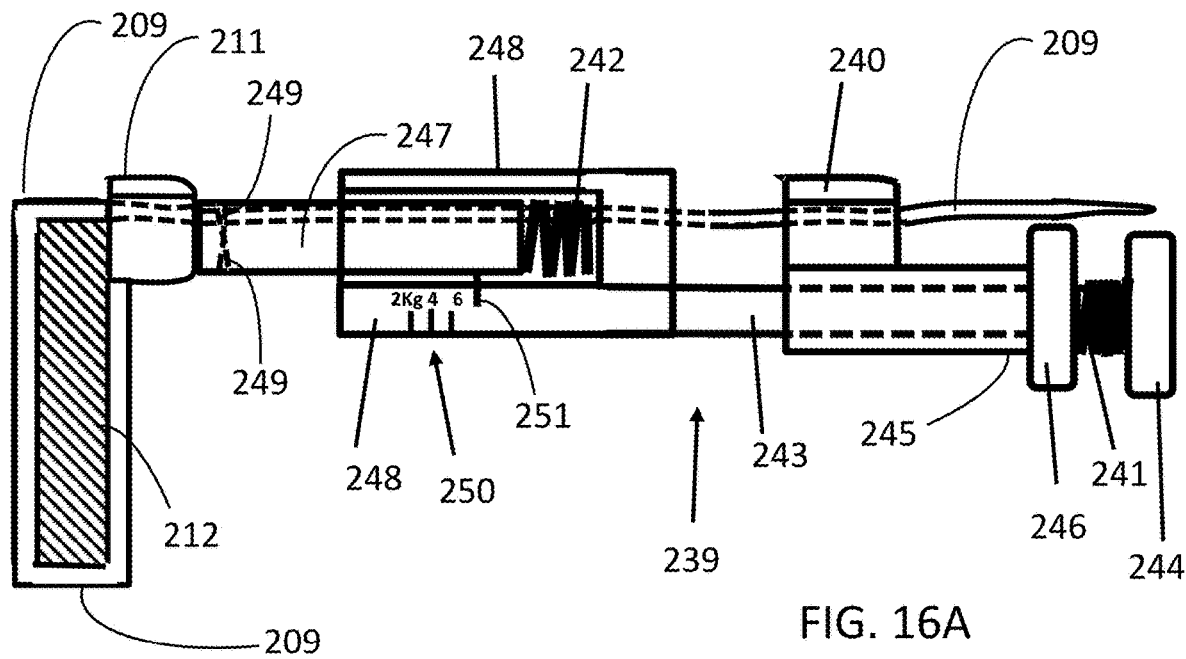
FIG. 16A illustrates another embodiment of a strap tensioning device.

FIG. 16A shows another embodiment of a tensioning device 239 having a lock-head 240 attached to a plunger 245 that slides over an inner core 243. The lock-head may have any type of one-way mechanism including a ratchet/pawl mechanism or, for example, a cam that locks onto the strap when the inner core handle is pulled. The single lock-head may have a ratchet and pawl mechanism, or it may have a cam that engages with the strap 209 when the plunger 245 is pulled via the plunger handle 246 toward the inner core handle 244. A return spring 241 tends to return the plunger 245 and its attached lock-head 240 to release the cam and slide back toward the frame 248 which is fixedly attached to the inner core 243. The lock-head 211 on the self-locking strap 209 prevents the strap from loosening after each pull and release by the plunger 245. An elongate tube 247 slides within the frame 248 and presses on a gauge spring 242 at the proximal end of the elongate tube 247. As the plunger 245 is pulled to tension the strap 209, the inner core 243 and attached frame 248 are pulled against the lock-head 211 of the strap 209 and since the elongate tube 247 abuts the lock-head 211, the gauge spring 242 is compressed. A force indicator 251 attached to the elongate tube 247 translates over a force readout 250 showing a force proportional to the displacement of the gauge spring 242 and hence the compression force in the gauge spring 242. This force correlates to the tension in the strap 209. The strap 209 may be severed by one or more transverse cutting blades 249 located at the distal end of the elongate tube 247 as previously described.

Once skilled in the art will recognize that there are many different types of force transducer that can be integrated into a device used to tighten the strap and such devices and methods are within the scope of the invention(s) disclosed herein. For example, such load cells that may be placed on any member that is mechanically strained, such as the support tube 45, the elongate tube 247 (or 199), the frame 248 (or 200), or the lock-head 240 (or 192). By way of nonlimiting example, suitable load cells may include strain gauges or piezoelectric sensors which transduce strain into an electrical signal. Or, for example, an electromagnetic sensor or a linear displacement sensor such as a potentiometer may be incorporated into the tensioning device 239 such that it measures the displacement of the force indicator 251 and transduces it into an electrical signal. The electrical signals generated may be used to form a digital readout on the device or transmitted by wired or wireless communication (e.g. Bluetooth or Bluetooth LE) to a separate device such as a computer or robotic system.

Various embodiments of a method or technique and instrumentation to place multiple interrupted fastening loops on each side of a hernia defect and to maintain tension in each loop while allowing serial cinching of each loop to reappose the edges of the defect will now be disclosed. The procedures may be performed laparoscopically, via multiple small incisions and trocar ports. The order of steps and components described herein is for illustrative purposes only and is not intended to limit the scope of the invention(s), as various alternative combinations or permutations of the sequence of steps are contemplated. The systems, devices, and methods described can be used to repair a hernia defect and in some instances may be used to repair a hernia using the components separation method (CSM). For example, a laparoscopic CSM may be used when the surgeon desires to shift a fascial opening, which may be offset from the midline, toward the abdominal midline. Once the defect is aligned, the systems and methods described herein may be used to close the defect.

Figure 17A:
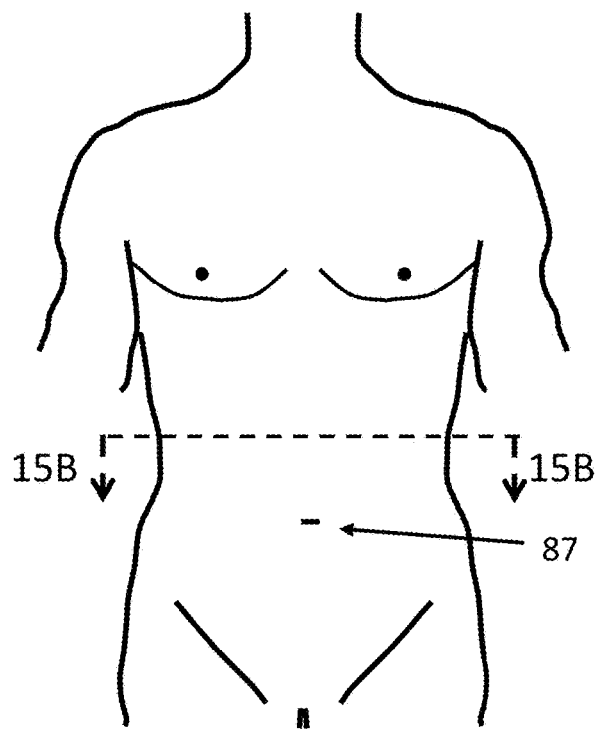
FIGS. 17A-17B illustrate the general anatomical layout for the procedures described herein.
Figure 17B:
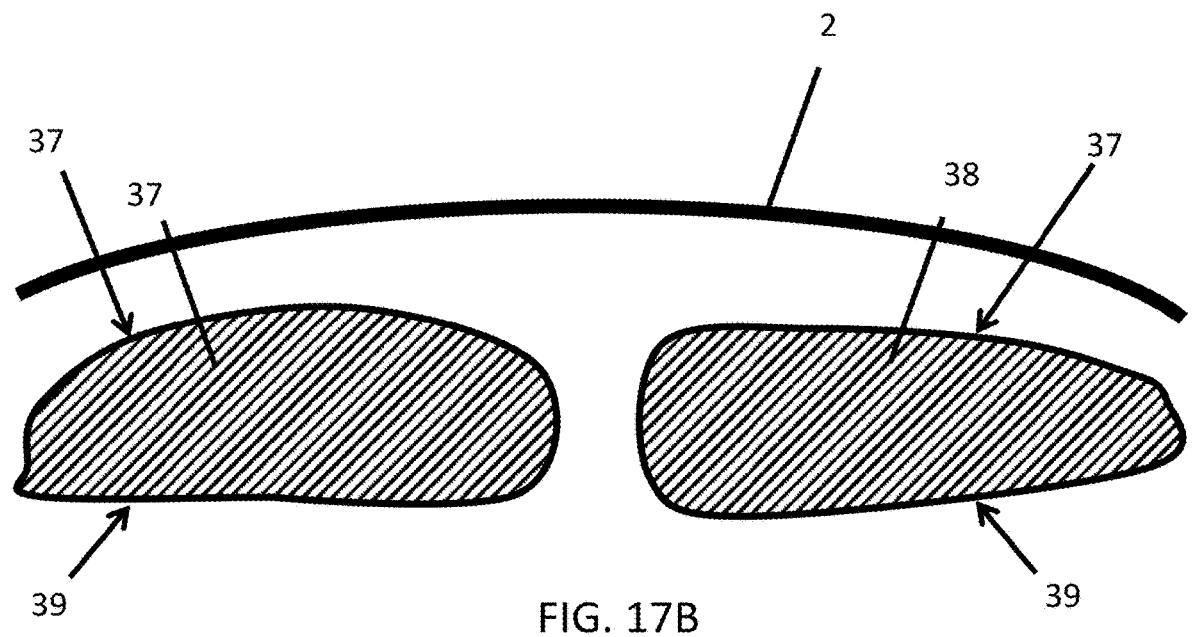

In general, the surgeon may create a small midline incision 87 in the umbilicus, and inserts a Veress needle to insufflate the abdomen with carbon dioxide gas to create a working cavity as shown in FIG. 17A. The Veress needle is removed, and a trocar port is placed at the umbilicus for laparoscope insertion. A second trocar port may be placed lateral to the midline for laparoscopic instrument insertion. One skilled in the art will recognize that there are other surgical and preparation steps for such surgeries. The figures used herein to illustrate the surgical methods are similar to FIG. 17B, which is a cross-section through the human body. The following figures show skin 2, rectus abdominus muscle 38, and fascial tissue 37 and 39, but for clarity, the figures do not show other types of tissue such as muscle, connective tissue, and fat. However, one skilled in the art will recognize that various tissue layers may exist between the skin 2 and the fascial tissues 37 and 39, and the muscle tissue 38. For simplicity, in the method drawings, the self-locking straps are shown without details such as locking features such as teeth.

Figure 18A:
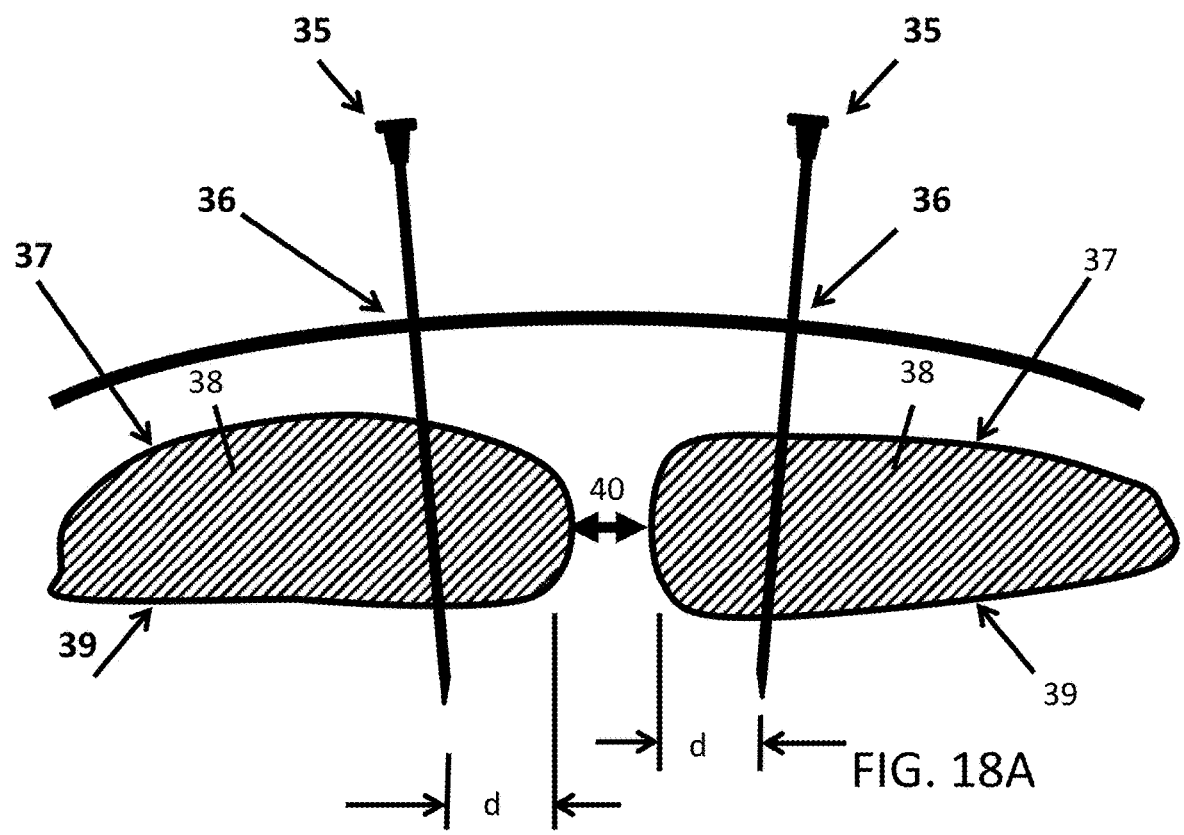
FIGS. 18A-18K illustrate an example of a system used to close a tissue defect.

FIGS. 18A-18K illustrate an example of a defect closure system delivering a strap to the site of a defect and subsequently tensioning the strap in order to close the opening. Turning to FIG. 18A, pilot needles 35 may be inserted through skin entry sites 36, and through the full thickness abdominal wall which consists of the anterior rectus sheath 37, the rectus muscle 38, and the posterior rectus sheath 39 on both sides of a hernia defect 40. The pilot needles 35 may be long (approximately 15 mm or longer depending on the patient's anatomy), such as intravenous or spinal needles, and approximately 18 gauge (1.27 mm diameter). The pilot needles 35 are used to determine the skin entry sites 36 for subsequent needle placement in order to yield a desired tissue margin lateral to the hernia defect 40 (for example d is approximately 2 cm in this embodiment) for subsequent self-locking strap placement. The tissue margin may be directly visualized by an intra-abdominal laparoscope, not shown.

Figure 18B:
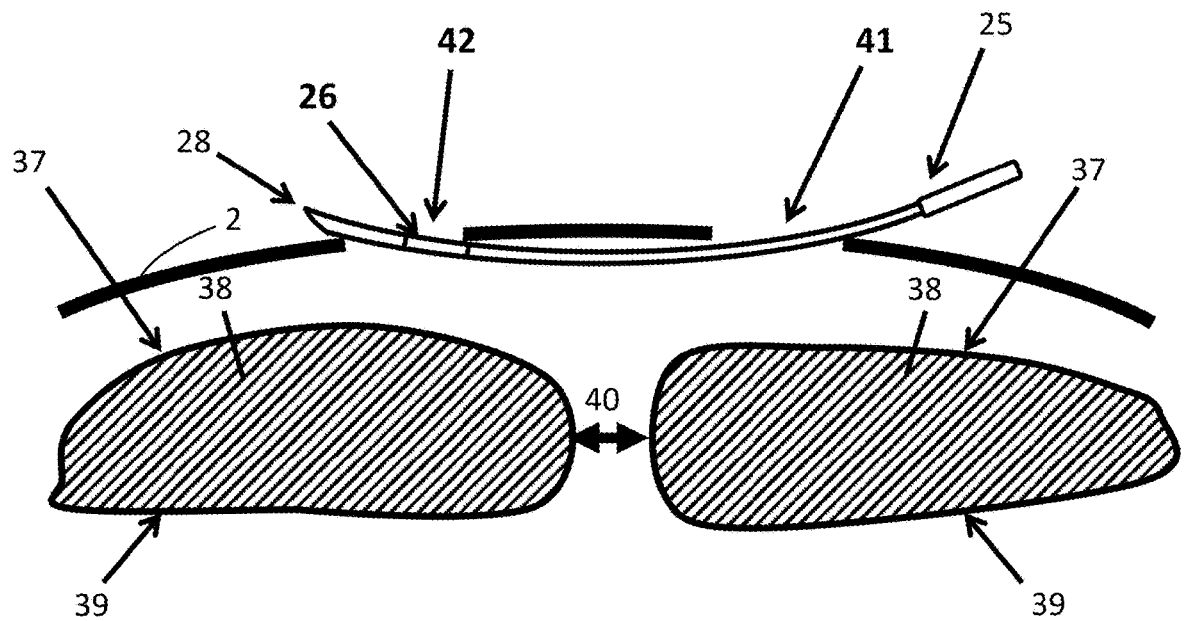

Based on the entry sites of the pilot needles 35, a first skin incision 41 and a second skin incision 42 may be made as shown in FIG. 18B. Skin incisions 41 and 42 may be approximately 3 mm in length and situated at the pilot needle 35 entry sites. Next, the subcutaneous guide 25 is placed which spans from the first skin incision site 41 to a second skin incision site 42 on the opposite side of the hernia defect 40 as it dissects and/or tunnels through the intervening tissue between the incision sites 41 and 42. The subcutaneous guide 25 is advanced until the open portion of the slot 26 appears at the second skin incision site 42. The distal tip 28 of the subcutaneous guide 25 may protrude through the second skin incision site 42 as shown or it may reside below the surface of the skin.

Figure 18C:
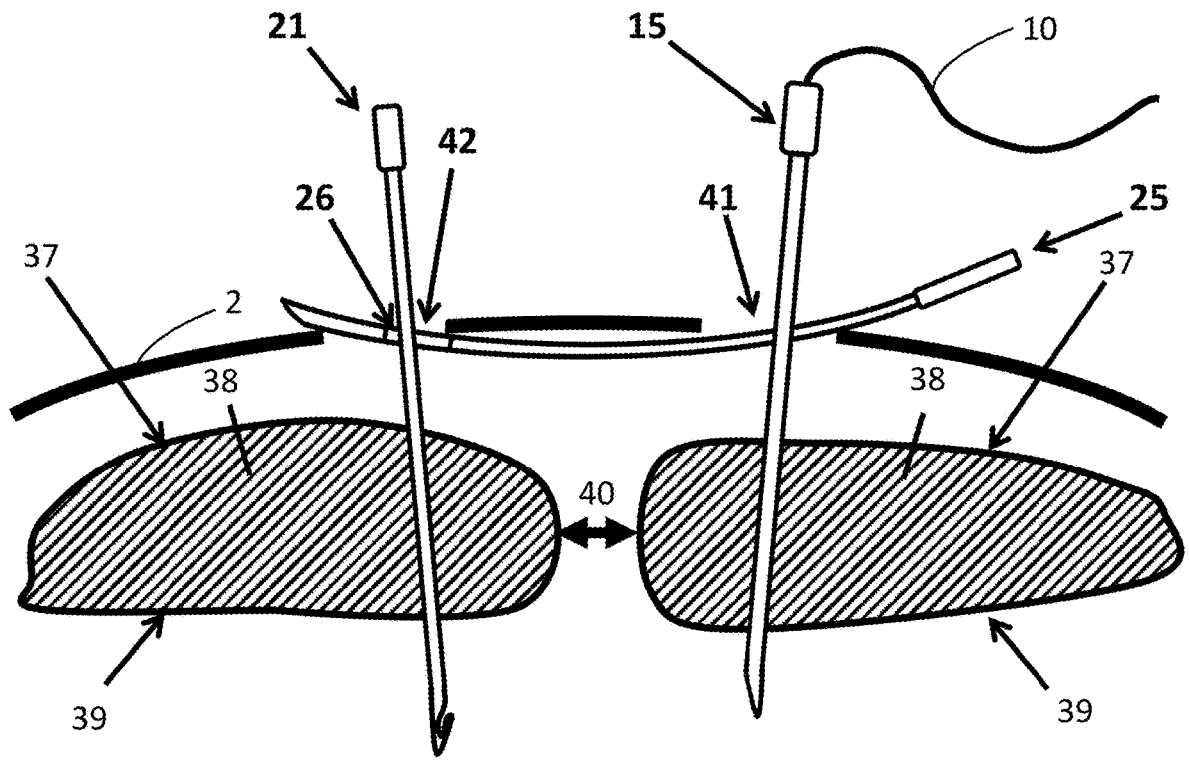

The hook needle 21 may be placed through the distal slot 26 in the subcutaneous guide 25 at the second skin incision site 42 as shown in FIG. 18C. The hook needle 21 may then be advanced through the anterior rectus sheath 37, the rectus muscle 38, and the posterior rectus sheath 39. The slotted needle 15 with the self-locking strap 10 within its lumen may be placed through the first skin incision site 41 and adjacent to the subcutaneous needle guide 25. Once the slotted needle 15 is in place, the self-locking strap 10 may be advanced through the slotted needle 15 into the body cavity. Placing the self-locking strap 10 into the body cavity via the slotted needle 15 avoids the use of another device and potentially another skin entry site to introduce the strap 10 into the body.

Figure 18D:
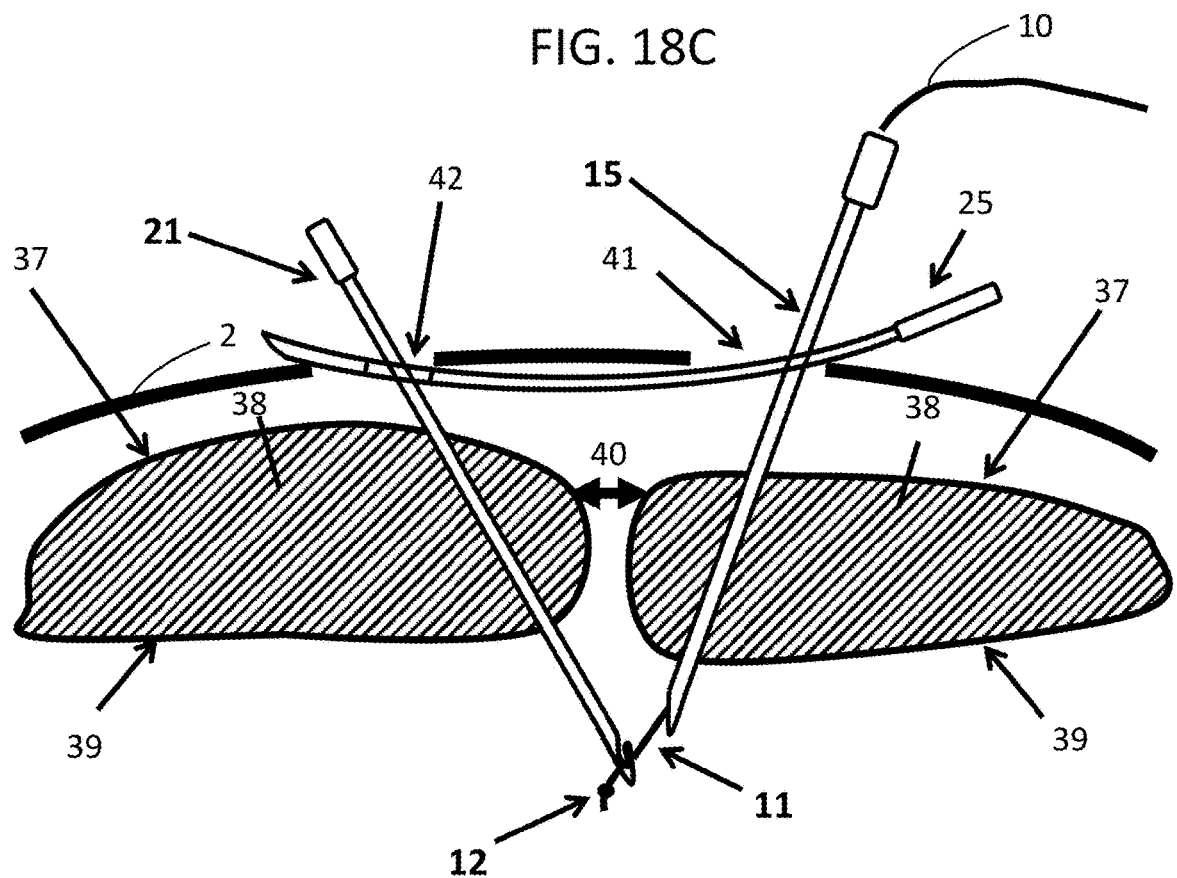

In order to pull the self-locking strap 10 through the opposing muscle, it may be engaged by the hook needle 21. FIG. 18D shows the slotted needle 15 and hook needle 21 being manually angled to bring their distal tips close together. The self-locking strap 10 is then advanced out of the slotted needle 15, exposing the protuberance 12 at the distal end 11 allowing the hook needle 21 to hook the distal end 11 proximal to protuberance 12. Alternatively, a laparoscopic grasper (not shown) may be introduced into the body cavity through another access site; with the grasper, the surgeon may manually grasp the self-locking strap 10 and attach it to the hook needle 21. One skilled in the art will recognize that there may be other features such as a loop or hole on the end of the self-locking strap 10 that may be grasped by the hook needle 21, or the hook needle 21 may have grasping features such as a snare, or clamp, or jaws near its distal tip to hold onto any portion of the self-locking strap 10 regardless of whether or not the self-locking strap 10 has grasping features.

Figure 18E:
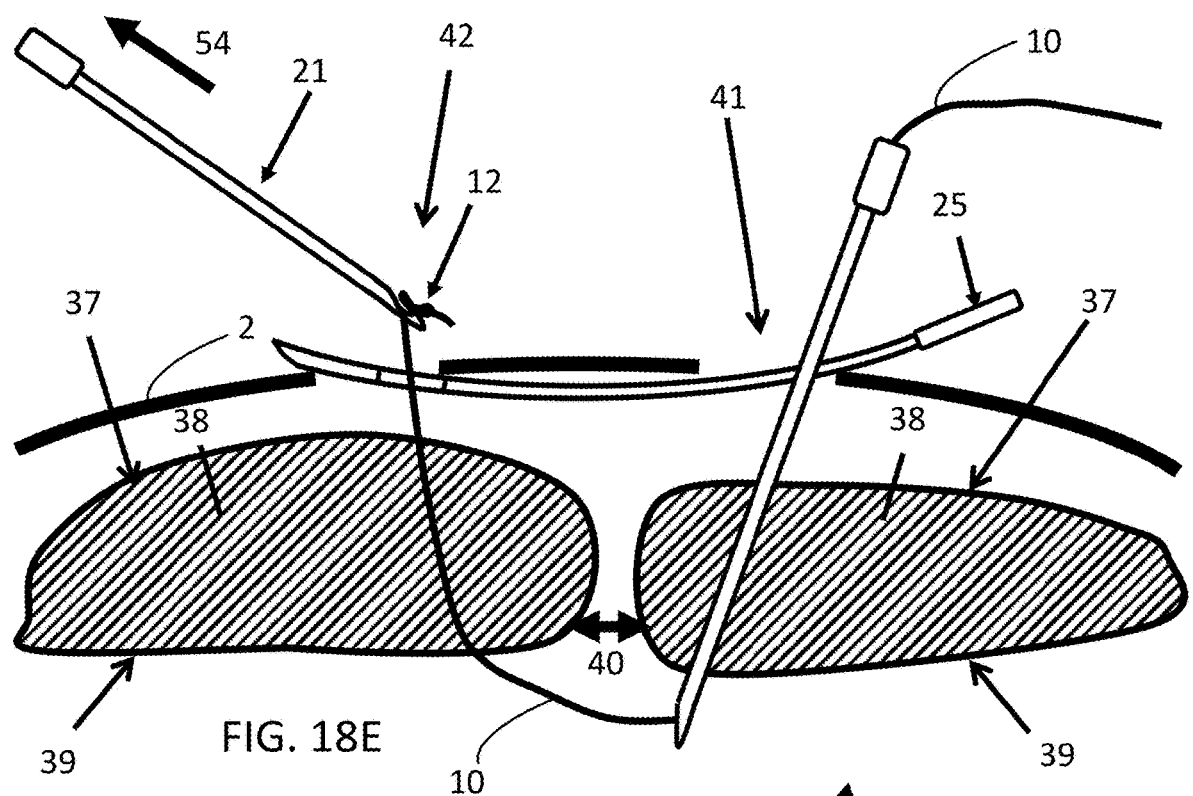
Figure 18F:
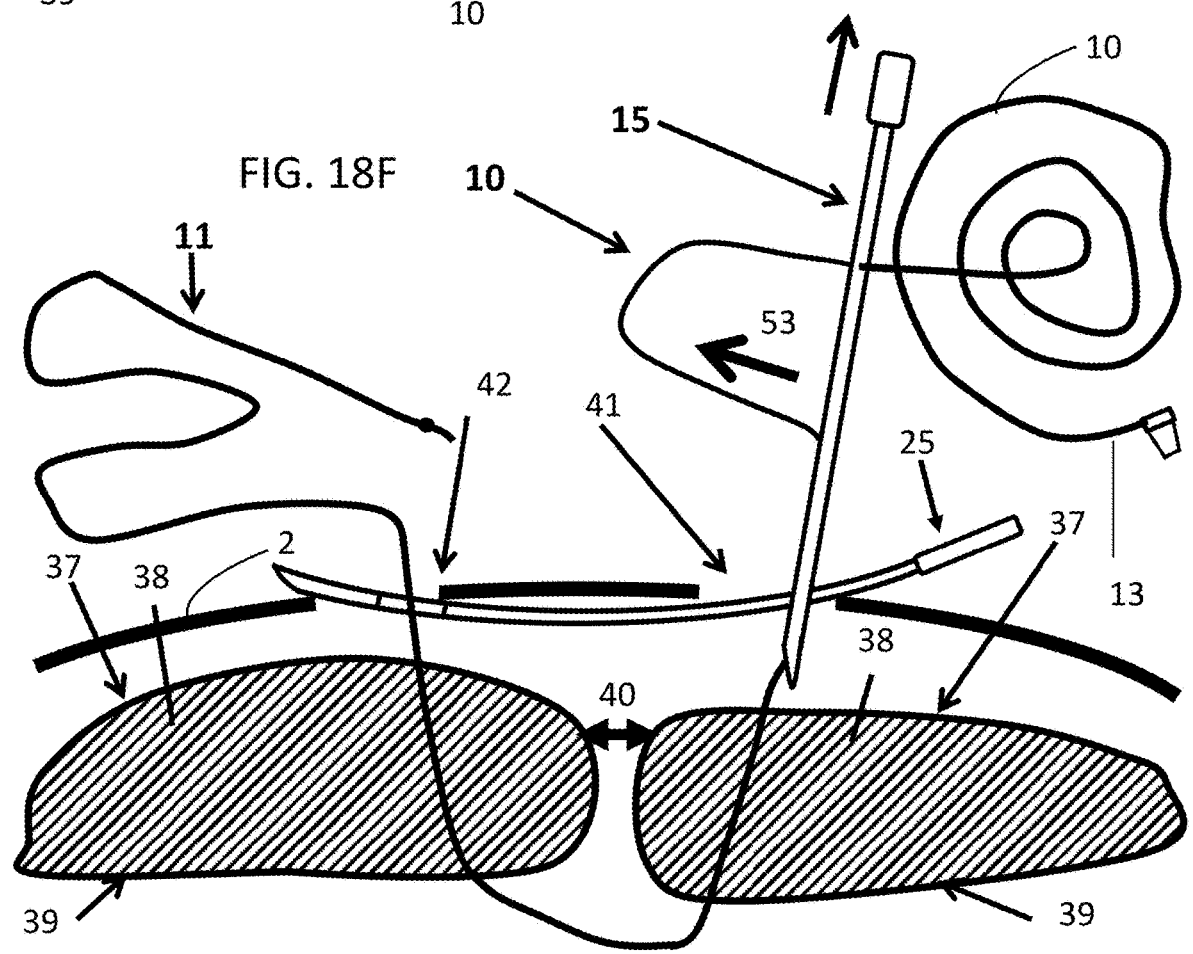
Figure 18G:
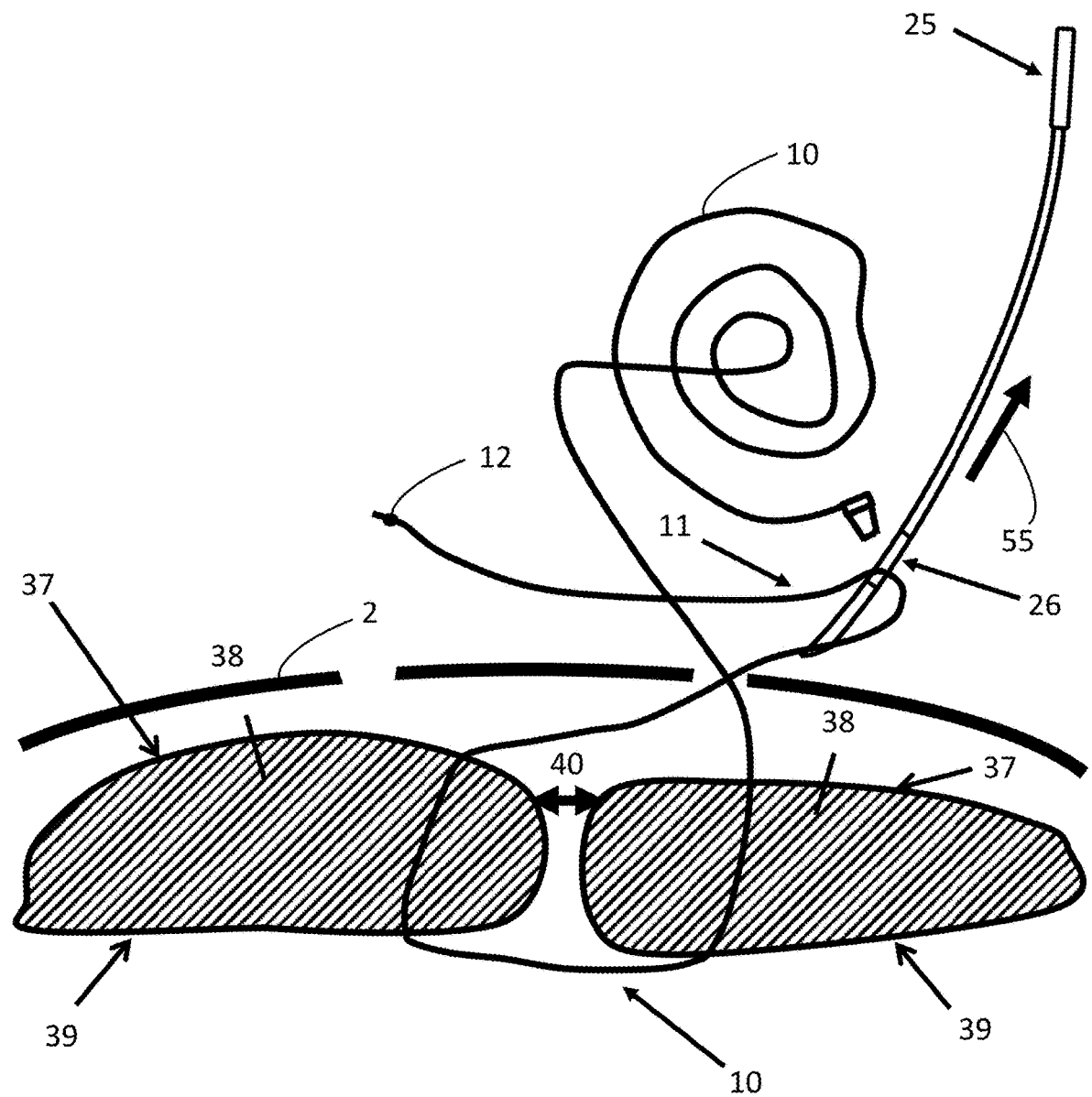

FIG. 18E shows the hook needle 21 being retracted from the patient's body as indicated by arrow 54, thereby also pulling the self-locking strap 10 out of the body at the second skin incision site 42 because the self-locking strap 10 is captured by the hook needle 21. Since the hook needle 21 was placed through the distal slot 26 in the subcutaneous guide 25, as it exits through the distal slot 26 the self-locking strap 10 is also pulled through the slot 26 leaving it captured by the subcutaneous guide 25. Both ends of the strap are now out of the body through the first skin incision site 41 and the second skin incision site 42 as shown in FIG. 18F. The slotted needle 15 may be withdrawn from the body, and then the self-locking strap 10 may be peeled away from the needle 15 and out of its lumen, as indicated by the arrow 53.

Figure 18H:
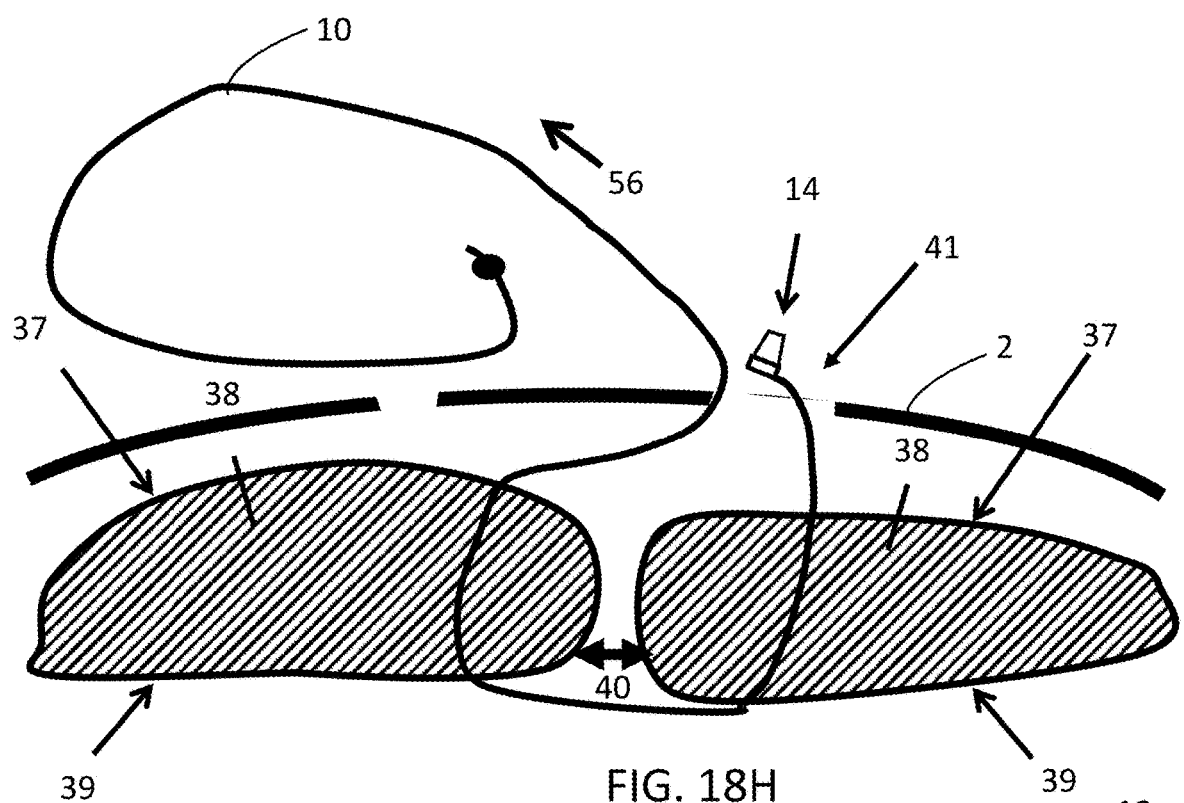

In order to fasten the self-locking strap 10, both ends of the self-locking strap 10 should exit from, or at least be accessible from, the same skin incision so that the strap will reside entirely inside of the body. This may be accomplished by withdrawing the subcutaneous guide 25 from the patient's body through the first skin incision site 41 as indicated by arrow 55 in FIG. 18G. Since the distal end 11 is positioned through the distal slot 26 in the subcutaneous guide 25, the distal end 11 is also pulled out of the body through the first skin incision site 41 leaving the self-locking strap 10 placed through the rectus muscle 38 and across the hernia defect 40 with both ends of the self-locking strap 10 exiting the body so that the self-locking strap 10 may be tightened. This configuration is shown in FIG. 18H where traction may be applied to the self-locking strap 10, indicated by arrow 56, to pull it through the full thickness abdominal wall on both sides of the hernia defect 40 and out of the first skin incision site 41. Since the lock-head 14 protrudes outside of the body near the first skin incision site 41, the distal end of the self-locking strap 10 may be placed through the lock-head 14 for one-way tightening.

Figure 18I:
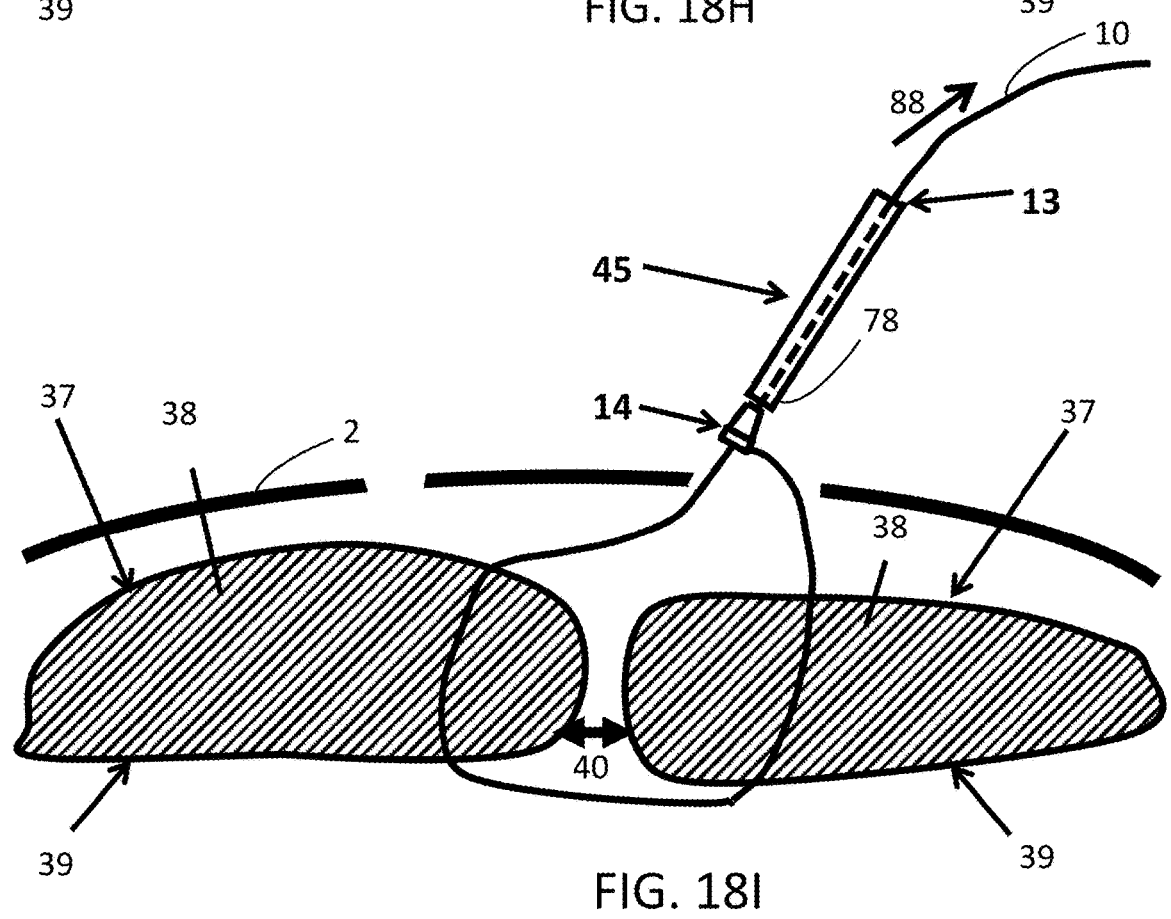

FIG. 18I shows the self-locking strap 10 in the locked configuration as it is being tightened, as indicated by the arrow 88. A support tube 45 may be advanced over the self-locking strap 10 such that the self-locking strap 10 extends through its lumen and the distal end 78 of the support tube 45 may be placed in contact with lock-head 14 to provide counter-traction during the tightening process. Thus, the surgeon may pull on the self-locking strap 10 as indicated by the arrow 57 while pushing on the support tube 45 in the opposite direction. The support tube 45 may be a tubular device made of any material such that it is strong enough to withstand the tension pulled on the self-locking strap 10, such as a rigid polymeric material such as polycarbonate or nylon or a metal, for example, stainless steel.

Figure 18J:
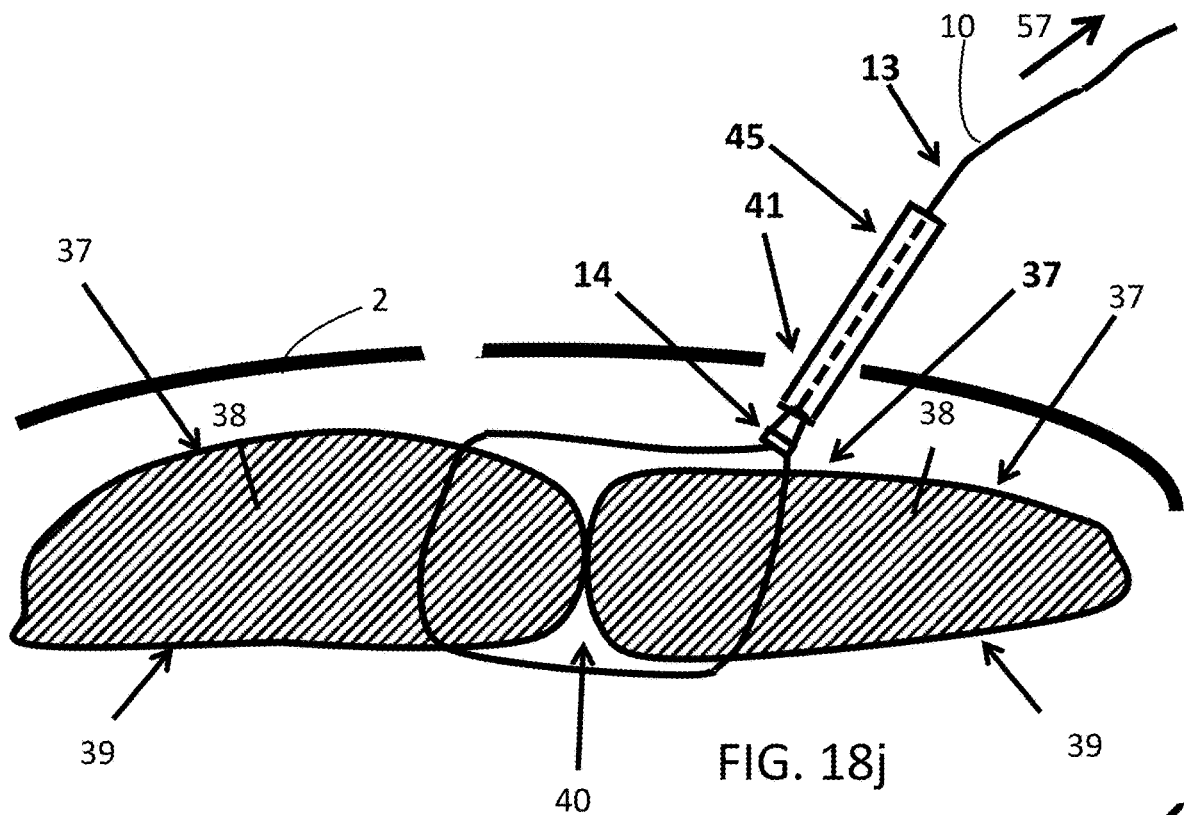
Figure 18K:
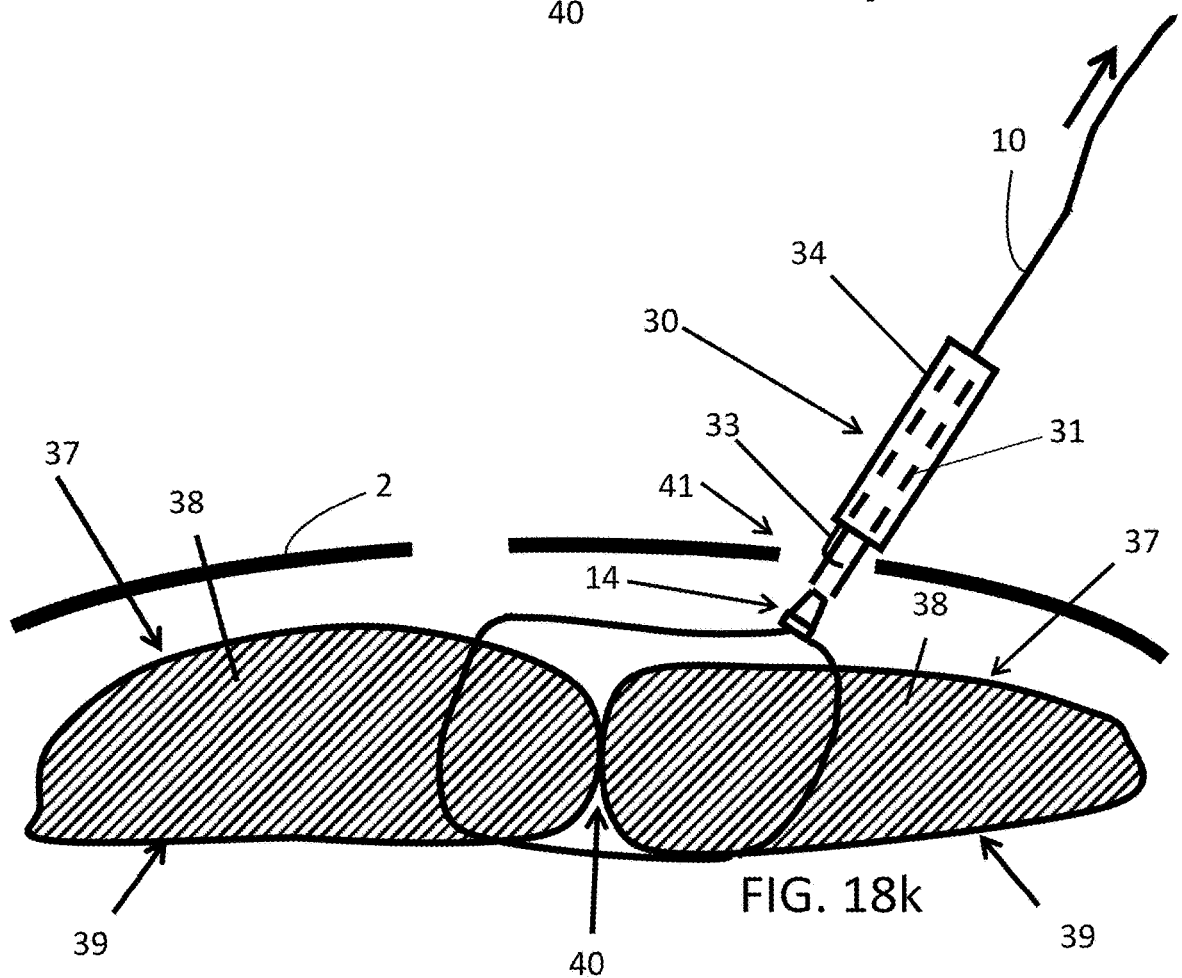

FIG. 18J illustrates the self-locking strap 10 being fully tightened to close the ventral hernia defect 40 as it is pulled in the direction indicated by arrow 57. The support tube 45 may push the lock-head 14 through the first skin incision site 41 and into contact with anterior rectus sheath 37 upon closure of the hernia defect to seat the self-locking strap 10 firmly in place. The excess length of self-locking strap 10 may be removed by any appropriate method or tool. For example, and with reference to FIG. 18K, the tubular cutter 30 may be advanced down the self-locking strap 10 through first skin incision site 41 to contact the lock-head 14, at which point the outer tube 34 may be advanced down over the inner tube 31 causing the cutting blade 33 to flex toward the self-locking strap 10 thus cutting excess self-locking strap 10. In other embodiments, other devices such as the rotational cutter 175 (not shown) may be used to sever the excess strap. Furthermore, the tubular cutter 30 or the rotational cutter 175 may also be used in place of the support tube 45 to both tighten the strap and sever the excess length. It will be apparent to one skilled in the art that there are other alternative methods of cutting excess strap without departing from the inventions disclosed herein. Such methods may include snipping the excess toothed self-locking strap 10 with a scalpel, scissors, or forceps, by way of non-limiting example.

Yet another embodiment of a system and method for approximating full-thickness abdominal tissue is illustrated in FIGS. 19A-19K which illustrate an example of a defect closure system delivering a strap to a site of a defect and subsequently tensioning the strap in order to close the opening. The system 6 incorporates a self-locking strap having a separate lock-head allowing the strap to be introduced into the body through a small, conventional needle. Following strap placement into the abdominal cavity, the needle may be withdrawn from the patient's body without the additional step of peeling the strap out of a slotted needle. This method may also be possible with the use of a strap having an attached lock-head if the size of the lock head fits into a small needle. The system 6 may comprise by way of non-limiting example, a self-locking strap 100, a strap insertion needle 7, a hook needle 21, a subcutaneous guide 164, a laparoscopic grasper 73, and a support tube 45. Other components and devices, including those disclosed throughout this application may be included in the systems and used in the methods disclosed herein, i.e. the system 6 shown is not necessarily a complete surgical kit and other devices and methods may be substituted or added to the system 6 to form other systems or embodiments that are within the scope of the invention(s) disclosed herein. For example, a strap cutting instrument may be included as well as various laparoscopic instruments, such as a laparoscope with a camera may also be used during the surgery Now with reference to FIG. 19A, pilot needles 35 may be inserted through skin entry sites 36, and through the full thickness abdominal wall which consists of the anterior rectus sheath 37, the rectus muscle 38, and the posterior rectus sheath 39. The pilot needles 35 may be long (approximately 15 mm), such as intravenous or spinal needles, and approximately 18 gauge (1.27 mm diameter). The pilot needles 35 are used to determine the skin entry sites 36 for subsequent needle placement in order to yield a desired tissue margin lateral to the hernia defect 40 (for example d=2 cm in this illustration) for subsequent self-locking strap 100 placement. The tissue margin may be directly visualized by an intra-abdominal laparoscope, not shown.

Figure 19A:
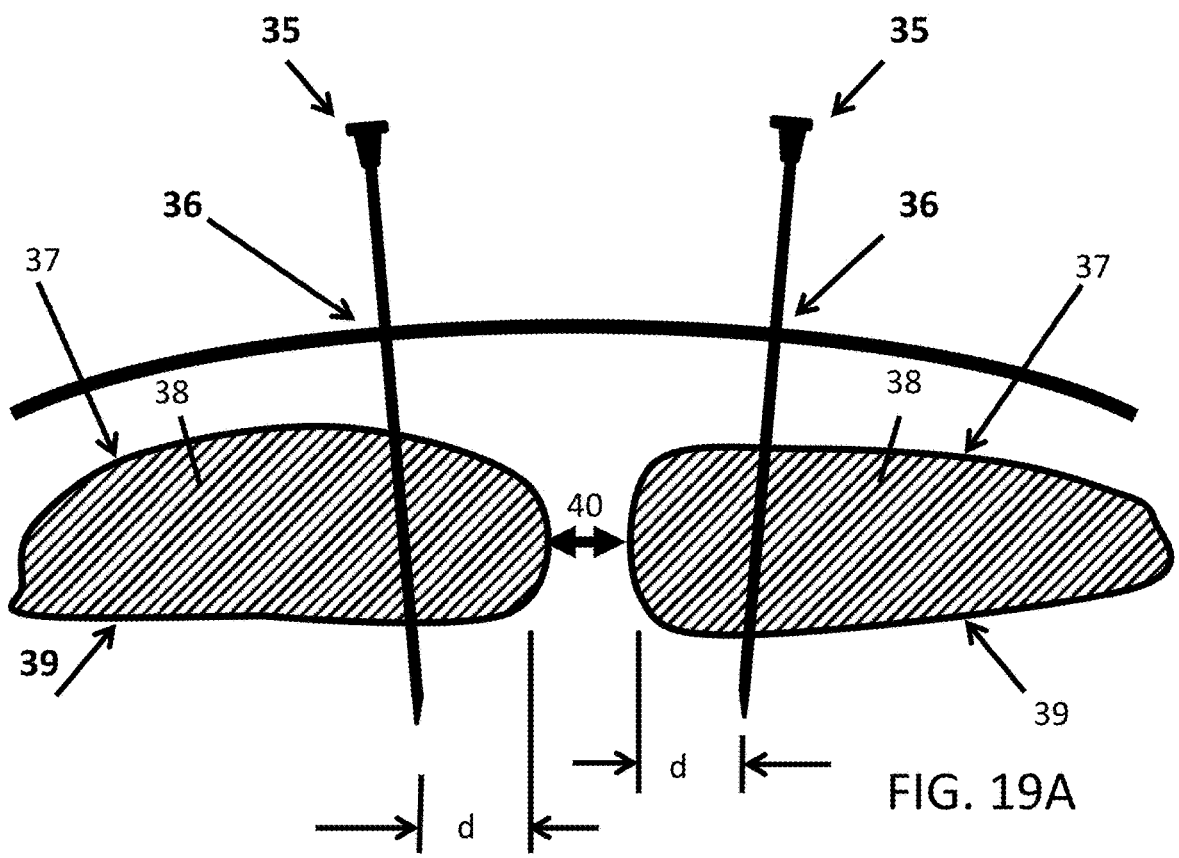
FIG. 19A-19K illustrates another embodiment of a system for closing a defect in tissue.
Figure 19B:
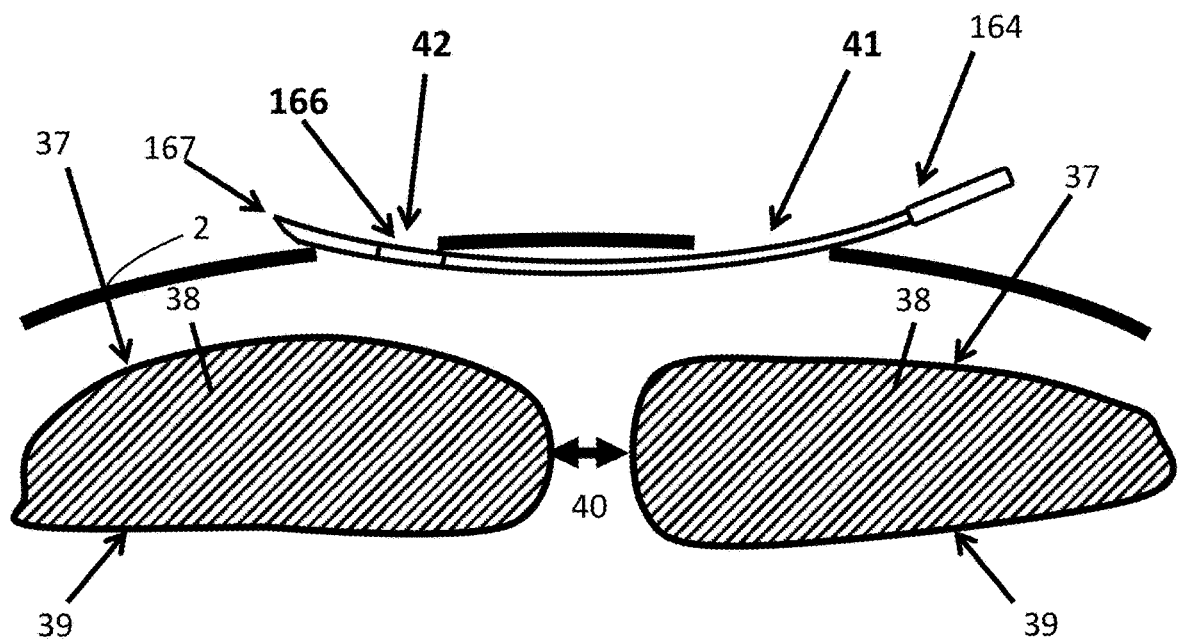

Based on the entry sites of the pilot needles 35, a first skin incision 41 and a second skin incision 42 may be made as shown in FIG. 19B. Skin incisions 41 and 42 may be approximately 3 mm in length and situated at the pilot needle 35 entry sites. Next, the subcutaneous guide 164 is placed which spans from the first skin incision site 41 to a second skin incision site 42 on the opposite side of hernia defect 40 as it dissects and/or tunnels through the intervening tissue between the incision sites 41 and 42. The subcutaneous guide 164 is advanced until the open portion of the slot 166 appears at the second skin incision site 42. The distal tip 167 of the subcutaneous guide 164 may protrude through the second skin incision site 42 as shown or it may reside below the surface of the skin.

Figure 19C:
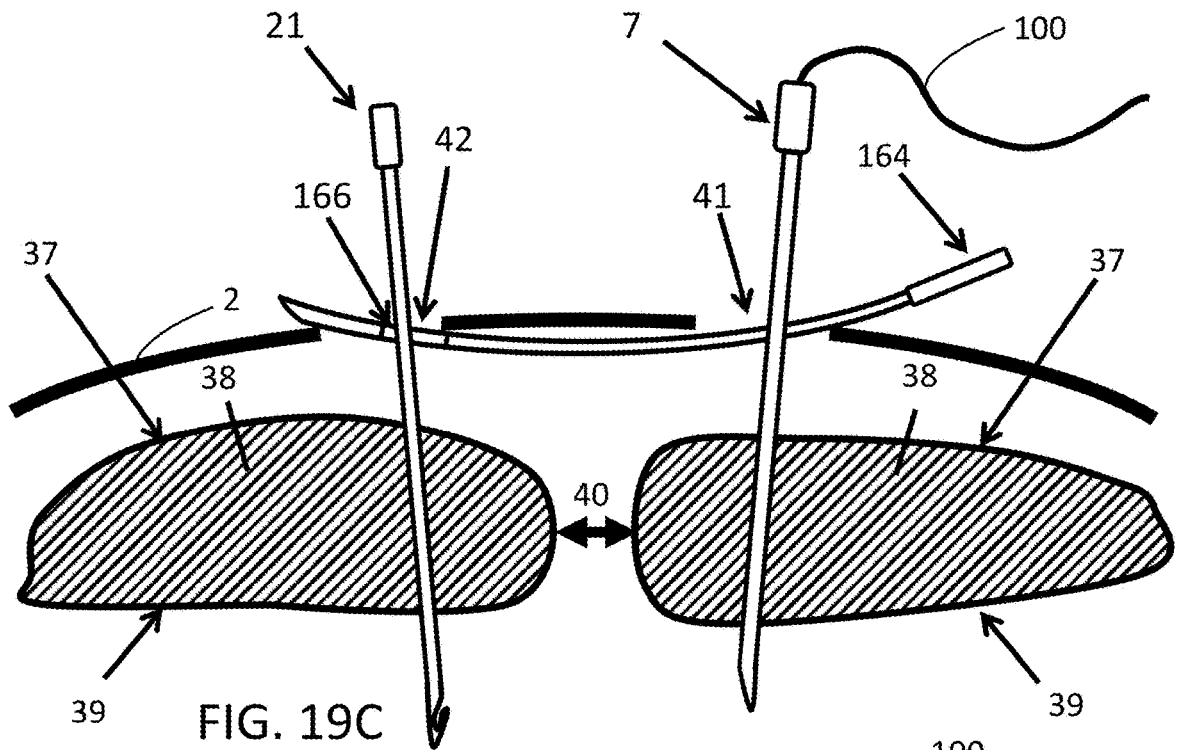

The hook needle 21 may be placed through the distal slot 166 in the subcutaneous guide 164 at the second skin incision site 42 as shown in FIG. 19C. The hook needle 21 may then be advanced through the anterior rectus sheath 37, the rectus muscle 38, and the posterior rectus sheath 39. The strap insertion needle 7 with the self-locking strap 100 within its lumen may be placed through the first skin incision site 41 and adjacent to the subcutaneous guide 164. Once the strap insertion needle 7 is in place, the self-locking strap 100 may be advanced through the strap insertion needle 7 into the body cavity. For simplicity, the self-locking strap 100 is shown schematically as a line without details such as locking features such as teeth.

Figure 19D:
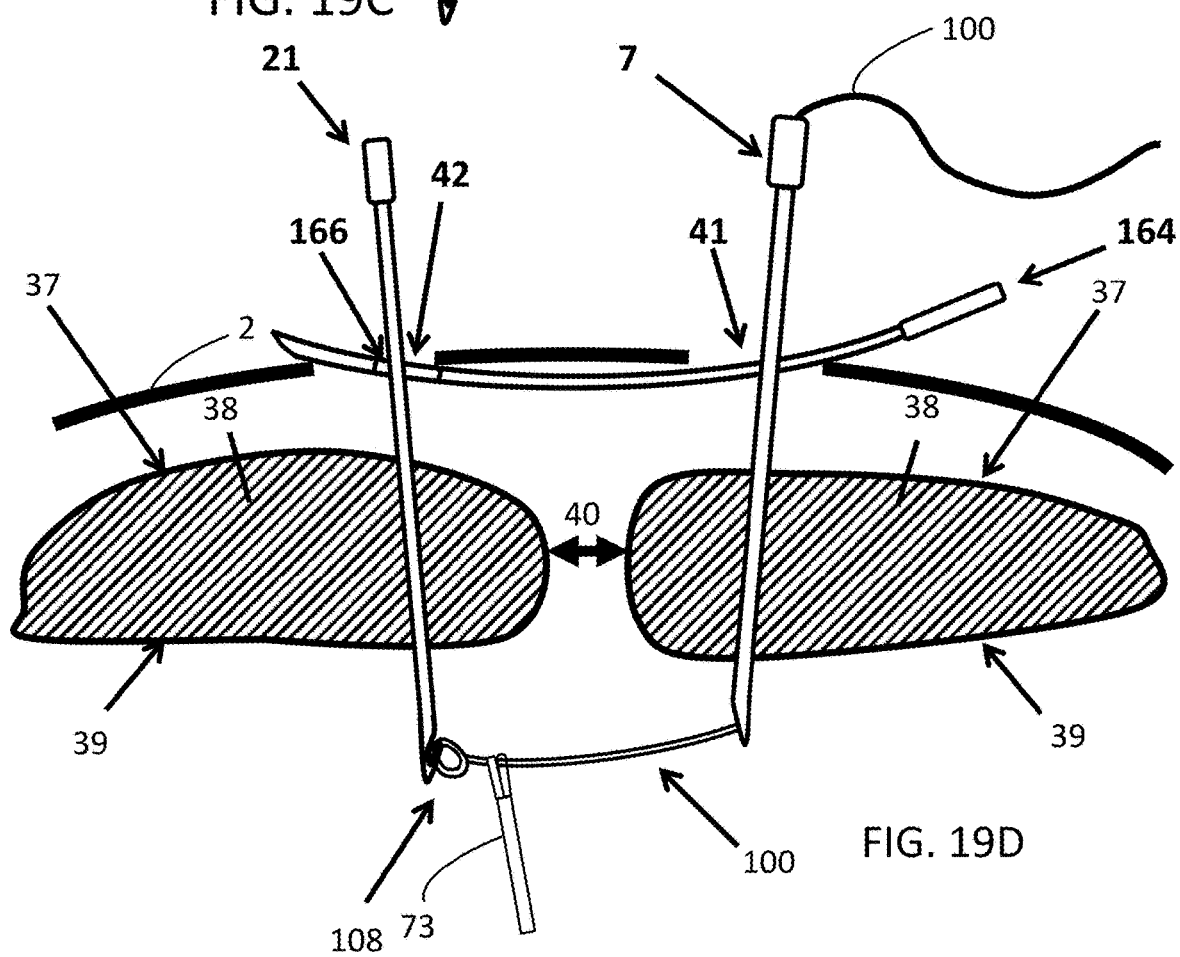

In order to pull the strap 100 through the opposing muscle, it may be picked up by the hook needle 21; if the distal tips of the hook needle 21 and strap insertion needle 7 are close together inside the body cavity, they may be manipulated such that the hook needle 21 engages with the strap 100 or a distal feature on the strap such as the distal aperture 108. Alternatively, as shown in FIG. 19D, a laparoscopic grasper 73 may be introduced into the body cavity through another access site; with the grasper 73, the surgeon may manually grasp the strap 100 or the distal aperture 108 and attach it to the hook needle 21. Only the distal end of the grasper 73 is shown. One skilled in the art will recognize that there may be other features such as a loop, hook, or protuberance on the end of the strap 100 that may be grasped by the hook needle 21, or the hook needle 21 may have grasping features such as a snare, or clamp, or jaws near its distal tip to hold onto any portion of the strap 100 regardless of whether or not the strap 100 has engagement features.

Figure 19E:
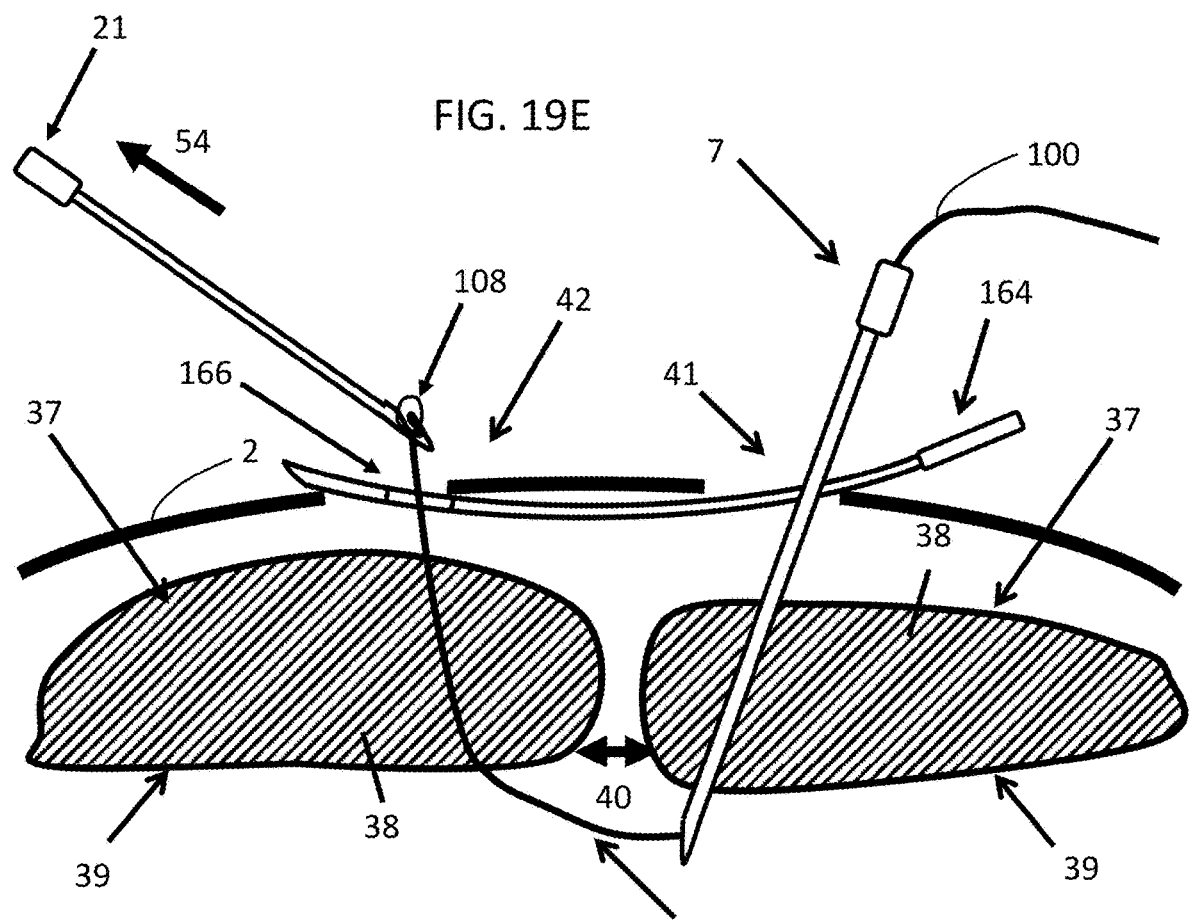
Figure 19F:
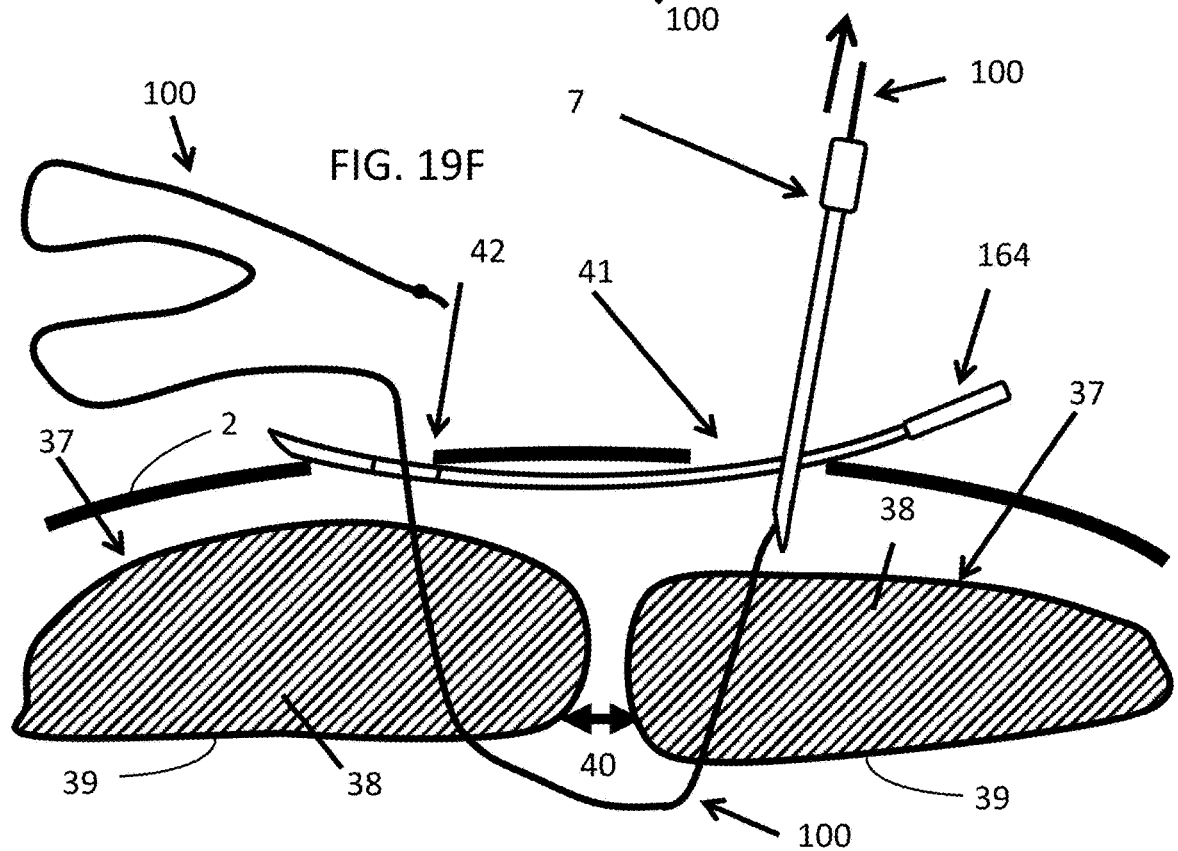
Figure 19G:
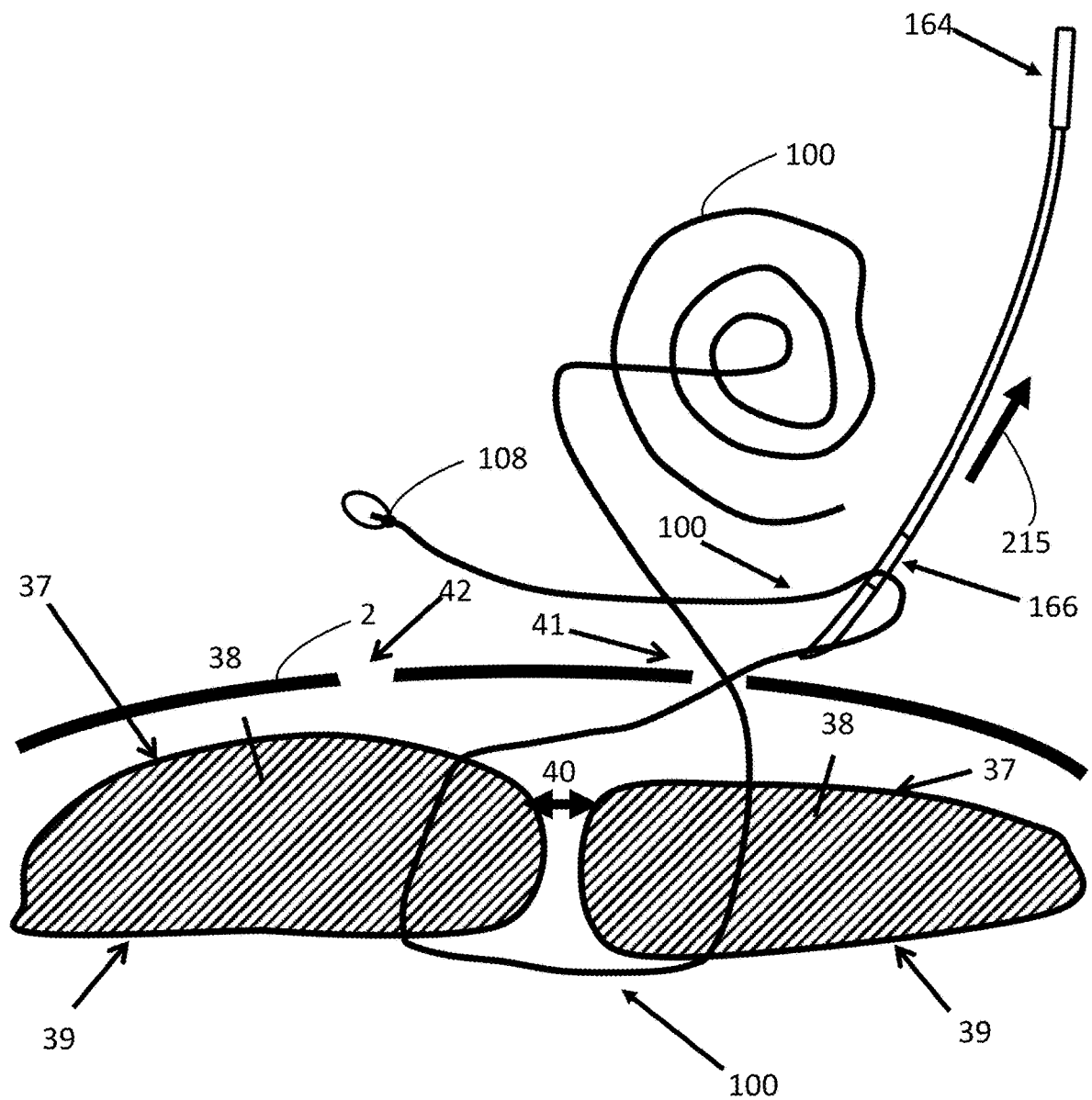

FIG. 19E shows the hook needle 21 being pulled out of the patient's body as indicated by arrow 54, thereby pulling the self-locking strap 100 out of the body at the second skin incision site 42 as the strap 100 is captured by the hook needle 21. Since the hook needle 21 was placed through the distal slot 166 in the subcutaneous guide 164, as it exits through the distal slot 166 the strap 100 is also pulled through the slot 166 leaving it captured by the subcutaneous guide 164. Both ends of the strap are now out of the body, the distal end of the strap through the first skin incision site 41 and the proximal end of the strap through the second skin incision site 42 as shown in FIG. 19F. The strap insertion needle 7 may be withdrawn from the body and withdrawn over the strap 100 leaving the strap exiting through the first skin incision site 41 without the strap insertion needle 7.

Figure 19H:
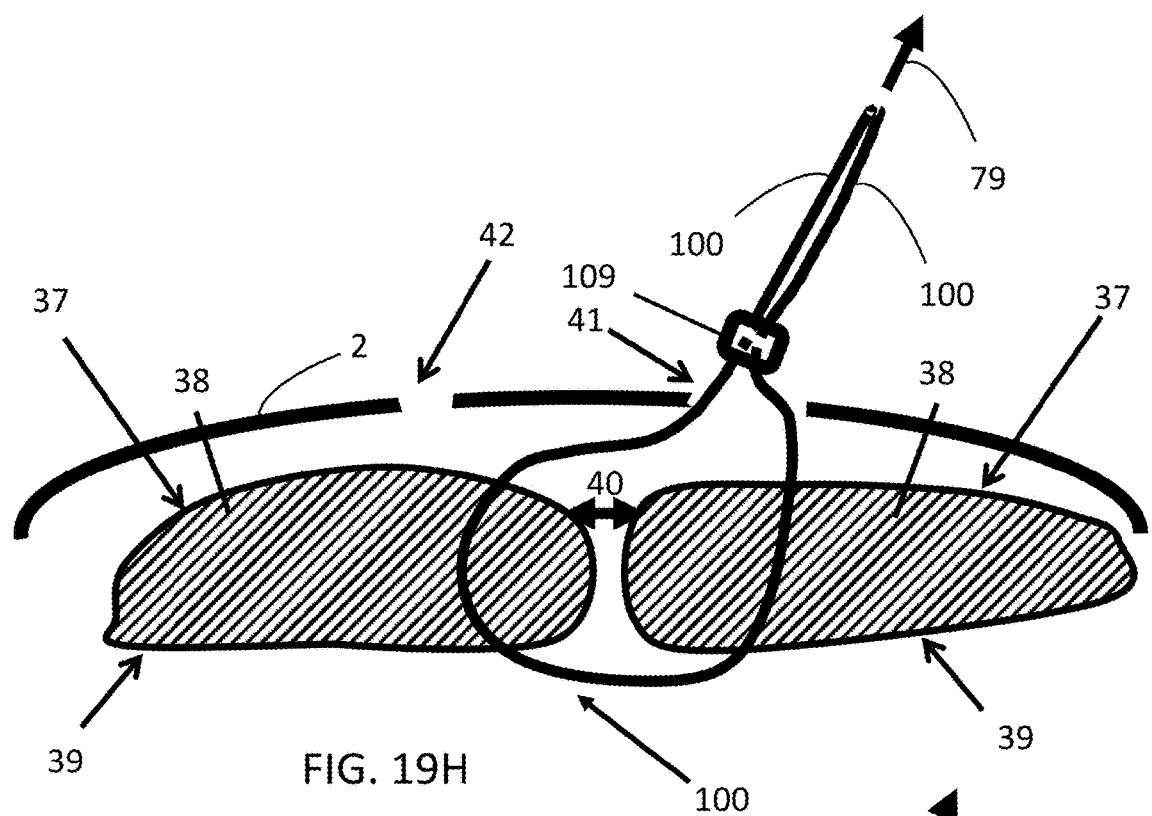

In order to fasten the self-locking strap 10, both ends of the strap 100 should exit from, or at least be accessible from, the same skin incision. This may be accomplished by withdrawing the subcutaneous guide 164 from the patient's body through the first skin incision site 41 as indicated by arrow 215 in FIG. 19G. Since the self-locking strap 10 is positioned through the distal slot 166 in the subcutaneous guide 164, the self-locking strap 100 is also pulled out of the body through the first skin incision site 41 leaving the self-locking strap 100 placed through the rectus muscle 38 and across the hernia defect 40. With both ends of the strap 100 exiting the body through the first skin incision site 42 the strap 100 may be tightened. This is shown in FIG. 19H where the lock-head 109 has been placed over both ends of the self-locking strap 100, as previously described in this disclosure (FIGS. 3 and 4), and traction may be applied to both ends of the self-locking strap 100, indicated by arrow 79, to tighten it through the full thickness abdominal wall on both sides of the hernia defect 40.

Figure 19I:
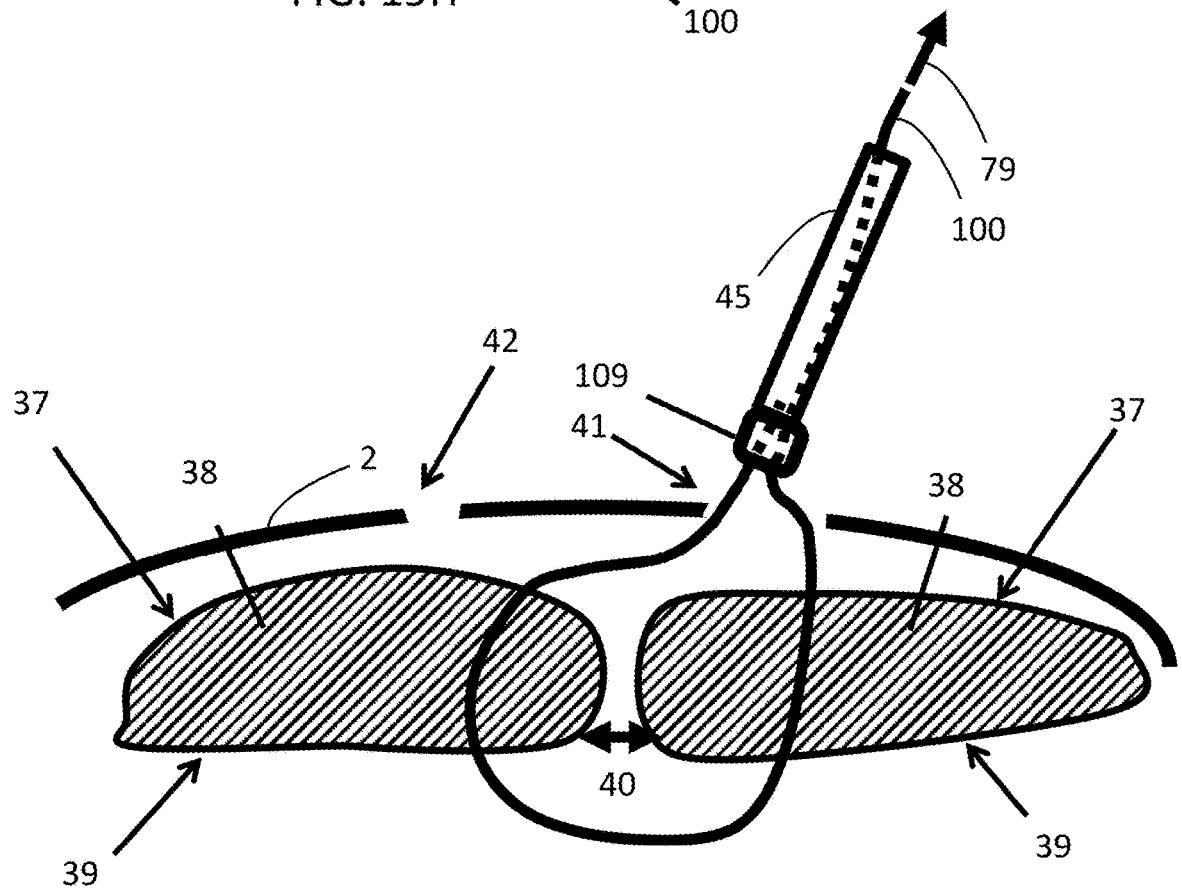
Figure 19J:
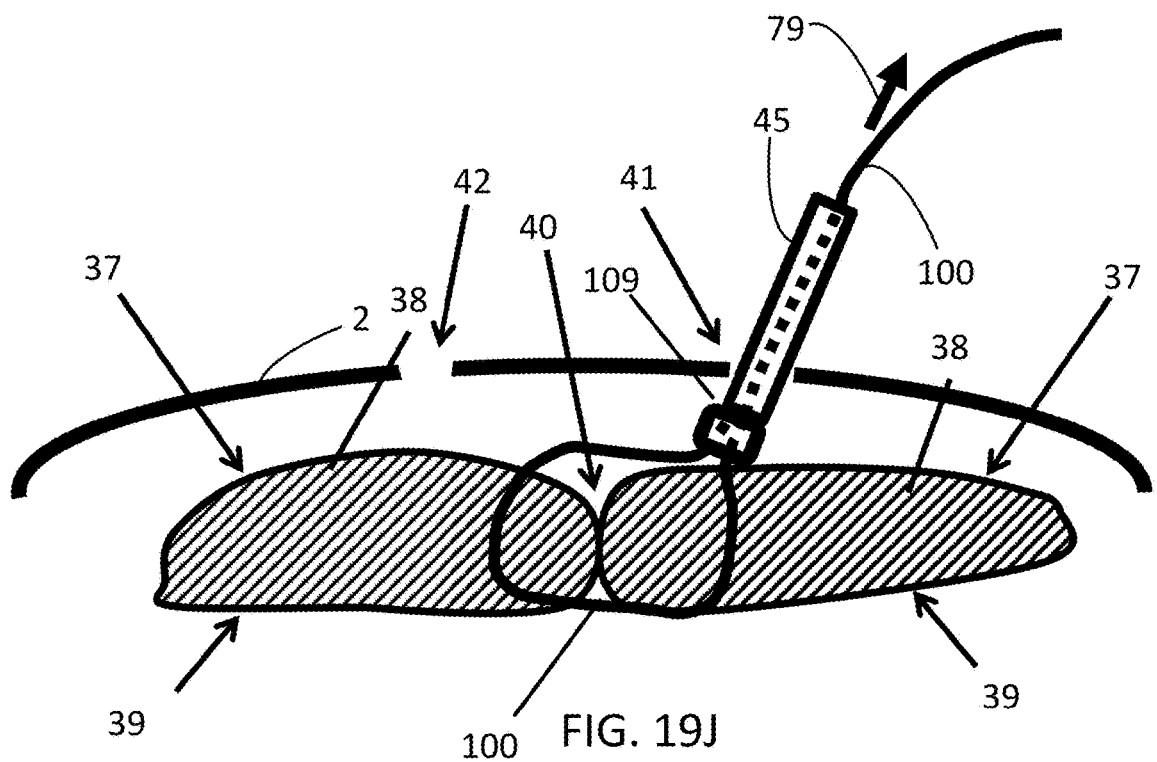
Figure 19K:
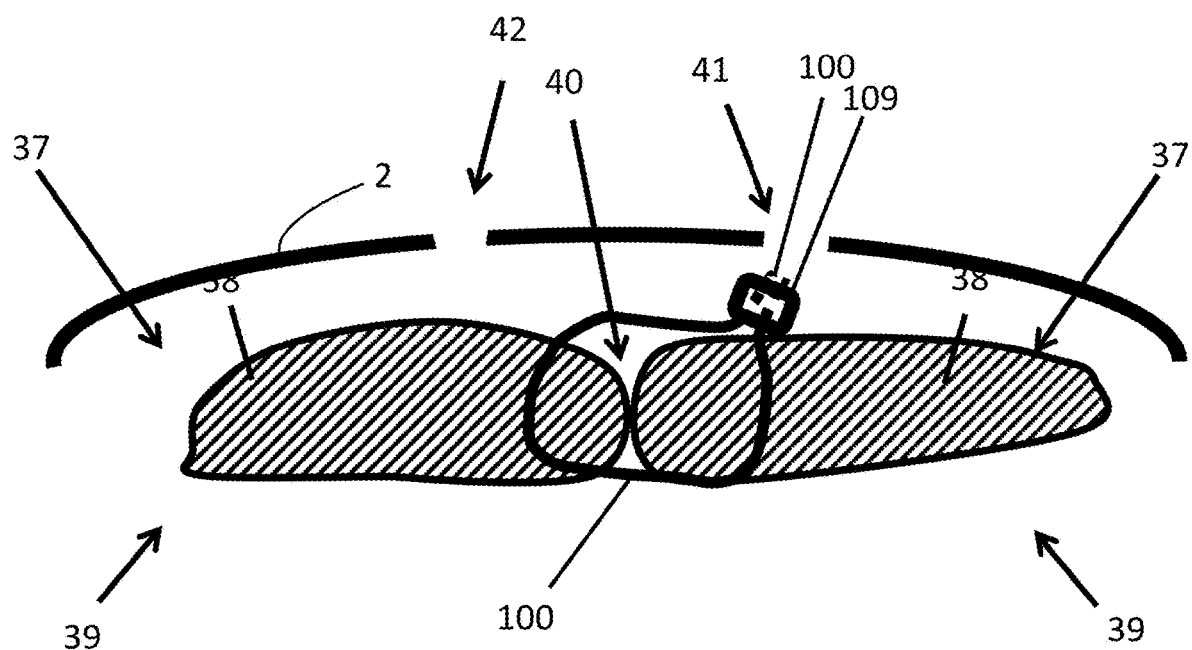

FIG. 19I shows the self-locking strap 10 in the locked configuration as it is being tightened as indicated by the arrow 79. A support tube 45 may be slid over the self-locking strap 100 such that the strap 100 extends through its lumen and the distal end 78 of the support tube 45 may be placed in contact with lock-head 109 to provide counter-traction during the tightening process. Thus, the surgeon may pull on the strap 100 as indicated by the arrow 79 while pushing on the support tube 45 in the opposite direction to tighten the self-locking strap 100 as shown in FIG. 19J. The support tube 45 it may be a tubular device made of any material such that it is strong enough to withstand the tension pulled on the strap 100; the support tube 45 may be made, or a rigid polymeric material such as polycarbonate or a metal, for example, stainless steel. As the surgeon may desire to measure the tension force being applied, the support tube 45 may have a compression spring along its length that connects to a plunger going through its inner lumen, such that when the support tube 45 is pushed, and the strap 100 is pulled, the plunger extends showing a force indication. Alternatively, the tensioning device 190 illustrated in FIGS.

13-16 may be used to tighten the strap 100 while providing an indication of the tension force.

The excess length of strap 100 may be removed by any appropriate method or tool. As previously described herein (FIG. 18K), the tubular cutter 30 may be used. In other embodiments, other devices such as the rotational cutter 175 (FIG. 11) may be used to sever the excess strap. Furthermore, the tensioning device 190 may be used to sever the strap 100 as the device 190 may have transverse cutting blades 201 in its distal end. It will be apparent to one skilled in the art that there are other alternative methods of cutting excess strap without departing from the inventions disclosed herein. Such methods may include snipping the excess self-locking strap 100 with a scalpel, scissors, or forceps, by way of non-limiting example.

Yet another embodiment of a system and method for closing a ventral hernia is disclosed in FIGS. 20A-20I. The system may comprise by way of non-limiting example, a self-locking strap 220, a slotted needle 15, a hook needle 21, a subcutaneous guide 184, a tubular cutter 30, and a support tube 45. The tubular cutter 30 may have an outer tube 34 and an inner tube 31 having a cutting blade 33 attached therein. The aforementioned components are described in further detail in this disclosure. Other components and devices, including those disclosed throughout this application, may be included in the systems and used in the methods disclosed herein, i.e., the system shown is not necessarily a complete surgical kit and other devices and methods may be substituted or added to the system to form other systems or embodiments that are within the scope of the invention(s) disclosed herein. For example, various laparoscopic instruments, such as a laparoscope with a camera may also be used during the surgery Pilot needles 35 may be inserted through skin entry sites 36, and through the full thickness abdominal wall which consists of the anterior rectus sheath 37, the rectus muscle 38, and the posterior rectus sheath 39 as previously shown and described, for example in FIG. 18A. Based on the entry sites of the pilot needles 35, a first skin incision 41 and a second skin incision 42 may be made as previously described and shown, for example, in FIG. 18B.

Figure 20C:
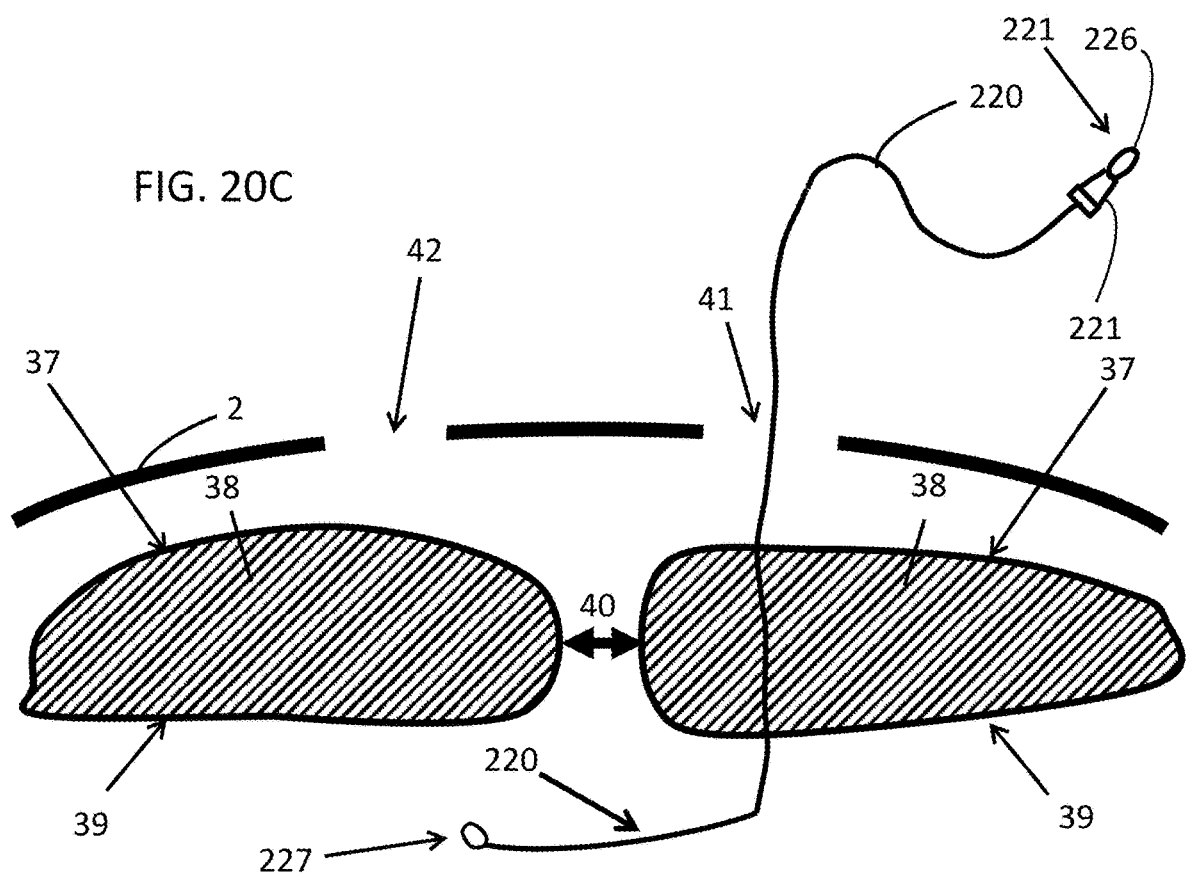
Figure 20D:
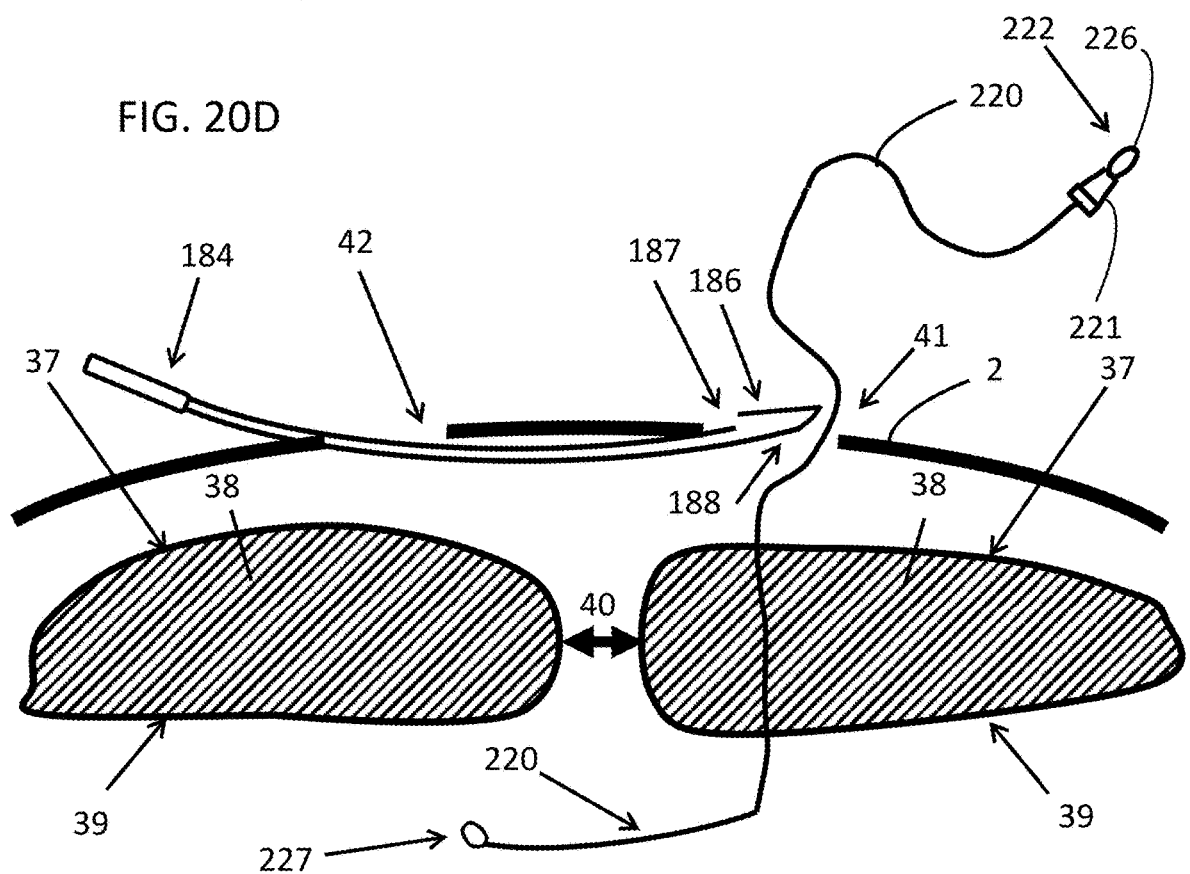

To demonstrate the surgical procedure clearly, the self-locking strap 220 is shown schematically as a line drawing leaving out some details such as locking features such as teeth. In order to introduce the self-locking strap 220 into the body cavity, a slotted needle 15 may be placed through the first incision site 41 and through the full-thickness abdominal wall as shown in FIG. 20A to access the body cavity below the posterior rectus sheath 39. Once the slotted needle 15 is in place, the self-locking strap 220 may be advanced through the slotted needle 15 and into the body cavity as shown in FIG. 20B. With the strap introduced into the body cavity, the strap may be removed from the slotted needle 15 as shown in FIG. 20D. Removing the strap laterally from the slotted needle may allow the slotted needle to be of a small diameter because the lock-head 221, which is attached to the self-locking strap 220, does not need to pass through the lumen of the slotted needle 15. However, if the lock-head 221 can be made as small as the width of the elongate body 229 (FIG. 6A) of the strap 220, then a slot may not be necessary, as the lock-head 221 could be pulled directly through the lumen of a conventional needle. Alternatively, a conventional needle without a slot may be used to pass the self-locking strap 220 therethrough if the needle diameter is large enough to accommodate a lock-head 221 which may be larger than the width of the elongate body 229 of the self-locking strap 220. That is, a needle with a larger diameter than the slotted needle 15 may be used, subject to the general desire to have smaller incisions and smaller needle tracts through the muscle that is germane to minimally invasive surgery. For example, if a large needle or trocar of, for example, 10 mm in diameter were used, the relatively large hole in the fascia would need to be closed via sutures to prevent a localized hernia. Furthermore, the large tract in the muscle may cause weaker tissue where the strap is placed.

With reference to FIG. 20D, the subcutaneous guide 184 is placed spanning from the second skin incision site 42 to the first skin incision site 41 on the opposite side of hernia defect 40 as it dissects and/or tunnels through the intervening tissue between the incision sites 42 and 41. The subcutaneous guide 184 is advanced until the slot 186 appears at the first skin incision site 41. The distal tip 188 of the subcutaneous guide 164 may protrude through the second skin incision site 42 as shown or it may reside below the surface of the skin so that the surgeon may access it to engage the self-locking strap 220. This may be accomplished by, for example, placing the proximal tip 222 of the of the self-locking strap 220 through the gap 187 in the distal tip 188 of the subcutaneous guide 184 such that the subcutaneous guide 184 hooks into the distal aperture 227 of the self-locking strap 220. Once engaged, the subcutaneous guide 184 may be pulled back through the second incision site 42 thus extracting the lock-head 221 across the defect leaving it adjacent to or outside of the second skin incision site 42. One skilled in the art will recognize that there may be other features such as a loop, hook, or protuberance on the end of the strap 220 that may be grasped by the subcutaneous guide 184, or the guide 184 may have grasping features such as a snare, or clamp, or jaws near its distal tip to hold onto any portion of the self-locking strap 220 whether or not the strap 220 has engagement features.

Figure 20E:
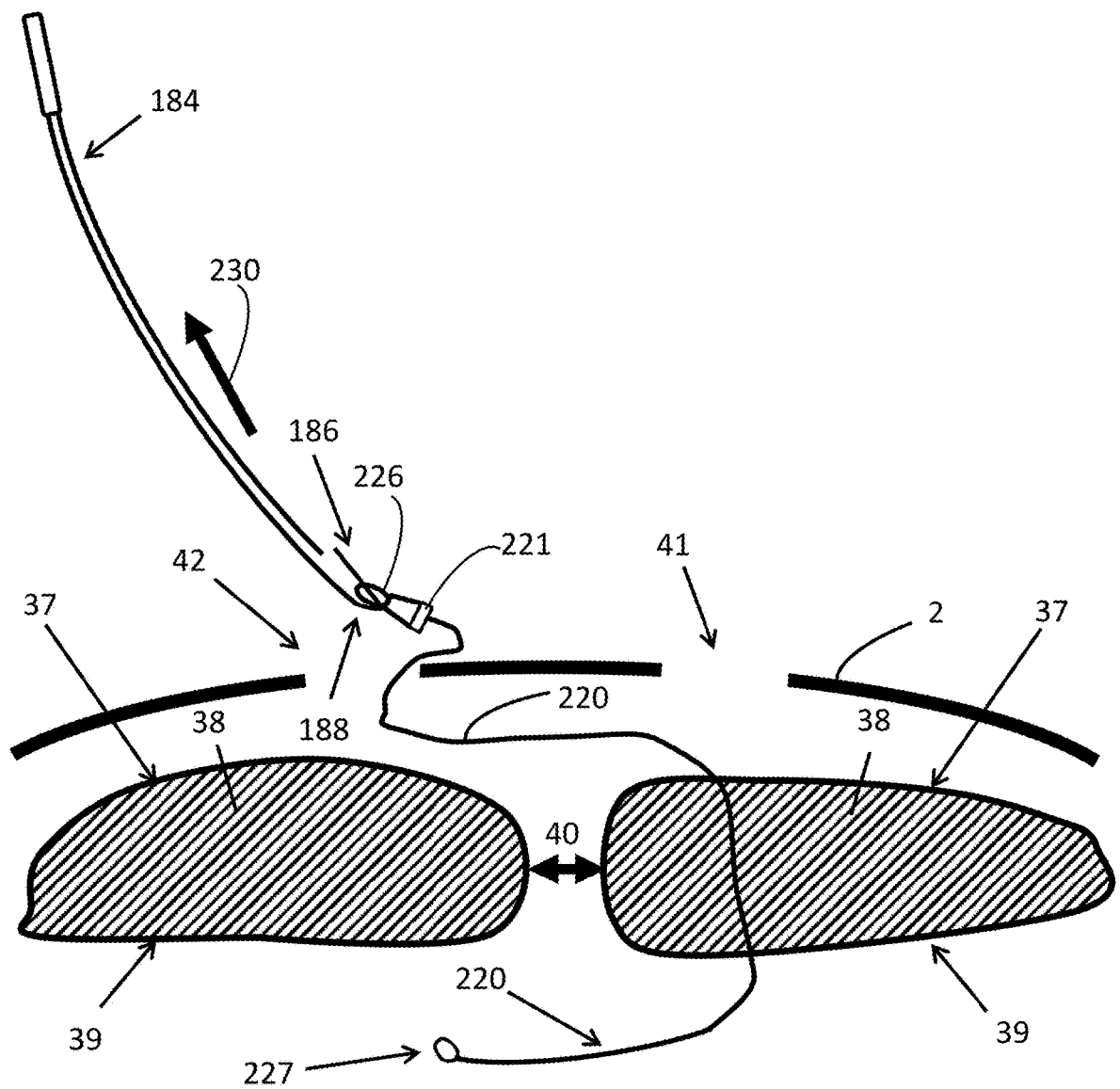

FIG. 20E shows the subcutaneous guide 184 being pulled out of the patient's body as indicated by arrow 230, thereby pulling the self-locking strap 220 out of the body at the second skin incision site 42 as the strap 100 is captured by the hook needle 21.

Figure 20F:
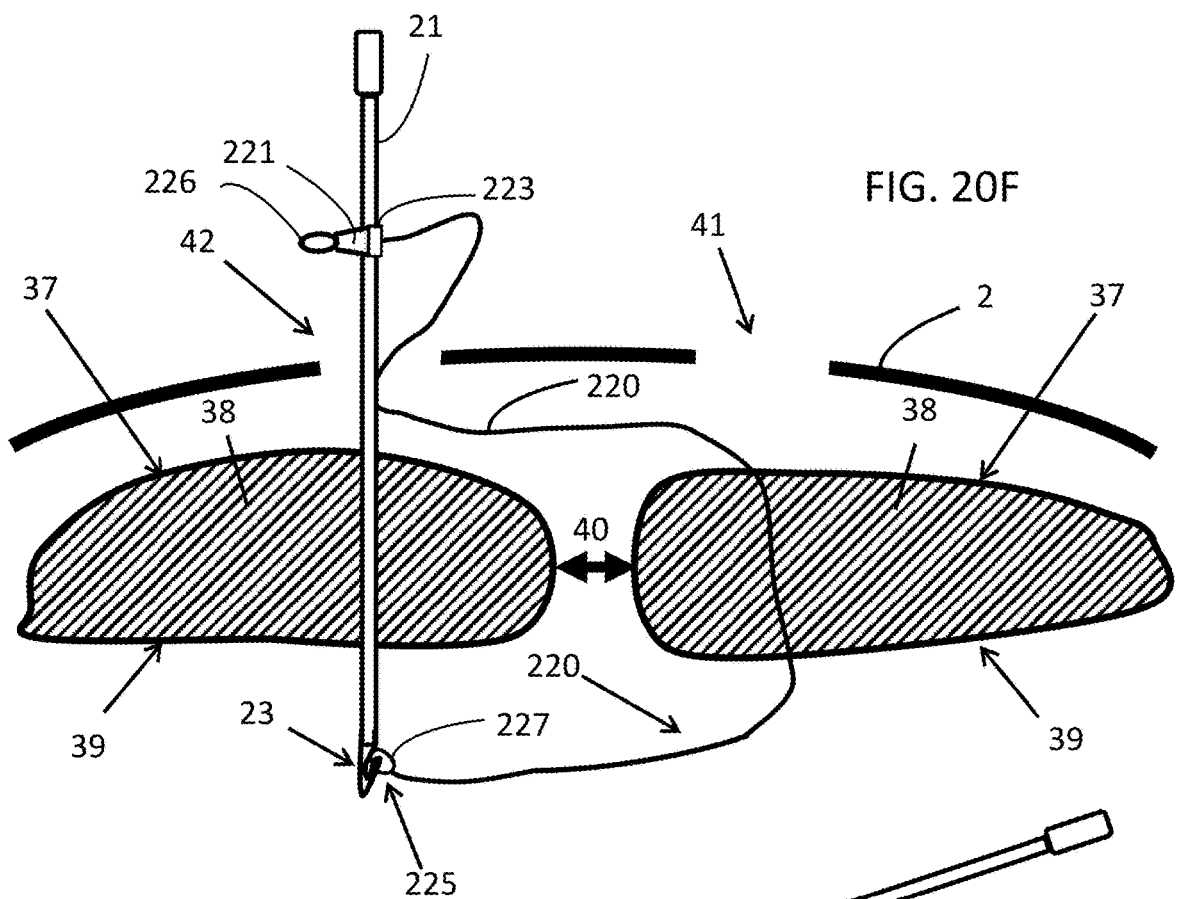
Figure 20G:
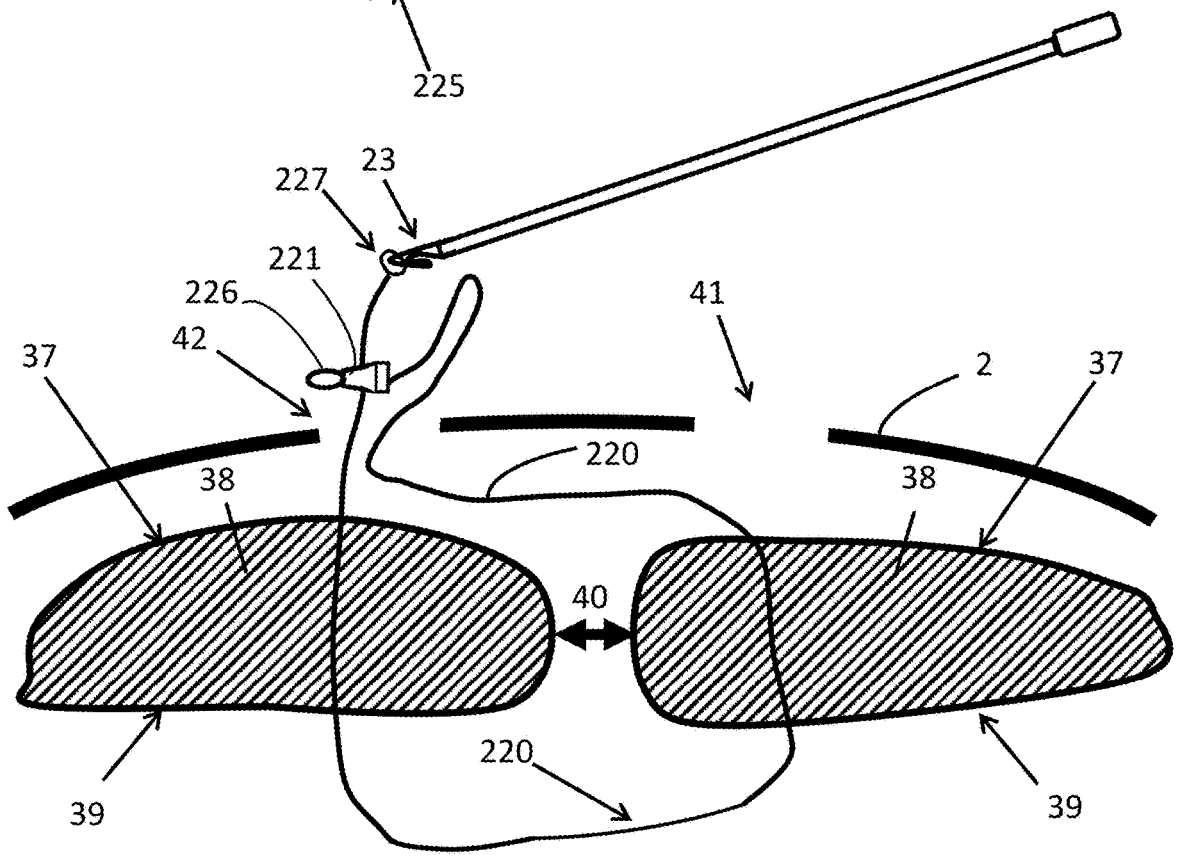
Figure 20H:
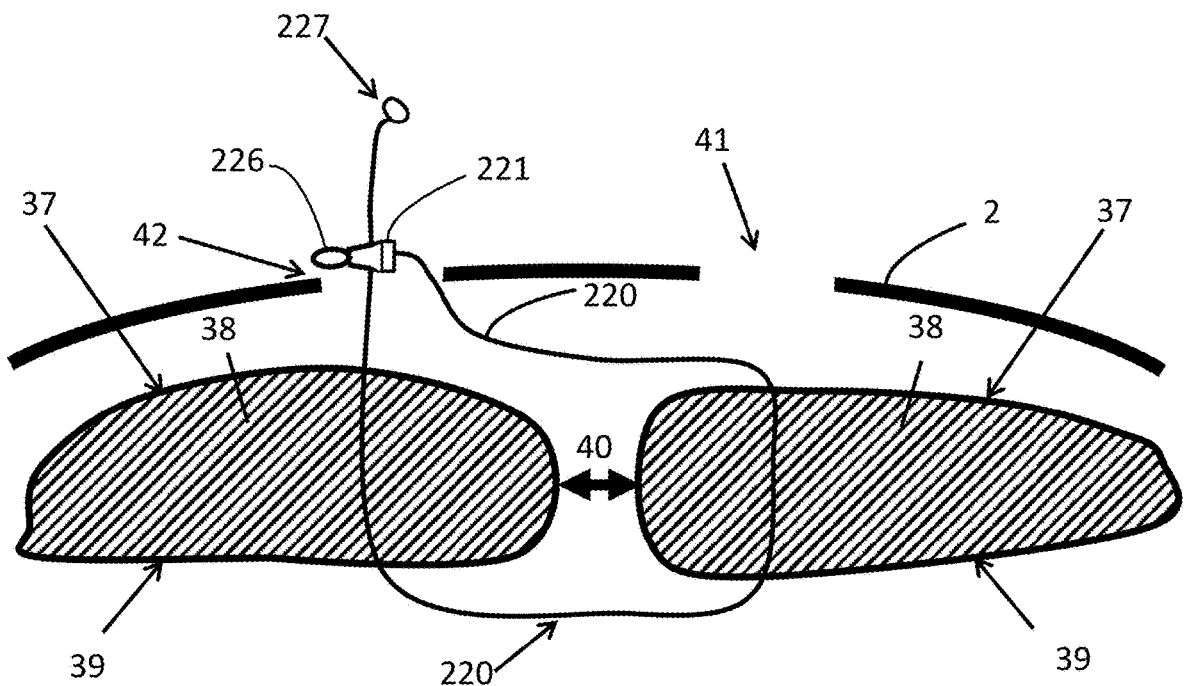

In order to fasten the self-locking strap 220, both ends of the strap 220 should exit from, or at least be accessible from, the same skin incision. This may be accomplished by placing the hook needle 21 through the slot 223 in the lock-head 221 and advancing the hook needle 21 through the full thickness abdominal wall and into the body cavity where the distal tip 225 of the self-locking strap 220 resides, as shown in FIG. 20F. With the needle already placed through the same slot 223 in the lock-head 221 that the distal tip 225 will pass through, the hook needle 21 may be withdrawn from the body, thus pulling the self-locking strap 220 through the full-thickness abdominal wall, and through the lock-head 221 for engagement as shown in FIG. 20G. As shown in FIG. 20H, the self-locking strap 220 may be tightened and the lock-head 221 driven down toward the anterior rectus sheath 37.

Figure 20I:
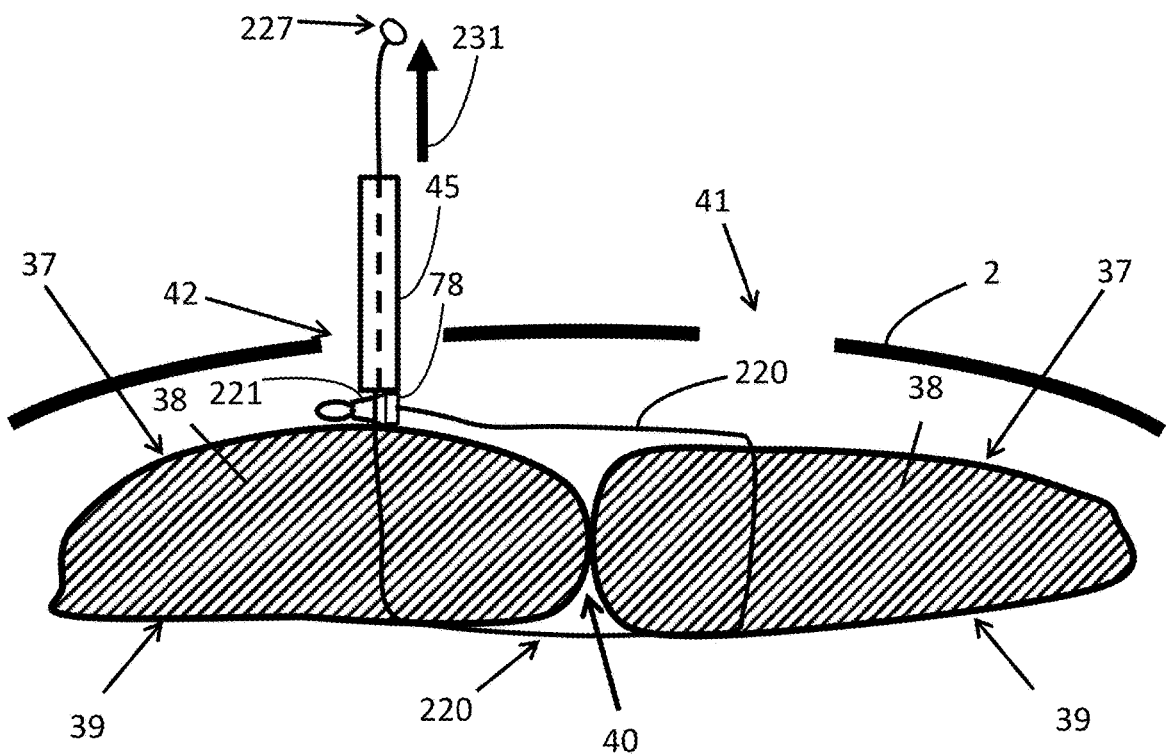

A support tube 45 may be advanced over the self-locking strap 220 such that the strap 220 extends through its lumen and the distal end 78 of the support tube 45 may be placed in contact with lock-head 221 to provide counter-traction during the tightening process. Thus, the surgeon may pull on the strap 220 as indicated by the arrow 231 while pushing on the support tube 45 in the opposite direction to tighten the self-locking strap 220 as shown in FIG. 20I. As the surgeon may desire to measure the tension force being applied, the support tube 45 may have a compression spring along its length that connects to a plunger going through its inner lumen, such that when the support tube 45 is pushed and the strap 220 is pulled, the plunger extends showing a force measurement. Alternatively, other tensioning devices may be used, such as the tensioning device 190 illustrated in FIGS. 12-14 which may be used to tighten the strap 220 while indicating the tension force.

The excess length of strap 220 may be removed by any appropriate method or tool. As previously described herein (FIG. 18K), the tubular cutter 30 may be used. In other embodiments, other devices such as the rotational cutter 175 (FIG. 12) may be used to sever the excess strap. Furthermore, the tensioning device 190 may be used to sever the strap 220 as the device 190 may have transverse cutting blades 200 in its distal end. It will be apparent to one skilled in the art that there are other alternative methods of cutting excess strap without departing from the inventions disclosed herein. Such methods may include snipping the excess self-locking strap 220 with a scalpel, scissors, or forceps, by way of non-limiting example.

The proposed embodiments of this application are simple, less tedious, and requires fewer steps than other minimally invasive techniques. Furthermore, the system also provides the high degree of tension required to close a full-thickness abdominal wall defect. In the present embodiments, no significant tract is formed whereby the strap may pull back through the wall. This reduces the likelihood of failure of the defect closure; the tract through the rectus muscles may be as small as the needles used in the procedure. Furthermore, one skilled in the art would appreciate that the self-locking strap may be sized large enough in diameter to hold the required tension and to resist cutting through tissue as compared to a relatively thin suture, yet small enough to fit through a slotted needle 15.

Systems and methods for closing a fascial opening are described herein. Multiple straps may be delivered to the body, and the process may be repeated as many times as is necessary in order to close the defect. A large defect may require several straps which may be fastened in parallel and incrementally tightened to reappose the defect gradually so as to reduce peak forces on the tissue. Part or all of the systems and devices may be re-used to deliver the multiple straps, or they may be discarded in whole or in part and a new set used for each strap. While the present disclosure describes the system and method in the context of hernia repair, and in particular ventral hernia repair, the devices and methods presently disclosed may be used in any surgical procedure for joining tissue, closing an opening, or fastening a device to or between two or more sections of tissue. Additionally, while the current disclosure describes a method in the context of laparoscopic surgery, the method may be applied to any other class of procedure such as open surgery or laparotomy. Furthermore, the presently disclosed systems and methods may optionally incorporate a hernia mesh similar to those used in typical hernia repair procedures or any new mesh systems or methods of application that may arise.

Figures 21A, 21B:
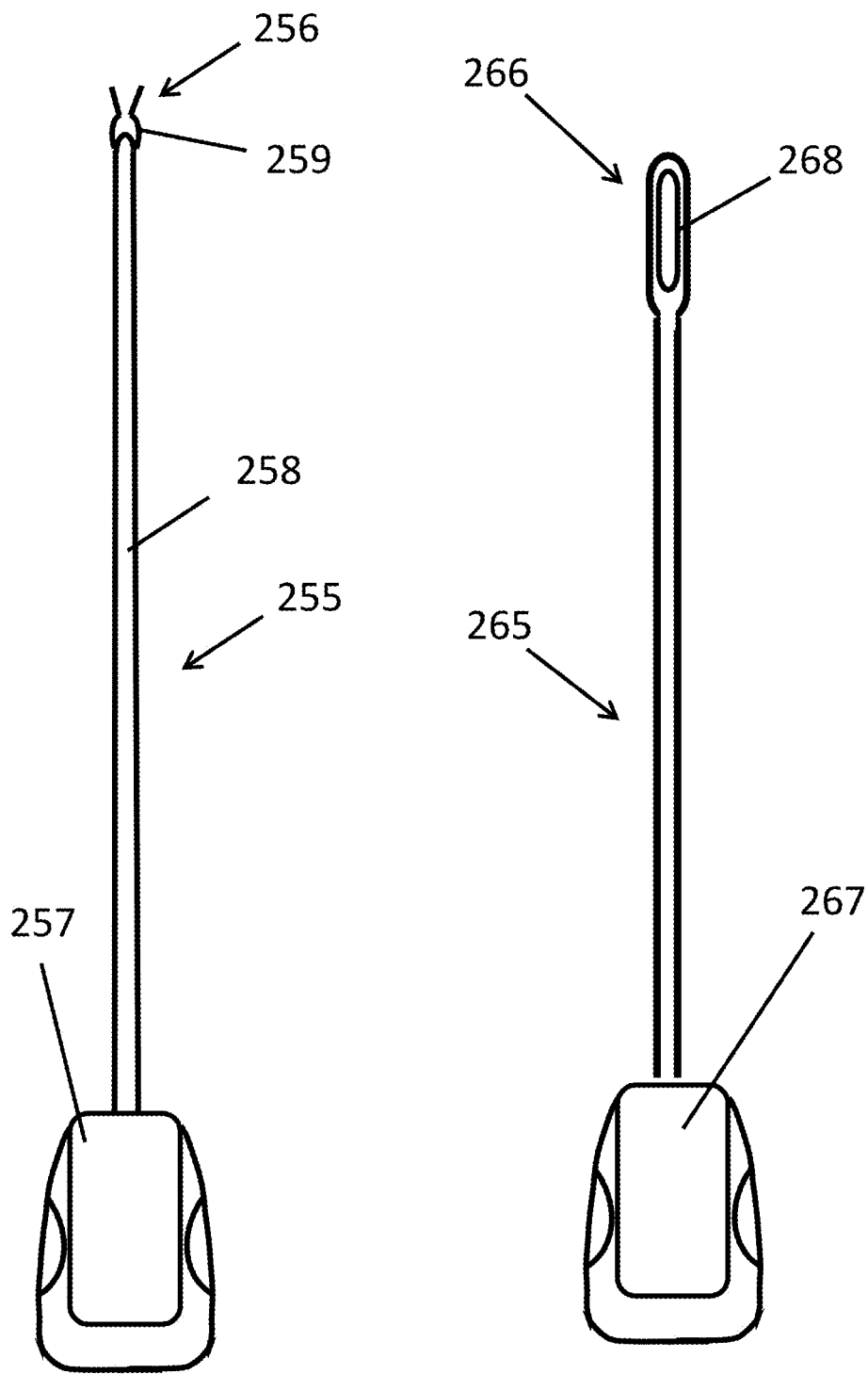
FIGS. 21A-21C illustrate embodiments devices with a surgical robotic interface.

The technique of laparoscopic ventral hernia repair using the self-locking straps may be performed with the assistance of robotic surgical technology. Robotic assistance may impart enhanced control to multiple steps in the manual techniques described herein. For example, subcutaneous passage of the subcutaneous guide requires exertion of substantial dissection force to drive the guide through the tissue which may be fatty and fibrous; use of a robotic arm may allow smooth advancement of the needle guide through tissue, whereas manual passage in fibrous tissue may cause jerky movements that may result in errant insertion of the guide into the rectus muscle or the peritoneal cavity. As such, the proximal end of the any of the devices used in the procedures disclosed herein may contain a connector for attachment to the distal end of the robotic arm which may have a standard or custom connection to interface with the connector. For example, FIG. 21A shows a laparoscopic grasper 255 which includes an elongate shaft 258 supporting an end effector 256 and a robotic arm interface 257 that attaches to a surgical robotic arm (not shown). The robotic arm interface 257 may receive and transmit drive signals and motion between a robotic arm and the end effector 256 and may interface with the robotic system via a quick release mechanism. An articulating wrist joint 259 may provide two degrees of freedom of motion between the end effector 256 and the shaft 258, and the shaft 258 may be rotatable relative to the robotic arm interface 257 resulting in three operational degrees of freedom of operation at the end effector 256. As an example, robotic assistance may be used during transfer of the distal end of the self-locking strap to the hook needle as shown previously in FIG. 19D. The laparoscopic grasper 255 may be inserted into the abdominal cavity to grasp the distal end of the strap, maneuver it towards the hook needle, and stabilize it as it is secured by the hook needle.

Figure 21C:
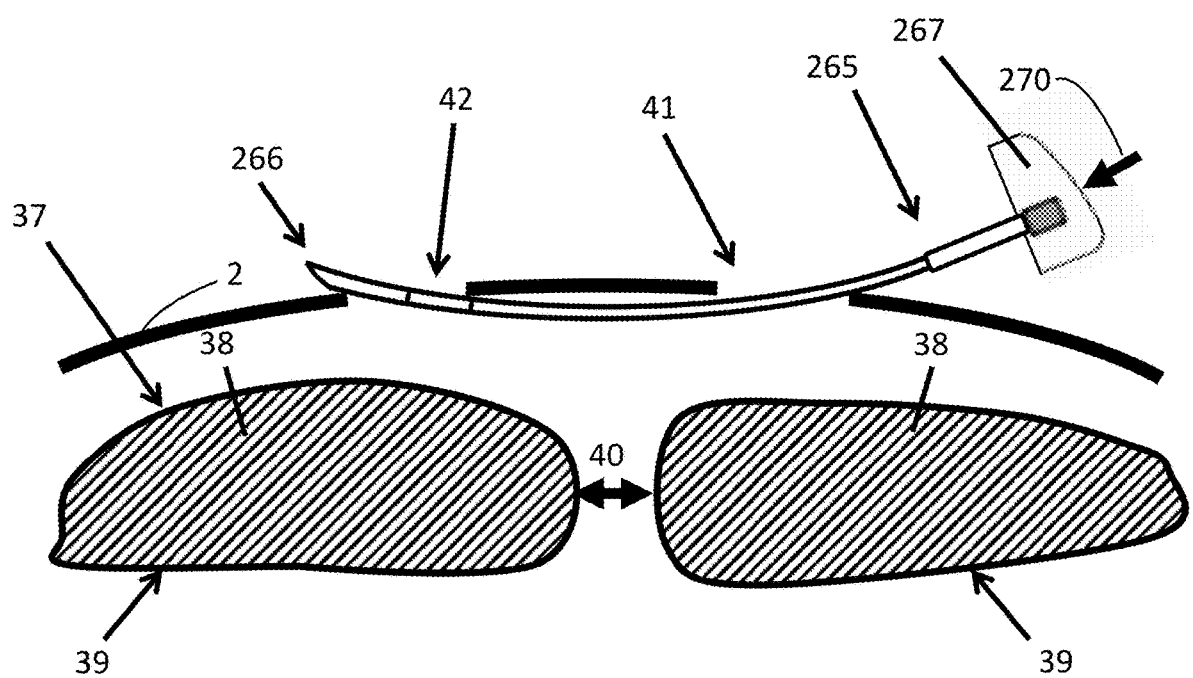

FIG. 21B shows a subcutaneous guide 265 with a distal end 266 having a slot 268. The subcutaneous guide 265 may have a robotic arm interface 267 located at its proximal end, and robotic control may be used to manipulate the subcutaneous guide during subcutaneous dissection as shown in FIG. 21C. The force, as indicated by the arrow 270, may be better controlled by a surgical arm as compared to a manual procedure as higher forces may be applied by the robotic system in a more controlled fashion. Robotic assistance also facilitates intra-abdominal instrument movements performed under laparoscopic visualization.

While this invention has been particularly shown and described with references to example embodiments thereof, it will be understood by those skilled in the art that various changes in form and details may be made therein without departing from the scope of the invention(s) encompassed by the appended claims. While the above is a complete description of the certain embodiments of the invention, various alternatives, modifications, and equivalents may be used. The various devices and method steps of the embodiments disclosed herein may be combined or substituted with one another, and such alternative embodiments fall within the scope of the claimed invention(s). Therefore, the above description should not be taken as limiting in scope of the invention(a) which is defined by the appended claims.

What is claimed is:

1. A system for closing a tissue defect, the system comprising: a self-locking strap having a lock-head;
    a first needle having a lumen for delivering the self-locking strap through a first incision site;
    a second needle having a hook on its distal end for engaging the self-locking strap and pulling the strap from the body through a second incision site; and
    a guide having an aperture near its distal end for passing the second needle therethrough and retaining the strap after the second needle is removed from the aperture,
    wherein the first needle includes a slot along its length for removing the self-locking strap.

2. The system of claim 1 further comprising a support tube for pushing on the self-locking strap while the strap is being tensioned.

3. The system of claim 1 further comprising a rotational cutter with at least one distal blade for severing the self-locking strap adjacent to the lock-head.

4. The system of claim 1 further comprising a tensioner having at least one movable lock-head to incrementally tension the self-locking strap.

5. The system of claim 4 wherein the tensioner includes a tension gauge to measure the tension in the strap.

6. The system of claim 5 further comprising an indicator to display the tension in the strap.

7. The system of claim 6 wherein the tension gauge is one of a mechanical spring gauge or a force transducer.

8. The system of claim 5 wherein the tension gauge is configured to convert the tension force into an electrical signal and transmit the electrical signal to a display or receiving computer.

9. The system of claim 1 further comprising laparoscopic grasper configured to place the self-locking strap into engagement with the second needle.

10. The system of claim 9 wherein the laparoscopic grasper includes a robotic arm interface and is robotically controlled.

11. The system of claim 1 further comprising a separate lock-head capable of receiving both ends of the strap.

12. The system of claim 1 wherein the self-locking strap has a protuberance at its distal end configured to engage with the second needle.

13. The system of claim 1 further comprising a robotic interface fixed to the distal end of the guide.

14. The system of claim 1 wherein the strap further comprises a plurality of apertures through the strap configured to facilitate ingrowth of tissue.

15. A method for closing a tissue defect, the method comprising:
positioning a guide beneath the skin between a first incision and a second incision in the body of a patient so that the distal end of the guide resides near the second incision;
inserting a first needle through the first incision;
inserting a second needle through the second incision and through an aperture placing a distal end of a self-locking strap through the first needle and into the guide;
the body cavity;
engaging the second needle with the distal end of the strap;
pulling the second needle through the guide and out of the body leaving the strap captured by the aperture in the guide;
releasing the strap from the first needle;
pulling the guide out of the body through the first incision so that the distal end of the self-locking strap exits the first incision; and
placing a lock-head over the distal end of the self-locking strap and advancing the lock-head head down the self-locking strap to tighten the self-locking strap around a defect.

16. The method of claim 15 wherein a laparoscopic grasper is used to engage the second needle with the distal end of the strap.

17. The method of claim 16 wherein the laparoscopic grasper is robotically controlled.

18. The method of claim 15 further comprising the step of placing pilot needles through the skin and muscle tissue to determine the correct distance lateral to the defect for inserting surgical instruments.

19. The method of claim 15 wherein the first needle includes a hook at its distal end configured to engage with the self-locking strap.

20. The method of claim 15 wherein the first needle includes a slot through which to withdraw the self-locking strap laterally from the needle.

21. The method of claim 15 wherein the self-locking strap is released through the slot in the first needle.

22. The method of claim 15 further comprising the step of placing a support tube over the self-locking strap and pulling the self-locking strap while pushing the support tube to tighten the self-locking strap.

23. The method of claim 15 further comprising the step of cutting the self-locking strap inside of the body adjacent to the lock-head.

24. The method of claim 15 further comprising the step of tightening the self-locking strap with a tensioner having at least one lock-head to incrementally tighten the self-locking strap.

25. The method of claim 24 wherein the tensioner includes a tension gauge to measure the tension in the strap.

26. The method of claim 25 further comprising an indicator that displays the tension force.

27. The method of claim 25 wherein the tension gauge is a mechanical spring gauge.

28. The method of claim 25 wherein the tension gauge is a force transducer.

29. The method of claim 25 further comprising converting the measured tension into an electrical signal and transmitting the electrical signal to a display or receiving computer.

30. The method of claim 15 wherein the guide is robotically controlled.

31. The method of claim 15 wherein the strap includes a plurality of apertures through the strap to facilitate ingrowth of tissue.

32. A method for closing a tissue defect, the method comprising:
inserting a first needle through a first incision and into a body cavity on a first side of a defect;
placing the distal end of a self-locking strap through the first needle and into the body cavity;
retracting the first needle from the body;
removing the first needle from the strap while leaving the strap inside of the body;
placing a guide through a second incision site on the opposite side of the defect and advancing the guide subcutaneously to the first incision site;
engaging the proximal end of the strap with the guide and pulling the proximal end of the strap subcutaneously across the defect to the second incision site;
placing a second needle through a lock-head attached to the proximal end of the strap and advancing the needle into the body cavity to engage the distal end of the strap; pulling the distal end of the strap out through muscle tissue and through the lock-head with the second needle; and
tightening the strap to approximate the defect.

33. The method of claim 32 further comprising the step of placing pilot needles through the skin and muscle tissue to determine the distance lateral to the defect for inserting surgical instruments.

34. The method of claim 32 wherein a laparoscopic grasper is used to engage the second needle with the distal end of the strap.

35. The method of claim 34 wherein the laparoscopic grasper is robotically controlled.

36. The method of claim 32 wherein the second needle includes a hook at its distal end for engaging with the self-locking strap.

37. The method of claim 32 wherein the first needle includes a slot through which to withdraw the self-locking strap laterally from the needle.

38. The method of claim 32 wherein the self-locking strap is released through the slot in the first needle.

39. The method of claim 32 further comprising the step of placing a support tube over the self-locking strap to tighten the self-locking strap.

40. The method of claim 32 further comprising the step of cutting the self-locking strap inside of the body adjacent to the lock-head.

41. The method of claim 32 further comprising the step of tightening the self-locking strap with a tensioner having at least one lock-head to incrementally tighten the self-locking strap.

42. The method of claim 41 wherein the tensioner includes a tension gauge to measure the tension in the strap.

43. The method of claim 42 wherein the tension gauge includes an indicator that displays the tension force.

44. The method of claim 42 wherein the tension gauge is a mechanical spring gauge.

45. The method of claim 42 wherein the tension gauge is a force transducer.

46. The method of claim 42 wherein the tension gauge converts the measured tension into an electrical signal and transmitting the electrical signal to a display or receiving computer.

47. The method of claim 42 wherein the guide is robotically controlled.

48. The method of claim 42 wherein the strap includes a plurality of apertures through the strap to facilitate ingrowth of tissue.

49. A system for closing a tissue defect, the system comprising:
a self-locking strap having a lock-head at its proximal end;
a first needle having a lumen for delivering the distal end of the self-locking strap through a first incision site;
a guide for tunneling through subcutaneous tissue from the first incision site to a second incision site, the guide having a hook near its distal end for engaging with the self-locking strap and pulling the strap back through the subcutaneous tissue to the first incision site;
a second needle having a hook at its distal end, the second needle being capable of passing through the lock-head and engaging with the distal end of the self-locking strap and pulling the distal end of the strap through the lock-head and out of the body; and
a linear cutter having an inner tube with a lumen, an outer tube, and a radially flexing cutter that depresses into the lumen of the inner tube when forced by the outer tube.

50. The system of claim 49 further comprising support tube for pushing on the self-locking strap while the strap is being tensioned.

51. The system of claim 49 further comprising a rotational cutter with at least one distal blade for severing the self-locking strap adjacent to the lock-head.

52. The system of claim 49 further comprising tensioner having at least one movable lock-head to incrementally tension the self-locking strap.

53. The system of claim 52 wherein the tensioner includes a tension gauge to measure the tension in the strap.

54. The system of claim 53 further comprising an indicator to display the tension in the strap.

55. The system of claim 53 wherein the tension gauge is a mechanical spring gauge.

56. The system of claim 53 wherein the tension gauge is a force transducer.

57. The system of claim 53 wherein the tension gauge is capable of converting the measured tension into an electrical signal and transmitting the electrical signal to a display or receiving computer.

58. The system of claim 49 further comprising a laparoscopic grasper for placing the self-locking strap into engagement with the second needle.

59. The system of claim 49 wherein the laparoscopic grasper includes a robotic arm interface and is robotically controlled.

60. The system of claim 49 wherein the self-locking strap has an aperture at its proximal end.

61. The system of claim 49 wherein the self-locking strap has an aperture at its distal end.

62. The system of claim 49 wherein the first needle includes a slot along its length for removing the self-locking strap.

63. The system of claim 49 further comprising a robotic interface fixed to the distal end of the guide.

64. The system of claim 49 wherein the strap includes a plurality of apertures through the strap to facilitate ingrowth of tissue.

65. A device for tensioning a self-locking strap, the device comprising:
a shaft;
a plunger slidably disposed on the shaft;
a stationary lock-head distal to the plunger and affixed to the shaft;
a movable lock-head affixed to the plunger and aligned with the stationary lock-head wherein the movable lock-head and the stationary lock-head are configured to allow a strap to pass through each lock-head;
a frame slidably attached to the shaft and located distal to the stationary lock-head; a compression spring compressed between the frame and the stationary lock-head; and
an elongate tube extending distally from the frame, the tube configured to abut against the lock-head of a self-locking strap inside of a human body.

66. The device of claim 65 further comprising a set of force markings located on the distal portion of the shaft configured to read the amount of force on a strap that is held by the stationary lock.

67. The device of claim 65 further comprising a force transducer configured to read the amount of force on a strap that is held by the stationary lock while the elongate tube abuts against the lock-head of the strap.

68. The device of claim 65 wherein the tension gauge is capable of converting the tension force into an electrical signal and transmitting the electrical signal to a display or receiving computer.

69. A self-locking strap comprising:
an elongate body having a distal end, a proximal end, a top side and a bottom side;
a first set of ramped teeth on the top side;
a second set of ramped teeth on the top side having a ramp direction in the opposite direction to the first set of teeth;
a third set of ramped teeth on the bottom side having a ramp direction in the same direction as the first set of teeth;
a fourth set of ramped teeth on the bottom side having a ramp direction in the same direction as the second set of teeth;

a detached lock-head having an aperture capable of passing the distal end and proximal end simultaneously; and wherein the lock-head has a set of opposing pawls protruding into the aperture for engaging with the distal end and the proximal end, and wherein the third set of ramped teeth are offset longitudinally from the first set of ramped teeth and the fourth set of ramped teeth are offset longitudinally from the second set of ramped teeth, to provide a wider minimum cross-sectional thickness to the strap.

70. The self-locking strap of claim 69 further comprising a plurality of apertures through the strap to facilitate tissue ingrowth.

71. The self-locking strap of claim 69 wherein the distal and proximal ends of the strap are tapered and have an aperture therethrough to engage with a surgical instrument.

* * * * *